(12) United States Patent
Karas et al.

(10) Patent No.: US 10,351,860 B2
(45) Date of Patent: Jul. 16, 2019

(54) HIGH EFFICIENCY METHOD FOR ALGAL TRANSFORMATION

(71) Applicant: Synthetic Genomics, Inc., La Jolla, CA (US)

(72) Inventors: Bogumil Karas, London (CA); Christopher L. Dupont, La Jolla, CA (US); Philip D. Weyman, La Jolla, CA (US); Andrew E. Allen, La Jolla, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 181 days.

(21) Appl. No.: 15/048,882

(22) Filed: Feb. 19, 2016

(65) Prior Publication Data

US 2016/0244770 A1 Aug. 25, 2016

Related U.S. Application Data

(60) Provisional application No. 62/118,408, filed on Feb. 19, 2015.

(51) Int. Cl.
*C12N 15/79* (2006.01)
*C12N 1/12* (2006.01)

(52) U.S. Cl.
CPC ............... *C12N 15/79* (2013.01); *C12N 1/12* (2013.01)

(58) Field of Classification Search
None
See application file for complete search history.

(56) References Cited

U.S. PATENT DOCUMENTS

2010/0041035 A1 2/2010 Zieler et al.

FOREIGN PATENT DOCUMENTS

WO WO 2014/089513 A1 6/2014

OTHER PUBLICATIONS

Encinas et al.: "Plasmid conjugation from proteobacteria as evidence for the origin of xenologous genes in cyanobacteria"; J Bacteriol, Apr. 2014, vol. 196, No. 8, pp. 1551-1559.
International Search Report dated Jul. 26, 2016, regarding PCT/US2016/018766.

*Primary Examiner* — Elizabeth F Mcelwain
(74) *Attorney, Agent, or Firm* — DLA Piper LLP (US)

(57) ABSTRACT

The present invention relates to the seminal discovery of a highly efficient method of transforming algal cells. Specifically, the invention relates to a novel method of delivering a plasmid containing a nucleic acid molecule to algal cells by bacterial conjugation wherein the plasmid remains episomal in the algal cell through multiple generations.

33 Claims, 24 Drawing Sheets
Specification includes a Sequence Listing.

| Exp # | P. tricornutum culture characteristics: Cell culture (L = liquid, P = plates), F = chlorophyll A autofluorescence (for liquid cultures only). Cell morphotype (fusiform, ovoid, triradiate), Final concentration of cells, Amount used | Cargo Plasmid used | E. coli culture $OD_{600}$, amount used in conjugation reaction, used directly or concentrated in SOC media | Initial plates during conjug-ation | Time at 30°C for conjug-ation | Time at 18°C after 30 °C and before selection | How much scraped cells was plated on selection plates | Number of ex-conjugant colonies (after 14 days or more) |
|---|---|---|---|---|---|---|---|---|
| 1 | L, F ~200, fusiforms, Final $1.0 \times 10^8$, 200µl | p0521s | 0.31, 400µl (directly) | L1, 5%LB | 120 min | 1 day | 400 µl | 0 |
| 2 | L, F ~200, fusiforms, Final $1.0 \times 10^8$, 200µl | p0521s | 0.31, 400µl (directly) | L1, 5%LB | 120 min | 1 day | 400 µl | 0 |
| 3 | L, F ~200, fusiforms, Final $1.0 \times 10^8$, 200µl | p0521s | 0.31, 400µl (directly) | L1, 5%LB | 120 min | 1 day | 800 µl | 0 |
| 4 | L, F ~200, fusiforms, Final $1.0 \times 10^8$, 200µl | p0521s | 0.31, 400µl (directly) | L1, 5%LB | 120 min | 1 day | 800 µl | 2 |
| 5 | L, F ~200, fusiforms, Final $1.0 \times 10^8$, 200µl | p0521s | 0.31, 400µl (directly) | L1, 5%LB | 120 min | 2 days | 400 µl | 5 |
| 6 | L, F ~200, fusiforms, Final $1.0 \times 10^8$, 200µl | p0521s | 0.31, 400µl (directly) | L1, 5%LB | 120 min | 2 days | 400 µl | 0 |
| 7 | L, F ~200, fusiforms, Final $1.0 \times 10^8$, 200µl | p0521s | 0.31, 400µl (directly) | L1, 5%LB | 120 min | 2 days | 800 µl | 4 |
| 8 | L, F ~200, fusiforms, Final $1.0 \times 10^8$, 200µl | p0521s | 0.31, 400µl (directly) | L1, 5%LB | 120 min | 2 days | 800 µl | 8 |
| 9 | P, 70% fusiform, 30% oval, Final $1.0 \times 10^8$, 200µl | p0521s | 0.31, 400µl (directly) | L1, 5%LB | 120 min | 1 day | 400 µl | 4 |
| 10 | P, 70% fusiform, 30% oval, Final $1.0 \times 10^8$, 200µl | p0521s | 0.31, 400µl (directly) | L1, 5%LB | 120 min | 1 day | 400 µl | 1 |
| 11 | P, 70% fusiform, 30% oval, Final $1.0 \times 10^8$, 200µl | p0521s | 0.31, 400µl (directly) | L1, 5%LB | 120 min | 1 day | 800 µl | 4 |
| 12 | P, 70% fusiform, 30% oval, Final $1.0 \times 10^8$, 200µl | p0521s | 0.31, 400µl (directly) | L1, 5%LB | 120 min | 1 day | 800 µl | 0 |
| 13 | P, 70% fusiform, 30% oval, Final $1.0 \times 108$, 200µl | p0521s | 0.31, 400µl (directly) | L1, 5%LB | 120 min | 2 days | 400 µl | 5 |

FIG. 1A

| Exp # | P. tricornutum culture characteristics: Cell culture (L = liquid, P = plates), F = chlorophyll A autofluorescence (for liquid cultures only), Cell morphotype (fusiform, ovoid, triradiate), Final concentration of cells, Amount used | Cargo Plasmid used | E. coli culture OD$_{600}$, amount used in conjugation reaction, used directly or concentrated in SOC media | Initial plates during conjug-ation | Time at 30°C for conjug-ation | Time at 18°C after 30°C and before selection | How much scraped cells was plated on selection plates | Number of ex-conjugant colonies (after 14 days or more) |
|---|---|---|---|---|---|---|---|---|
| 14 | P, 70% fusiform, 30% oval, Final 1.0x10$^8$, 200µl | p0521s | 0.31, 400µl (directly) | L1, 5%LB | 120 min | 2 days | 400 µl | 3 |
| 15 | P, 70% fusiform, 30% oval, Final 1.0x10$^8$, 200µl | p0521s | 0.31, 400µl (directly) | L1, 5%LB | 120 min | 2 days | 800 µl | 4 |
| 16 | P, 70% fusiform, 30% oval, Final 1.0x10$^8$, 200µl | p0521s | 0.31, 400µl (directly) | L1, 5%LB | 120 min | 2 days | 800 µl | 6 |
| 17 | L, F ~200, fusiform, Final 1.0x10$^8$, 300µl | p0521s | 0.41, 300µl (directly) | L1 only | 120 min | 1 day | 800 µl | 0 |
| 18 | L, F ~200, fusiform, Final 1.0x10$^8$, 300µl | p0521s | 0.41, 300µl (directly) | L1 only | 120 min | 1 day | 800 µl | 1 |
| 19 | L, F ~200, fusiform, Final 1.0x10$^8$, 300µl | p0521s | 0.41, 300µl (directly) | L1, 5%LB | 120 min | 1 day | 800 µl | 1 |
| 20 | L, F ~200, fusiform, Final 1.0x10$^8$, 300µl | p0521s | 0.41, 300µl (directly) | L1, 5%LB | 120 min | 1 day | 800 µl | 0 |
| 21 | L, F ~200, fusiform, Final 1.0x10$^8$, 300µl | p0521s | 0.41, 300µl (directly) | L1, 10%LB | 120 min | 1 day | 800 µl | 1 |
| 22 | L, F ~200, fusiform, Final 1.0x10$^8$, 300µl | p0521s | 0.41, 300µl (directly) | L1, 10%LB | 120 min | 1 day | 800 µl | 1 |
| 23 | L, F ~200, fusiform, Final 1.0x10$^8$, 300µl | p0521s | 0.41, 300µl (directly) | L1, 20%LB | 120 min | 1 day | 800 µl | 2 |
| 24 | L, F ~200, fusiform, Final 1.0x10$^8$, 300µl | p0521s | 0.41, 300µl (directly) | L1, 20%LB | 120 min | 1 day | 800 µl | 1 |
| 25 | L, F ~200, fusiform, Final 1.0x10$^8$, 200µl | p0521s | 0.38, 400µl (directly) | L1, 5%LB | 30 min | 1 day | 800 µl | 2 |
| 26 | L, F ~200, fusiform, Final 1.0x10$^8$, 200µl | p0521s | 0.38, 400µl (directly) | L1, 5%LB | 30 min | 1 day | 800 µl | 1 |

FIG. 1B

| Exp # | P. tricornutum culture characteristics: Cell culture (L = liquid, P = plates), F = chlorophyll A autofluorescence (for liquid cultures only), Cell morphotype (fusiform, ovoid, triradiate), Final concentration of cells, Amount used | Cargo Plasmid used | E. coli culture OD$_{600}$ amount used in conjugation reaction, used directly or concentrated in SOC media | Initial plates during conjug-ation | Time at 30°C for conjug-ation | Time at 18°C after 30 °C and before selection | How much scraped cells was plated on selection plates | Number of ex-conjugant colonies (after 14 days or more) |
|---|---|---|---|---|---|---|---|---|
| 27 | L, F ~200, fusiform, Final 1.0x10$^8$, 200µl | p0521s | 0.38, 400µl (directly) | L1, 5%LB | 60 min | 1 day | 800 µl | 4 |
| 28 | L, F ~200, fusiform, Final 1.0x10$^8$, 200µl | p0521s | 0.38, 400µl (directly) | L1, 5%LB | 60 min | 1 day | 800 µl | 3 |
| 29 | L, F ~200, fusiform, Final 1.0x10$^8$, 200µl | p0521s | 0.38, 400µl (directly) | L1, 5%LB | 90 min | 1 day | 800 µl | 3 |
| 30 | L, F ~200, fusiform, Final 1.0x10$^8$, 200µl | p0521s | 0.38, 400µl (directly) | L1, 5%LB | 90 min | 1 day | 800 µl | 10 |
| 31 | L, F ~200, fusiform, Final 1.0x10$^8$, 200µl | p0521s | 0.38, 400µl (directly) | L1, 5%LB | 120 min | 1 day | 800 µl | 2 |
| 32 | L, F ~200, fusiform, Final 1.0x10$^8$, 200µl | p0521s | 0.38, 400µl (directly) | L1, 5%LB | 120 min | 1 day | 800 µl | 6 |
| 33 | L, F ~25, fusiform, Final 0.9x10$^8$, 100µl | p0521s | 0.40, 50µl (directly) | L1, 5%LB | 120 min | 1 day | 800 µl | 0 |
| 34 | L, F ~25, fusiform, Final 0.9x10$^8$, 100µl | p0521s | 0.40, 100µl (directly) | L1, 5%LB | 120 min | 1 day | 800 µl | 2 |
| 35 | L, F ~25, fusiform, Final 0.9x10$^8$, 100µl | p0521s | 0.40, 150µl (directly) | L1, 5%LB | 120 min | 1 day | 800 µl | 1 |
| 36 | L, F ~25, fusiform, Final 0.9x10$^8$, 100µl | p0521s | 0.40, 200µl (directly) | L1, 5%LB | 120 min | 1 day | 800 µl | 3 |
| 37 | L, F ~25, fusiform, Final 0.9x10$^8$, 200µl | p0521s | 0.40, 50µl (directly) | L1, 5%LB | 120 min | 1 day | 800 µl | 1 |
| 38 | L, F ~25, fusiform, Final 0.9x10$^8$, 200µl | p0521s | 0.40, 100µl (directly) | L1, 5%LB | 120 min | 1 day | 800 µl | 2 |
| 39 | L, F ~25, fusiform, Final 0.9x10$^8$, 200µl | p0521s | 0.40, 150µl (directly) | L1, 5%LB | 120 min | 1 day | 800 µl | 3 |
| 40 | L, F ~25, fusiform, Final 0.9x10$^8$, 200µl | p0521s | 0.40, 200µl (directly) | L1, 5%LB | 120 min | 1 day | 800 µl | 5 |

FIG. 1C

| Exp # | P. tricornutum culture characteristics: Cell culture (L = liquid, P = plates), F = chlorophyll A autofluorescence (for liquid cultures only), Cell morphotype (fusiform, ovoid, triradiate), Final concentration of cells, Amount used | Cargo Plasmid used | E. coli culture $OD_{600}$, amount used in conjugation reaction, used directly or concentrated in SOC media | Initial plates during conjug-ation | Time at 30°C for conjug-ation | Time at 18°C after 30°C and before selection | How much scraped cells was plated on selection plates | Number of ex-conjugant colonies (after 14 days or more) |
|---|---|---|---|---|---|---|---|---|
| 41 | L, F ~25, fusiform, Final $1.8 \times 10^8$, 200µl | p0521s | 1.05, 200µl -25mL LB into 1 ml SOC | L1, 5%LB | 90 min | 1 day | 800 µl | 73 |
| 42 | L, F ~25, fusiform, Final $1.8 \times 10^8$, 200µl | p0521s | 1.05, 200µl -25mL LB into 1 ml SOC | L1, 5%LB | 90 min | 1 day | 800 µl | 109 |
| 43 | L, F ~25, fusiform, Final $1.8 \times 10^8$, 200µl | p0521s | 0.88, 200µl -25mL LB into 1 ml SOC | L1, 5%LB | 90 min | 1 day | 800 µl | 74 |
| 44 | L, F ~25, fusiform, Final $1.8 \times 10^8$, 200µl | p0521s | 0.88, 200µl -25mL LB into 1 ml SOC | L1, 5%LB | 90 min | 1 day | 800 µl | 86 |
| 45 | L, F ~25, fusiform, Final $1.8 \times 10^8$, 200µl | p0521s | 0.68, 200µl -25mL LB into 1 ml SOC | L1, 5%LB | 90 min | 1 day | 800 µl | 42 |
| 46 | L, F ~25, fusiform, Final $1.8 \times 10^8$, 200µl | p0521s | 0.68, 200µl -25mL LB into 1 ml SOC | L1, 5%LB | 90 min | 1 day | 800 µl | 75 |
| 47 | L, F ~25, fusiform, Final $1.8 \times 10^8$, 200µl | p0521s | 0.47, 200µl -25mL LB into 1 ml SOC | L1, 5%LB | 90 min | 1 day | 800 µl | 57 |
| 48 | L, F ~25, fusiform, Final $1.8 \times 10^8$, 200µl | p0521s | 0.47, 200µl -25mL LB into 1 ml SOC | L1, 5%LB | 90 min | 1 day | 800 µl | 41 |
| 49 | L, F ~25, fusiform, Final $1.8 \times 10^8$, 200µl | p0521s | 0.20, 200µl -25mL LB into 1 ml SOC | L1, 5%LB | 90 min | 1 day | 800 µl | 47 |
| 50 | L, F ~25, fusiform, Final $1.8 \times 10^8$, 200µl | p0521s | 0.20, 200µl -25mL LB into 1 ml SOC | L1, 5%LB | 90 min | 1 day | 800 µl | 42 |
| 51 | P, fusiform, 20% oval or in transition to oval, Final $2.0 \times 10^8$, 200µl | p0521s | 0.58, 200µl -90 mL LB into 1.8 mL SOC | L1 | 90 min | 1 day | 400 µl | 11 |
| 52 | P, fusiform, 20% oval or in transition to oval, Final $2.0 \times 10^8$, 200µl | p0521s | 0.58, 200µl -90 mL LB into 1.8 mL SOC | L1 | 90 min | 1 day | 400 µl | 12 |
| 53 | P, fusiform, 20% oval or in transition to oval, Final $2.0 \times 10^8$, 200µl | p0521s | 0.58, 200µl -90 mL LB into 3.6 mL SOC | L1 | 90 min | 1 day | 400 µl | 28 |

FIG. 1D

| Exp # | P. tricornutum culture characteristics: Cell culture (L = liquid, P = plates), F = chlorophyll A autofluorescence (for liquid cultures only), Cell morphotype (fusiform, ovoid, triradiate), Final concentration of cells, Amount used | Cargo Plasmid used | E. coli culture OD$_{600}$ amount used in conjugation reaction, used directly or concentrated in SOC media | Initial plates during conjug-ation | Time at 30°C for conjug-ation | Time at 18°C after 30°C and before selection | How much scraped cells was plated on selection plates | Number of ex-conjugant colonies (after 14 days or more) |
|---|---|---|---|---|---|---|---|---|
| 54 | P, fusiform, 20% oval or in transition to oval, Final 2.0 x10$^8$, 200µl | p0521s | 0.58, 200µl -90 mL LB into 3.6 mL SOC | L1 | 90 min | 1 day | 400 µl | 6 |
| 55 | P, fusiform, 20% oval or in transition to oval, Final 2.0 x10$^8$, 200µl | p0521s | 0.58, 200µl -90 mL LB into 1.8 mL SOC | L1, 5%LB | 90 min | 1 day | 400 µl | 52 |
| 56 | P, fusiform, 20% oval or in transition to oval, Final 2.0 x10$^8$, 200µl | p0521s | 0.58, 200µl -90 mL LB into 1.8 mL SOC | L1, 5%LB | 90 min | 1 day | 400 µl | 42 |
| 57 | P, fusiform, 20% oval or in transition to oval, Final 2.0 x10$^8$, 200µl | p0521s | 0.58, 200µl -90 mL LB into 3.6 mL SOC | L1, 5%LB | 90 min | 1 day | 400 µl | 106 |
| 58 | P, fusiform, 20% oval or in transition to oval, Final 2.0 x10$^8$, 200µl | p0521s | 0.58, 200µl -90 mL LB into 3.6 mL SOC | L1, 5%LB | 90 min | 1 day | 400 µl | 103 |
| 59 | P, fusiform, 20% oval or in transition to oval, Final 2.0 x10$^8$, 200µl | p0521s | 0.58, 200µl -90 mL LB into 1.8 mL SOC | L1, 10%LB | 90 min | 1 day | 400 µl | 33 |
| 60 | P, fusiform, 20% oval or in transition to oval, Final 2.0 x10$^8$, 200µl | p0521s | 0.58, 200µl -90 mL LB into 1.8 mL SOC | L1, 10%LB | 90 min | 1 day | 400 µl | 30 |
| 61 | P, fusiform, 20% oval or in transition to oval, Final 2.0 x10$^8$, 200µl | p0521s | 0.58, 200µl -90 mL LB into 3.6 mL SOC | L1, 10%LB | 90 min | 1 day | 400 µl | 43 |
| 62 | P, fusiform, 20% oval or in transition to oval, Final 2.0 x10$^8$, 200µl | p0521s | 0.58, 200µl -90 mL LB into 3.6 mL SOC | L1, 10%LB | 90 min | 1 day | 400 µl | 49 |
| 63 | P, fusiform, 20% oval or in transition to oval, Final 2.0 x10$^8$, 200µl | p0521s | 0.58, 200µl -90 mL LB into 1.8 mL SOC | L1, 20%LB | 90 min | 1 day | 400 µl | 51 |
| 64 | P, fusiform, 20% oval or in transition to oval, Final 2.0 x10$^8$, 200µl | p0521s | 0.58, 200µl -90 mL LB into 1.8 mL SOC | L1, 20%LB | 90 min | 1 day | 400 µl | 90 |
| 65 | P, fusiform, 20% oval or in transition to oval, Final 2.0 x10$^8$, 200µl | p0521s | 0.58, 200µl -90 mL LB into 3.6 mL SOC | L1, 20%LB | 90 min | 1 day | 400 µl | 52 |
| 66 | P, fusiform, 20% oval or in transition to oval, Final 2.0 x10$^8$, 200µl | p0521s | 0.58, 200µl -90 mL LB into 3.6 mL SOC | L1, 20%LB | 90 min | 1 day | 400 µl | 46 |

FIG. 1E

| Exp # | P. tricornutum culture characteristics: Cell culture (L = liquid, P = plates), F = chlorophyll A autofluorescence (for liquid cultures only), Cell morphotype (fusiform, ovoid, triradiate), Final concentration of cells, Amount used | Cargo Plasmid used | E. coli culture OD$_{600}$, amount used in conjugation reaction, used directly or concentrated in SOC media | Initial plates during conjug-ation | Time at 30°C for conjug-ation | Time at 18°C after 30 °C and before selection | How much scraped cells was plated on selection plates | Number of ex-conjugant colonies (after 14 days or more) |
|---|---|---|---|---|---|---|---|---|
| 67 | P, fusiform, 20% oval or in transition to oval, Final 6.0 x10$^8$, 200µl | p0521s | 0.58, 50µl -90 mL LB into 3.6 mL SOC | L1, 5%LB | 90 min | 1 day | 400 µl | 4 |
| 68 | P, fusiform, 20% oval or in transition to oval, Final 5.0 x10$^8$, 200µl | p0521s | 0.58, 50µl -90 mL LB into 3.6 mL SOC | L1, 5%LB | 90 min | 1 day | 400 µl | 0 |
| 69 | P, fusiform, 20% oval or in transition to oval, Final 4.0 x10$^8$, 200µl | p0521s | 0.58, 50µl -90 mL LB into 3.6 mL SOC | L1, 5%LB | 90 min | 1 day | 400 µl | 0 |
| 70 | P, fusiform, 20% oval or in transition to oval, Final 3.0 x10$^8$, 200µl | p0521s | 0.58, 50µl -90 mL LB into 3.6 mL SOC | L1, 5%LB | 90 min | 1 day | 400 µl | 0 |
| 71 | P, fusiform, 20% oval or in transition to oval, Final 2.0 x10$^8$, 200µl | p0521s | 0.58, 50µl -90 mL LB into 3.6 mL SOC | L1, 5%LB | 90 min | 1 day | 400 µl | 1 |
| 72 | P, fusiform, 20% oval or in transition to oval, Final 2.0 x10$^8$, 100µl | p0521s | 0.52, 100µl, 200 ml LB into 6 mL SOC | L1, 5%LB | 90 min | 1 day | 400 µl | 112 |
| 73 | P, fusiform, 20% oval or in transition to oval, Final 2.0 x10$^8$, 100µl | p0521s | 0.52, 100µl, 200 ml LB into 6 mL SOC | L1, 10%LB | 90 min | 1 day | 400 µl | 38 |
| 74 | P, fusiform, 20% oval or in transition to oval, Final 2.0 x10$^8$, 100µl | p0521s | 0.52, 100µl, 200 ml LB into 6 mL SOC | L1, 20%LB | 90 min | 1 day | 400 µl | 53 |
| 75 | P, fusiform, 20% oval or in transition to oval, Final 2.0 x10$^8$, 100µl | p0521s | 0.52, 200µl, 200 ml LB into 6 mL SOC | L1, 5%LB | 90 min | 1 day | 400 µl | 145 |
| 76 | P, fusiform, 20% oval or in transition to oval, Final 2.0 x10$^8$, 100µl | p0521s | 0.52, 200µl, 200 ml LB into 6 mL SOC | L1, 10%LB | 90 min | 1 day | 400 µl | 70 |

FIG. 1F

| Exp # | *P. tricornutum* culture characteristics: Cell culture (L = liquid, P = plates), F = chlorophyll A autofluorescence (for liquid cultures only), Cell morphotype (fusiform, ovoid, triradiate), Final concentration of cells, Amount used | Cargo Plasmid used | *E. coli* culture $OD_{600}$, amount used in conjugation reaction, used directly or concentrated in SOC media | Initial plates during conjug-ation | Time at 30°C for conjug-ation | Time at 18°C after 30 °C and before selection | How much scraped cells was plated on selection plates | Number of ex-conjugant colonies (after 14 days or more) |
|---|---|---|---|---|---|---|---|---|
| 77 | P, fusiform, 20% oval or in transition to oval, Final 2.0 x10⁸, 100µl | p0521s | 0.52, 200µl, 200 mL LB into 6 mL SOC | L1, 20%LB | 90 min | 1 day | 400 µl | 46 |
| 78 | P, fusiform, 20% oval or in transition to oval, Final 2.0 x10⁸, 200µl | p0521s | 0.52, 100µl, 200 mL LB into 6 mL SOC | L1, 5%LB | 90 min | 1 day | 400 µl | 203 |
| 79 | P, fusiform, 20% oval or in transition to oval, Final 2.0 x10⁸, 200µl | p0521s | 0.52, 100µl, 200 mL LB into 6 mL SOC | L1, 10%LB | 90 min | 1 day | 400 µl | 57 |
| 80 | P, fusiform, 20% oval or in transition to oval, Final 2.0 x10⁸, 200µl | p0521s | 0.52, 100µl, 200 mL LB into 6 mL SOC | L1, 20%LB | 90 min | 1 day | 400 µl | 106 |
| 81 | P, fusiform, 20% oval or in transition to oval, Final 2.0 x10⁸, 200µl | p0521s | 0.52, 200µl, 200 mL LB into 6 mL SOC | L1, 5%LB | 90 min | 1 day | 400 µl | 332 |
| 82 | P, fusiform, 20% oval or in transition to oval, Final 2.0 x10⁸, 200µl | p0521s | 0.52, 200µl, 200 mL LB into 6 mL SOC | L1, 10%LB | 90 min | 1 day | 400 µl | 260 |
| 83 | P, fusiform, 20% oval or in transition to oval, Final 2.0 x10⁸, 200µl | p0521s | 0.52, 200µl, 200 mL LB into 6 mL SOC | L1, 20%LB | 90 min | 1 day | 400 µl | 121 |
| 84 | P, fusiform, 20% oval or in transition to oval, Final 4.0 x10⁸, 100µl | p0521s | 0.52, 100µl, 200 mL LB into 6 mL SOC | L1, 5%LB | 90 min | 1 day | 400 µl | 169 |
| 85 | P, fusiform, 20% oval or in transition to oval, Final 4.0 x10⁸, 100µl | p0521s | 0.52, 100µl, 200 mL LB into 6 mL SOC | L1, 10%LB | 90 min | 1 day | 400 µl | 210 |

FIG. 1G

| Exp # | P. tricornutum culture characteristics: Cell culture (L = liquid, P = plates), F = chlorophyll A autofluorescence (for liquid cultures only), Cell morphotype (fusiform, ovoid, triradiate), Final concentration of cells, Amount used | Cargo Plasmid used | E. coli culture OD$_{600}$, amount used in conjugation reaction, used directly or concentrated in SOC media | Initial plates during conjug-ation | Time at 30°C for conjug-ation | Time at 18°C after 30°C and before selection | How much scraped cells was plated on selection plates | Number of ex-conjugant colonies (after 14 days or more) |
|---|---|---|---|---|---|---|---|---|
| 86 | P, fusiform, 20% oval or in transition to oval, Final 4.0 x10$^8$, 100µl | p0521s | 0.52, 100µl, 200 mL LB into 6 mL SOC | L1, 20%LB | 90 min | 1 day | 400 µl | 111 |
| 87 | P, fusiform, 20% oval or in transition to oval, Final 4.0 x10$^8$, 100µl | p0521s | 0.52, 200µl, 200 mL LB into 6 mL SOC | L1, 5%LB | 90 min | 1 day | 400 µl | 311 |
| 88 | P, fusiform, 20% oval or in transition to oval, Final 4.0 x10$^8$, 100µl | p0521s | 0.52, 200µl, 200 mL LB into 6 mL SOC | L1, 10%LB | 90 min | 1 day | 400 µl | 215 |
| 89 | P, fusiform, 20% oval or in transition to oval, Final 4.0 x10$^8$, 100µl | p0521s | 0.52, 200µl, 200 mL LB into 6 mL SOC | L1, 20%LB | 90 min | 1 day | 400 µl | 117 |
| 90 | P, fusiform, 20% oval or in transition to oval, Final 4.0 x10$^8$, 200µl | p0521s | 0.52, 200µl, 200 mL LB into 6 mL SOC | L1, 5%LB | 90 min | 1 day | 400 µl | 247 |
| 91 | P, fusiform, 20% oval or in transition to oval, Final 4.0 x10$^8$, 200µl | p0521s | 0.52, 100µl, 200 mL LB into 6 mL SOC | L1, 10%LB | 90 min | 1 day | 400 µl | 280 |
| 92 | P, fusiform, 20% oval or in transition to oval, Final 4.0 x10$^8$, 200µl | p0521s | 0.52, 100µl, 200 mL LB into 6 mL SOC | L1, 20%LB | 90 min | 1 day | 400 µl | 211 |
| 93 | P, fusiform, 20% oval or in transition to oval, Final 4.0 x10$^8$, 200µl | p0521s | 0.52, 200µl, 200 mL LB into 6 mL SOC | L1, 5%LB | 90 min | 1 day | 400 µl | 460 |
| 94 | P, fusiform, 20% oval or in transition to oval, Final 4.0 x10$^8$, 200µl | p0521s | 0.52, 200µl, 200 mL LB into 6 mL SOC | L1, 10%LB | 90 min | 1 day | 400 µl | 450 |

FIG. 1H

| Exp # | P. tricornutum culture characteristics: Cell culture (L = liquid, P = plates), F = chlorophyll A autofluorescence (for liquid cultures only), Cell morphotype (fusiform, ovoid, triradiate), Final concentration of cells, Amount used | Cargo Plasmid used | E. coli culture OD$_{600}$, amount used in conjugation reaction, used directly or concentrated in SOC media | Initial plates during conjug-ation | Time at 30°C for conjug-ation | Time at 18°C after 30 °C and before selection | How much scraped cells was plated on selection plates | Number of ex-conjugant colonies (after 14 days or more) |
|---|---|---|---|---|---|---|---|---|
| 95 | P, fusiform, 20% oval or in transition to oval, Final 4.0 x10$^8$, 200μl | p0521s | 0.52, 200μl, 200 mL LB into 6 mL SOC | L1, 20%LB | 90 min | 1 day | 400 μl | 263 |
| 96 | P, fusiform, 20% oval or in transition to oval, Final 6.0 x10$^8$, 100μl | p0521s | 0.52, 100μl, 200 mL LB into 6 mL SOC | L1, 5%LB | 90 min | 1 day | 400 μl | 226 |
| 97 | P, fusiform, 20% oval or in transition to oval, Final 6.0 x10$^8$, 100μl | p0521s | 0.52, 100μl, 200 mL LB into 6 mL SOC | L1, 10%LB | 90 min | 1 day | 400 μl | 226 |
| 98 | P, fusiform, 20% oval or in transition to oval, Final 6.0 x10$^8$, 100μl | p0521s | 0.52, 100μl, 200 mL LB into 6 mL SOC | L1, 20%LB | 90 min | 1 day | 400 μl | 173 |
| 99 | P, fusiform, 20% oval or in transition to oval, Final 6.0 x10$^8$, 100μl | p0521s | 0.52, 200μl, 200 mL LB into 6 mL SOC | L1, 5%LB | 90 min | 1 day | 400 μl | 532 |
| 100 | P, fusiform, 20% oval or in transition to oval, Final 6.0 x10$^8$, 100μl | p0521s | 0.52, 200μl, 200 mL LB into 6 mL SOC | L1, 10%LB | 90 min | 1 day | 400 μl | 385 |
| 101 | P, fusiform, 20% oval or in transition to oval, Final 6.0 x10$^8$, 100μl | p0521s | 0.52, 200μl, 200 mL LB into 6 mL SOC | L1, 20%LB | 90 min | 1 day | 400 μl | 234 |
| 102 | P, fusiform, 20% oval or in transition to oval, Final 6.0 x10$^8$, 200μl | p0521s | 0.52, 100μl, 200 mL LB into 6 mL SOC | L1, 5%LB | 90 min | 1 day | 400 μl | 232 |
| 103 | P, fusiform, 20% oval or in transition to oval, Final 6.0 x10$^8$, 200μl | p0521s | 0.52, 100μl, 200 mL LB into 6 mL SOC | L1, 10%LB | 90 min | 1 day | 400 μl | 238 |

FIG. 11

| Exp # | P. tricornutum culture characteristics: Cell culture (L = liquid, P = plates), F = chlorophyll A autofluorescence (for liquid cultures only), Cell morphotype (fusiform, ovoid, triradiate), Final concentration of cells, Amount used | Cargo Plasmid used | E. coli culture OD$_{600}$, amount used in conjugation reaction, used directly or concentrated in SOC media | Initial plates during conjug-ation | Time at 30°C for conjug-ation | Time at 18°C after 30 °C and before selection | How much scraped cells was plated on selection plates | Number of ex-conjugant colonies (after 14 days or more) |
|---|---|---|---|---|---|---|---|---|
| 104 | P, fusiform, 20% oval or in transition to oval, Final 6.0 x10$^8$, 200μl | p0521s | 0.52, 100μl, 200 mL LB into 6 mL SOC | L1, 20%LB | 90 min | 1 day | 400 μl | 216 |
| 105 | P, fusiform, 20% oval or in transition to oval, Final 6.0 x10$^8$, 200μl | p0521s | 0.52, 200μl, 200 mL LB into 6 mL SOC | L1, 5%LB | 90 min | 1 day | 400 μl | 1100 |
| 106 | P, fusiform, 20% oval or in transition to oval, Final 6.0 x10$^8$, 200μl | p0521s | 0.52, 200μl, 200 mL LB into 6 mL SOC | L1, 10%LB | 90 min | 1 day | 400 μl | 618 |
| 107 | P, fusiform, 20% oval or in transition to oval, Final 6.0 x10$^8$, 200μl | p0521s | 0.52, 200μl, 200 mL LB into 6 mL SOC | L1, 20%LB | 90 min | 1 day | 400 μl | 458 |
| 108 | P, Final 5.8x10$^8$, 200μl | p0521s ΔR1 | 0.66, 200μl, 20 mL LB into 0.5 mL SOC | L1, 5%LB | 90 min | 2 days | 3x300 μl | 5660 |
| 109 | P, Final 5.8x10$^8$, 200μl | p0521s ΔR12 | 0.60, 200μl, 20 mL LB into 0.5 mL SOC | L1, 5%LB | 90 min | 2 days | 3x300 μl | 2894 |
| 110 | P, Final 5.8x10$^8$, 200μl | p0521s ΔR12 | 0.48, 200μl, 20 mL LB into 0.5 mL SOC | L1, 5%LB | 90 min | 2 days | 3x300 μl | 895 |
| 111 | P, Final 5.8x10$^8$, 200μl | p0521s ΔR2 | 0.54, 200μl, 20 mL LB into 0.5 mL SOC | L1, 5%LB | 90 min | 2 days | 3x300 μl | 2393 |
| 112 | P, Final 5.8x10$^8$, 200μl | p0521s ΔoriT | 0.60, 200μl, 20 mL LB into 0.5 mL SOC | L1, 5%LB | 90 min | 2 days | 3x300 μl | 0 |

FIG. 1J

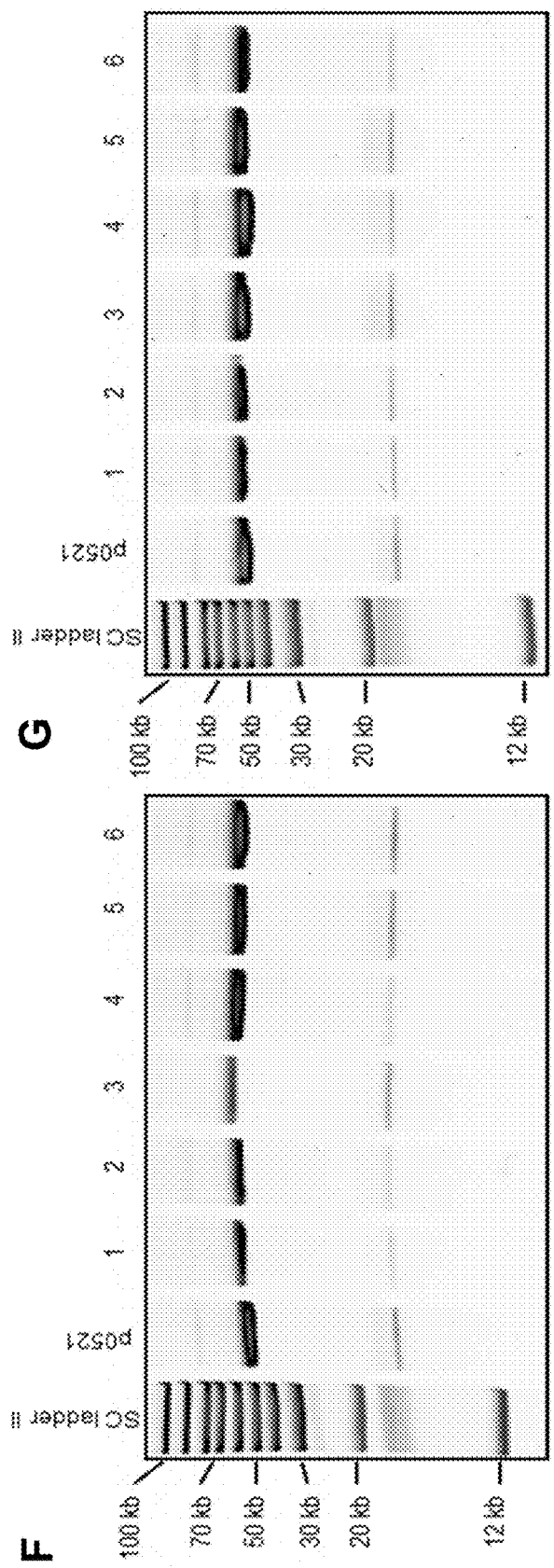

HIGH EFFICIENCY METHOD FOR ALGAL TRANSFORMATION

CROSS REFERENCE TO RELATED APPLICATIONS

This application claims benefit of priority under U.S.C. 119(e) to U.S. Provisional Patent Application No. 62/118,408, filed Feb. 19, 2015, the entire contents of which are herein incorporated by reference.

SEQUENCE LISTING

This application contains references to nucleic acid sequences and amino acid sequences which have been submitted concurrently herewith as the sequence SGI1860_1_Sequence_Listing.txt", file size 51 kilobytes (kb), created on Feb. 18, 2016, which is incorporated by reference in its entirety pursuant to 37 C.F.R. 1.52(e) (iii)(5).

BACKGROUND OF THE INVENTION

The present invention relates to generally to genetic engineering of algal and heterokont cells and more specifically to producing recombinant algal cells using bacterial conjugation.

Bacterial conjugation is a process by which genetic material is transferred from donor cells to recipient cells. The transfer of these genes requires complex protein machinery that ensures DNA mobilization and mating pair formation. Conjugation in Gram-negative bacteria is mediated by the Type IV secretion system (T4SS), a large macromolecular complex involved in substrate transport and pilus biogenesis. T4SSs are implicated not only in bacterial conjugation, but also in the secretion of virulence factors to eukaryotic cells. Many effectors secreted by T4SS are virulence factors involved in pathogenic diseases, such as brucellosis, whooping cough, cat scratch disease, pneumonia, or gastric ulcer, caused by bacterial infection with *Brucella suis, Bordella pertussis, Bartonella henselea, Legionella pneumonia* or *Helicobacter pylori*, respectively. Further, bacterial conjugation is one of the main mechanisms whereby bacteria become resistant to antibiotics.

Genes encoding the transfer function (including mobilization (MOB) genes and mating pair formation (MPF) genes can be present on an autonomous replicating plasmid (the "conjugative plasmid" or "mobilization plasmid") or may be integrated into the genome of a bacterial transfer host. These genes that enable transfer of DNA from the host are found in two separate tra gene clusters in *E. coli*. Genes to be transferred into the recipient cell can be present on a conjugative plasmid that includes the genes encoding the DNA transfer functions, or can be present on a separate episome that may be referred to as a "DNA transfer construct", "transfer construct" or "transfer plasmid" (sometimes referred to as a "cargo plasmid"). The transfer construct/cargo plasmid includes, in addition to one or more genes to be transferred into a recipient cell, an origin of transfer (oriT) that includes a sequence recognized by a "relaxase" that is encoded by a mobilization gene.

There are many examples of bacterial conjugation documented in the art. Christie et al. reviews T4SS conjugation systems from data derived from a variety of bacteria, including *Agrobacterium tumefaciens, Bordetella pertussis, Helicobacter pylori* and *Legionella pneumonia* (Christie *Mol Microbiol* (2001) 40(2):294). Schroder et al. showed that type IV secretion system (T4SS) dependent DNA transfer into host cells may occur naturally during human infection with *Bartonella* (Schroder et al. *PNAS* (2011) 108(35): 14643). Cabezon et al. provide a detailed review of bacterial conjugation and the proteins involved (Cabezon et al. *FEMS Microbiol Reviews* (2015) 39:81). In a review, Lawley et al. describe that F factor conjugation is a true T4SS in *E. coli* (Lawley et al. *FEMS Microbiol Letters* (2003) 224:1). Stucken et al. describe the transformation of the (prokaryotic) cyanobacterial species *Fischerella* and *Chlorogleopsis* by conjugation, electroporation and biolostic DNA transfer methods (Stucken et al. *Curr Microbiol* (2013) 65:552). Anand et al. describe genetic transformation of plants by the bacterium *Agrobacterium tumefaciens*, which is a plant parasite (Anand et al. *New Phytologist* (2012) 195:203). Fitzpatrick reviews conjugation in fungi (Fitzpatrick *FEMS Microbiol Letters* (2012) 329:1). Conjugation resulting in transfer of DNA from a bacterium into a diatom has not been described, and conjugation from a non-Rhizhobial bacterium into a eukaryotic microalga has also not been described.

Diatoms are eukaryotic phytoplankton that contribute a significant fraction of global primary productivity and demonstrate great potential for autotrophic bioproduction of fuels and higher value chemicals. A unique feature of diatoms (which are classified as microalgae and are also heterokonts) is that they are encased in a silca cell wall called a frustule. Although methods for genetic manipulation currently exist for some diatom species, they are slow compared to the efficient methods available for other model microbes such as *E. coli* and yeast, and this has stymied both basic diatom research and applied strain development. To accelerate research in ecologically and biotechnologically important microalgae, improved transformation methods and episomal vectors were developed.

Episomes can provide a reliable, consistent and predictable platform for protein expression by avoiding the complications of random chromosomal integration that include multiple insertions, position-specific effects on expression, and potential knock-out of non-targeted genes. Consistent protein expression from episomes can also allow for efficient complementation of mutants to confirm gene function. Circular DNA molecules have been previously isolated from diatoms, but they have never been successfully reintroduced as episomes.

Nucleic acid molecules such as episomes can be efficiently moved among bacteria and even between bacteria and eukaryotes via conjugation. To date, cells such as plant and algae cells that have highly structured cell walls have been reported to be transformed by conjugation only by *Agrobacterium* species (of the family Rhizobiaceae) which are naturally pathogenic to plants. During infection of plant cells by an *Agrobacterium* species, DNA is transferred from an *Agrobacterium* donor cell and is integrated into the recipient host genome.

SUMMARY OF THE INVENTION

The present invention relates to the discovery of a highly efficient method of transforming algal cells. Specifically, the invention relates to a novel method of delivering a nucleic acid molecule directly to eukaryotic algal cells or heterokont cells by bacterial conjugation. A method for transforming eukaryotic algal cells, especially diatoms and green algae, by a conjugation method which directly transfers DNA from non-Rhizobiaceae bacteria such as *E. coli* to the algal cells has not been described. Further, methods of transferring nucleic acid molecules from bacteria to algae such that they are maintained as stable episomes has not been described.

Herein are described methods for DNA transfer to eukaryotic algal cells and heterokont cells. Additionally, constructs for conjugative transfer into algae and heterokonts are provided that include sequences that support episomal replication and stability in algal and heterokont cells. For example, the transferred DNA can remain episomal in the algal or heterokont cell through multiple generations. These novel tools and methods compose an efficient and high throughput system for algal genetic manipulation.

In a first aspect, the present invention provides a method of delivering a nucleic acid molecule to an algal cell comprising: contacting the alga or heterokont cell with a bacterium comprising a DNA transfer construct comprising the nucleic acid molecule, where the bacterium is not a species of Rhizobiaceae, wherein the nucleic acid molecule is delivered to the algal cell. An algal recipient cell can be a eukaryotic microalga, for example, a member of the green algae (chlorophytes), red algae (rhodophytes), diatoms (bacillariophytes), pelagophytes, prasinophytes, glaucophytes, chlorarachniophytes, euglenophytes, chromophytes, xanthophytes, or dinoflagellates. In some examples, an algal recipient is a member of the green algae (chlorophytes), a eustigmatophyte alga, or a diatom (bacillariophyte). Alternatively or in addition, an algal cell can be a member of any of the genera *Amphora, Ankistrodesmus, Asteromonas, Aureococcus, Boekelovia, Bolidomonas, Borodinella, Botrydium, Botryococcus, Bracteacoccus, Carteria, Chaetoceros, Chlamydomonas, Chlorella, Chlorococcum, Chlorogonium, Chrococcidiopsis, Chroomonas, Chrysophyceae, Chrysosphaera, Coscinodiscus, Cricosphaera, Crypthecodinium, Cryptococcus, Cryptomonas, Cyanidioschyzon, Cyclotella, Cylindrotheca, Cymbella, Desmodesmus, Dunaliella, Elina, Elhpsoidon, Emiliania, Eremosphaera, Ernodesmius, Euglena, Eustigmatos, Fragilaria, Fragilariopsis, Franceia, Gloeothamnion, Haematococcus, Hantzschia, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phaeodactylum, Picochlorum, Platymonas, Pleurochrysis, Pleurococcus, Porphyridium, Prototheca, Pseudochlorella, Pseudoneochloris, Pseudostaurastrum, Pyramimonas, Pyrobotrys, Rholdella, Scenedesmus, Schizochlamydella, Skeletonema, Spirulina, Spyrogyra, Staurastrum, Stichococcus, Tetrachlorella, Tetraselmis, Thalassiosira, Tribonema, Vaucheria, Viridiella, Vischeria,* or *Volvox*. For example, diatoms that may be used include without limitation *Achnanthes, Amphora, Chaetoceros, Coscinodiscus, Cylindrotheca, Cyclotella, Cymbella, Fragilaria, Fragilariopsis, Hantzschia, Navicula, Nitzschia, Pavlova, Pseudo-Nitzschia, Phaeodactylum, Psammodictyon, Skeletonema, Thalassionema,* and *Thalassiosira*. In some examples, the algal cell is a species of *Cyclotella, Cylindrotheca, Phaeodactylum,* or *Thalassiosira*. Chlorophyte microalgae that can be used for genetic modification using the methods disclosed herein, include, for example, species of *Botryococcus, Chlamydomonas, Chlorella, Desmodesmus, Dunaliella, Elipsoidon, Haematococcus, Micromonas, Nannochloris, Ostreococcus, Parachlorella, Pseudochlorella, Scendedesmus, Tetrachlorella, Tetraselmis,* and *Vovlox*. In some examples, an algal recipient can be a species of *Chlamydomonas, Chlorella, Desmodesmus, Haematococcus, Parachlorella,* or *Tetraselmis*. Eustigmatophytes that may be used in the methods provided herein include, without limitation, *Ellipsoidon, Eustigmatos, Monodus, Nannochloropsis, Pseudostaurastrum,* and *Vischeria*. Additional examples of recipient cells include heterokont microorganisms such as Labyrinthulomycetes. For example, a heterokont cell used in the methods can be a species of a genus selected from the group consisting of: *Aplanochytrium, Aurantiochytrium, Diplophrys, Japonochytrium, Oblongichytrium, Schizochytrium, Thraustochytrium,* or *Ulkenia*.

The bacterial donor cell can be any bacterial cell that has conjugative capability, e.g., any bacterial cell that includes genes encoding the necessary conjugative functions, which may be native genes or may be genes that have been introduced into the conjugative donor cell. The bacterial donor cell can be of a species of gram negative or gram positive bacteria. For example, the donor bacterium can be a species of *Bacillus, Escherichia, Clostridium, Pseudomonas,* or *Streptomyces*. In some examples is not a species belonging to the Rhizobiaceae. In some examples, the bacterial cell used to transfer DNA into an algal cell is *Escherichia coli*.

A DNA transfer construct used to transform an algal or heterokont host includes an origin of transfer and preferably a selectable marker or detectable marker. In some examples, a DNA transfer construct used in the conjugation methods provided herein includes an origin of transfer and further includes one or both of an autonomous replication sequence (ARS) and a centromere sequence, and can optionally further include a detectable marker or a selectable marker that allows for selection based on the presence of the DNA transfer construct (or a portion thereof) in the intended recipient cell. In some examples, the DNA transfer construct that is transferred into an algal cell becomes established as an episomal molecule in the algal recipient, and in some examples the episomal molecule can be stable in the algal cell line for at least 5, at least 10, at least 15, at least 20, at least 25, or at least 30 generations in the presence or absence of selection.

In some examples, the DNA transfer construct is a plasmid that comprises an origin of transfer, a maintenance cassette, and optionally a selectable marker. The maintenance cassette allows for replication of the DNA transfer construct in a recipient host, for example, for at least five, ten, fifteen, twenty, twenty-five, or thirty generations in the presence or absence of selection. In some examples, the maintenance cassette comprises sequences having a GC content less than that of the intended recipient microorganism. In some examples, the maintenance cassette comprises sequences having a GC content of less than 50%, less than about 40%, or less than or equal to about 30%. Alternatively or in addition, a maintenance cassette can include a centromere sequence and/or an ARS. In some examples, the maintenance cassette is a yeast maintenance cassette that includes one or both of an ARS or centromere sequence derived from a yeast species (for example, a species of *Saccharomyces* or *Candida*), such as a *Saccharomyces* species.

In additional examples, an ARS sequence present on the maintenance cassette may be, for example, from a plant, fungus, alga, or heterokont, or may be a synthetic sequence that can function as an ARS. The ARS may be a yeast ARS, e.g., a *Saccharomyces* ARS or a sequence derived therefrom. For example, the ARS can be *S. cerevisiae* ARSH4 (SEQ ID NO:2) or a nucleic acid sequence having at least 80%, at least 85%, at least 90%, at least 95%, or at least 98% identity thereto.

A centromere sequence of a maintenance cassette can be a sequence of any eukaryotic genome (or a sequence at least 80% identical thereto) identified as a centromere or portion thereof. The centromere sequence may be a yeast centromere sequence, e.g., a *Saccharomyces* centromere sequence or a sequence derived therefrom. For example, the centromere sequence can be *S. cerevisiae* CEN6 (SEQ ID NO:3) or a nucleic acid sequence having at least 80%, at least 85%, at least 90%, at least 95%, or at least 98% identity thereto. In some examples, the maintenance cassette comprises CEN6-ARSH4 (SEQ ID NO:4), or a sequence having at least 80%, at least 85%, at least 90%, at least 95%, or at least 98% identity thereto. In another specific aspect, the maintenance cassette comprises CEN6-ARSH4-HIS3 (SEQ ID NO:5) or a sequence having at least 80%, at least 85%, at least 90%, at least 95%, or at least 98% identity thereto.

A selectable marker used in a may be an antibiotic resistance gene, a gene encoding a polypeptide conferring resistance to a toxin, an auxotrophic marker, and a combination thereof. In some aspects, the antibiotic resistance gene confers resistance to antibiotics including, without limitation, blasticidin, bleomycin, gentamycin, glyphosate, hygromycin, kanamycin, neomycin, nourseothricin, phleomycin, puromycin, spectinomycin, zeocin, and streptomycin. In a further aspect, the plasmid further comprises a promoter, a reporter gene, a regulatory element or a combination thereof. In one aspect, the transformation efficiency is increased at least about 100-fold using a DNA transfer construct that includes a maintenance cassette as compared to transforming with a plasmid without a maintenance cassette. In some examples, the DNA transfer construct is maintained as a replicating extra-chromosomal vector in the algal cell.

In various examples, a DNA transfer construct includes a nucleic acid molecule that includes at least one gene encoding a functional RNA or polypeptide. A functional RNA can be, for example, an antisense RNA, an siRNA (RNAi construct), an sh (short hairpin) RNA, a micro-RNA, a ribozyme, a tracr RNAs, a crRNA, or a chimeric guide RNA. A polypeptide encoded by the nucleic acid molecules can be as nonlimiting examples, a metabolic enzyme, a growth regulator, a transcription factor, a transcriptional activator, a polymerase, a nuclease, a transposase, a recombinase, an RNA binding protein, a component of a spliceosome or ribosome, a structural protein, an antibody or a subunit thereof, a cytoskeletal protein, a transporter, an ion channel, a receptor, a chaperonin, a kinase, a phosphodiesterase, a nucleotide cyclase, or a photosynthetic protein. In an additional aspect, the nucleic acid molecule encodes at least two genes or at least three genes. In various examples, the DNA transfer construct is at least about 1 kb, 10 kb, 25 kb, 50 kb, 75 kb, 100 kb, 125 kb, 150 kb, 175 kb, 200 kb, 250 kb, 300 kb, 350 kb, 400 kb, 500 kb, 600 kb, 700 kb, 800 kb, 900 kb or 1 Mbp. In some examples, the DNA transfer construct is at least about 50 kb or at least about 100 kb in size.

In an additional aspect, the present invention provides a method of producing a recombinant algal cell comprising contacting the algal cell with a bacterium that comprises a DNA transfer construct comprising a nucleic acid molecule, wherein the plasmid becomes established in the algal host cell as an episome, thereby producing a recombinant algal cell. The algal cell can be a cell of any type of algae disclosed herein, for example, a member of the green algae (chlorophytes), red algae (rhodophytes), diatoms (bacillariophytes), pelagophytes, prasinophytes, glaucophytes, chlorarachniophytes, euglenophytes, chromophytes, xanthophytes, and dinoflagellates. For example, the algal cell can be a member of the green algae (chlorphytes) or diatoms (bacillariophytes). The algal recipient cell can be a member of the genera including *Amphora, Ankistrodesmus, Aplanochytrium, Asteromonas, Aureococcus, Boekelovia, Bolidomonas, Borodinella, Botrydium, Botryococcus, Bracteacoccus, Carteria, Chaetoceros, Chlamydomonas, Chlorella, Chlorococcum, Chlorogonium, Chrococcidiopsis, Chroomonas, Chrysophyceae, Chrysosphaera, Cricosphaera, Crypthecodinium, Cryptococcus, Cryptomonas, Cyanidioschyzon, Cyclotella, Cylindrotheca, Cymbella, Desmodesmus, Dunaliella, Elina, Elhpsoidon, Emiliania, Eremosphaera, Ernodesmius, Euglena, Eustigmatos, Fragilaria, Fragilariopsis, Franceia, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phaeodactylum, Picochlorum, Platymonas, Pleurochrysis, Pleurococcus, Porphyridium, Prototheca, Pseudochlorella, Pseudoneochloris, Pseudostaurastrum, Pyramimonas, Pyrobotrys, Rholdella, Scenedesmus, Schizochlamydella, Skeletonema, Spirulina, Spyrogyra, Staurastrum, Stichococcus, Tetrachlorella, Tetraselmis, Thalassiosira, Tribonema, Vaucheria, Vibrio, Viridiella, Vischeria*, or *Volvox*. For example, diatoms that may be used include *Achnanthes, Amphora, Chaetoceros, Coscinodiscus, Cylindrotheca, Cyclotella, Cymbella, Fragilaria, Fragilariopsis, Hantzschia, Navicula, Nitzschia, Pavlova, Pseudo-Nitzschia, Phaeodactylum, Psammodictyon, Skeletonema, Thalassionema*, and *Thalassiosira*. In some examples, the algal cell is a *Phaeodactylum* or *Thalassiosira* alga. Chlorophytes that can be used for genetic modification or nucleic acid isolation include, for example, species of *Botryococcus, Chlamydomonas, Chlorella, Desmodesmus, Dunaliella, Elipsoidon, Haematococcus, Micromonas, Nannochloris, Ostreococcus, Parachlorella, Pseudochlorella, Scendedesmus, Tetrachlorella, Tetraselmis*, and *Vovlox*. In some examples, an algal recipient can be a species of *Chlamydomonas, Chlorella, Desmodesmus, Haematococcus, Parachlorella*, or *Tetraselmis*. Eustigmatophytes that may be used in the methods provided herein include, without limitation, *Eustigmatos, Monodus, Nannochloropsis, Pseudostaurastrum*, and *Vischeria*.

The bacterial cell can be any bacterial cell that has conjugative capability, e.g., includes genes encoding the conjugative functions which may be native genes or may be genes introduced into the conjugative donor cell. The bacterial donor cell can be of a species of gram negative or gram positive bacteria, and can be, for example, a species of *Bacillus, Escherichia, Clostridium, Pseudomonas*, or *Streptomyces*. In some examples the bacterial transfer host is not a species of the Rhizobiaceae family. In an exemplary embodiment, the bacterial cell used to transfer DNA into an algal cell is *E. coli*.

The DNA transfer construct comprises an origin of transfer, a maintenance cassette, and optionally a selectable marker. In some examples, the maintenance cassette comprises sequences having a GC content less than that of the intended recipient microorganism. In some examples, the maintenance cassette comprises sequences having a GC content of less than 50%, less than about 40%, or less than or equal to about 30%. The maintenance cassette can be a yeast maintenance cassette, e.g., a maintenance cassette comprising sequences derived from a species of *Saccharo-*

*myces* or *Candida*, e.g., a yeast maintenance cassette can comprise an *S. cerevisiae* ARS and centromere sequence.

Alternatively or in addition, a maintenance cassette can include an ARS from a plant, fungus, alga, or heterokont, or may be a synthetic sequence that can function as an ARS. The ARS may be a *S. cerevisiae* ARS or a sequence derived therefrom. For example, the ARS can be ARSH4 (SEQ ID NO:2) or a nucleic acid sequence having at least 80%, at least 85%, at least 90%, at least 95%, or at least 98% identity thereto. The maintenance cassette can also include a centromere sequence that can be a sequence of any eukaryotic genome (or a sequence at least 80% identical thereto) that has sequence characteristics of a centromere, is located within the centromere region of a chromosome, or functions as a centromere. The centromere sequence may be a *S. cerevisiae* centromere sequence or a sequence derived therefrom. For example, the centromere sequence can be CEN6 (SEQ ID NO:3) or a nucleic acid sequence having at least 80%, at least 85%, at least 90%, at least 95%, or at least 98% identity thereto. In some examples, the maintenance cassette comprises CEN6-ARSH4 (SEQ ID NO:4), or a sequence having at least 80%, at least 85%, at least 90%, at least 95%, or at least 98% identity thereto. In another specific aspect, the maintenance cassette comprises CEN6-ARSH4-HIS3 (SEQ ID NO:5) or a sequence having at least 80%, at least 85%, at least 90%, at least 95%, or at least 98% identity thereto. In various aspects the maintenance cassette has a GC content lower than the GC content of the recipient alga or heterokont.

The DNA transfer construct can be at least about 1 kb, 10 kb, 25 kb, 50 kb, 75 kb, 100 kb, 125 kb, 150 kb, 175 kb, 200 kb, 250 kb, 300 kb, 350 kb, 400 kb, 500 kb, 600 kb, 700 kb, 800 kb, 900 kb or 1 Mbp in size. In some examples, the nucleic acid molecule is at least about 50 kb or at least about 100 kb. The DNA transfer construct can include a nucleic acid molecule that encodes a functional RNA or polypeptide. The DNA transfer construct can replicate autonomously in the recipient cell for at least 5, at least 10, at least 15, at least 20, at least 25, or at least 30 generations in the presence or absence of selection.

In a further aspect, methods are provided for transforming a diatom by bacterial conjugation. The method includes contacting a diatom with a bacterium that includes a DNA transfer construct comprising the nucleic acid molecule to deliver the nucleic acid molecule to the diatom. The diatom can be any species of diatom, including, without limitation, a species of a genus selected from the group consisting of *Achnanthes, Amphora, Chaetoceros, Coscinodiscus, Cylindrotheca, Cyclotella, Cymbella, Fragilaria, Fragilariopsis, Hantzschia, Navicula, Nitzschia, Pavlova, Pseudo-Nitzschia, Phaeodactylum, Psammodictyon, Skeletonema, Thalassionema*, and *Thalassiosira*. In some examples the diatom is a species of *Cylindrotheca, Cyclotella, Phaeodactylum*, or *Thalassiosira*. For example, the diatom can be *Phaeodactylum tricornutum* or a species of *Thalassiosira*. The bacteria used for conjugative transfer can be any species of bacteria that includes the mobilization functions, including, without limitation, a species of *Escherichia, Actinomycetes, Alcaligenes, Bacillus, Corynebacter, Envinia, Flavobacterium, Helicobacter, Klebsiella, Lactobacillus, Moraxella, Neisseria, Paracoccus, Pseudomonas, Salmonella, Shigella, Streptococcus, Streptomyces, Vibro, Agrobacterium, Rhizobium, Sinorhizobium, Mesorhizobium*, or *Ensifer*. The DNA transfer construct can include an ARS, such as described herein, and/or a centromere sequence, where the ARS and/or centromere sequence can be derived from any species. The DNA transfer construct can include a selectable marker, such as but not limited to a gene conferring resistance to an antibiotic, toxin, or herbicide. A DNA molecule provided by the DNA transfer construct can include one or more genes of interest, such as for example, a gene encoding a functional RNA or polypeptide, such as but not limited to any disclosed herein. The DNA transfer construct can be at least about 1 kb, 10 kb, 25 kb, 50 kb, 75 kb, 100 kb, 125 kb, 150 kb, 175 kb, 200 kb, 250 kb, 300 kb, 350 kb, 400 kb, 500 kb, 600 kb, 700 kb, 800 kb, 900 kb or 1 Mbp in size. In some examples, the DNA transfer construct can replicate autonomously in the diatom ex-conjugate as an episome for at least 5, at least 10, at least 15, at least 20, at least 25, or at least 30 generations in the presence or absence of selection.

In a further aspect, provided herein is a DNA transfer construct for conjugative transformation of algae that comprises an origin of transfer, a maintenance cassette, and optionally a selectable marker. In some examples, the maintenance cassette is a nucleic acid sequence having A GC content that is at lower than the overall GC content of the intended recipient alga. For example, the GC content of the maintenance cassette sequence can be less than 50%, less than 40%, or less than or equal to about 30%. In some examples, the maintenance cassette comprises an ARS and/or a centromere sequence. In some examples, the ARS is derived from a *Saccharomyces cerevisiae* ARS. For example, the ARS can have at least 80%, at least 85%, at least 90%, at least 95%, or at least 98% identity to an *S. cerevisiae* ARS such as ARSH4 (SEQ ID NO:2). The maintenance cassette can further comprise a centromere sequence, such as an *S. cerevisiae* centromere sequence or a sequence having at least 80% identity thereto. For example, the centromere sequence can have at least 80%, at least 85%, at least 90%, at least 95%, or at least 98% identity to an *S. cerevisiae* centromere such as CEN6 (SEQ ID NO:1). In some examples the maintenance cassette is CEN6-ARSH4 (SEQ ID NO:4) or a sequence having at least 80%, at least 85%, at least 90%, at least 95%, or at least 98% identity to SEQ ID NO:4, or CEN6-ARSH4-HIS3 (SEQ ID NO:5) or a sequence having at least 80%, at least 85%, at least 90%, at least 95%, or at least 98% identity to SEQ ID NO:5. A selectable marker present on the DNA transfer construct may be an antibiotic resistance gene, a gene encoding a polypeptide conferring resistance to a toxin, an auxotrophic marker, and a combination thereof. In some aspects, the antibiotic resistance gene confers resistance to antibiotics including blasticidin, bleomycin, gentamycin, glyphosate, hygromycin, kanamycin, neomycin, nourseothricin, phleomycin, puromycin, spectinomycin, zeocin, and streptomycin. In a further aspect, the DNA transfer construct plasmid further comprises a promoter, a reporter gene, a regulatory element or a combination thereof. In one aspect, the transformation efficiency is increased at least about 100-fold using the DNA transfer construct comprising a maintenance cassette as compared to a plasmid without a maintenance cassette. In various examples, the DNA transfer construct is maintained as a replicating extra-chromosomal vector in the algal cell.

Also provided herein is a kit for transforming an algal cell comprising a DNA transfer construct, such as a DNA transfer construct plasmid vector, containing an origin of transfer and a selectable marker and *E. coli* cells that include the genes required for conjugation, e.g., the tra genes, that may be present in the bacterial chromosome or on an episome. The *E. coli* cells can be provided in a solution that includes a cryoprotectant, for example, the solution can include at least 5% glycerol. The kit can further include instructions for transforming an algal cell. In some examples, a kit includes a DNA transfer construct, such as a plasmid, containing an origin of transfer and a selectable marker; and also includes a medium for suspending or diluting the algae and/or bacteria for conjugation; and optionally instructions for transforming an algal cell. In any of the above examples, a kit can further include *E. coli* cells (e.g., as a frozen stock that includes at least 5%, at least 10%, at least 15%, at least 20%, at least 25%, or at least 30% glycerol) where the *E. coli* cells are capable of conjugative transfer, e.g., include genes either integrated into the genome or on an episome that encode the conjugative functions (mobilization genes and mating pair formation genes, e.g., the tra gene clusters). In one example, the cargo plasmid vector includes a maintenance cassette comprises an autonomous replication sequence (ARS). In a specific aspect, the maintenance cassette is a yeast maintenance cassette and can comprise CEN6-ARSH4 (SEQ ID NO:4) or a sequence having at least 80% identity thereto or CEN6-ARSH4-HIS3 (SEQ ID NO:5) or a sequence having at least 80% identity thereto. A selectable marker present on the cargo plasmid vector may be an antibiotic resistance gene, a gene encoding a polypeptide conferring resistance to a toxin, an auxotrophic marker, and a combination thereof. In some aspects, the antibiotic resistance gene confers resistance to antibiotics including blasticidin, bleomycin, gentamycin, glyphosate, hygromycin, kanamycin, neomycin, nourseothricin, phleomycin, puromycin, spectinomycin, zeocin, and streptomycin. The cargo plasmid vector can optionally further comprise a promoter, such as an algal or heterkont promoter, a reporter gene, a regulatory element or any combination thereof.

BRIEF DESCRIPTION OF THE DRAWINGS

FIG. 1A-J is a table showing parameters and results of 112 conjugation experiments in which the target cell was the diatom *Phaeodactylum tricornutum*.

FIGS. 5A-G depict the outline and results of testing p0521s and p0521 maintenance in *P. tricornutum* lines grown in the presence and absence of antibiotic selection. A) *P. tricornutum* lines containing p0521s were grown separately with or without selection for 28 days, during which time they were serially diluted one hundred-fold at three different times. B) After 28 days, culture was plated to obtain single colonies on non-selective medium and C) patched on non-selective medium. D) Colonies were replica patched on selective solid L1 medium. E) Table providing results of stability testing of plasmid p0521 in *P. tricornutum* lines after growth in seawater medium with or without antibiotic selection. F) Episome rescue from single *P. tricornutum* p0521 lines sub-cultured without (lanes 1-3) or with (lanes 4-6) antibiotic selection was performed after 18 days; G) Episome rescue from single *P. tricornutum* p0521 lines sub-cultured without (lanes 1-3) or with (lanes 4-6) antibiotic selection was performed after 38 days.

DETAILED DESCRIPTION OF THE INVENTION

Figure 2A:
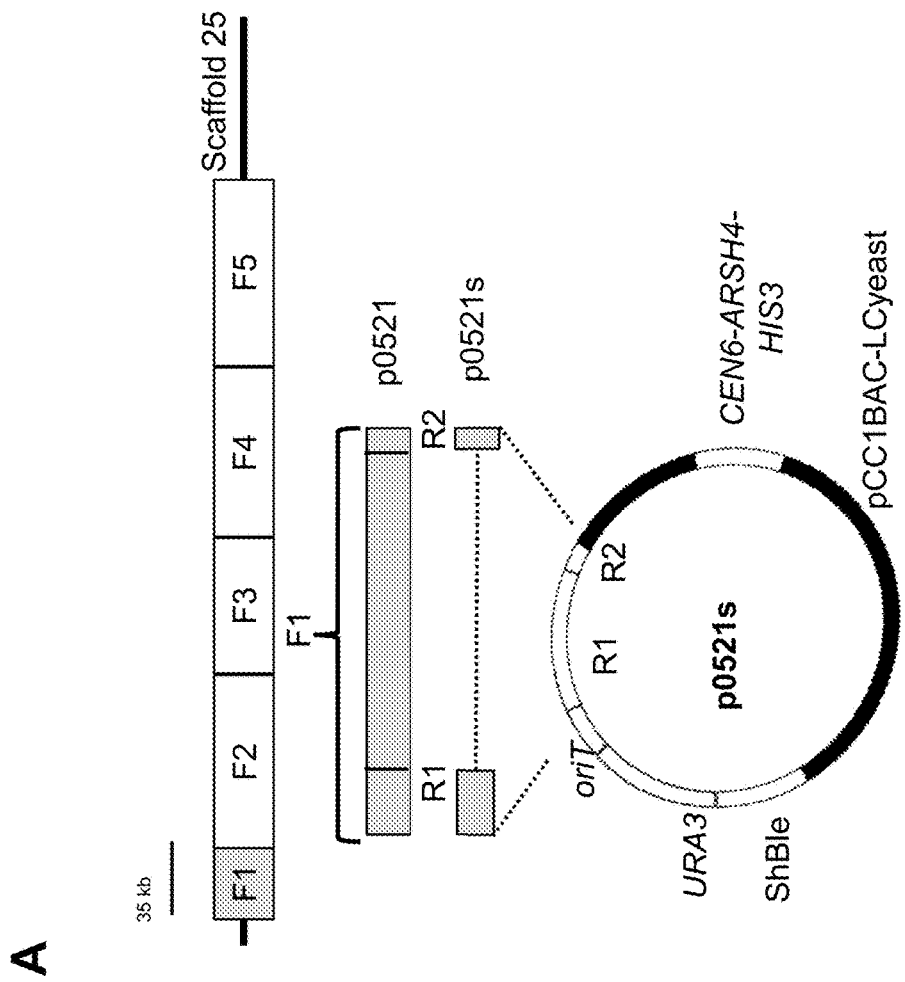
FIGS. 2A and B illustrate the conjugative transfer of plasmids from *E. coli* to *P. tricornutum*. A) Map of the cargo plasmid p0521s and derivation of sequences of the plasmid from *P. tricornutum* chromosome scaffold 25 and the recombination cloning strategy. OriT, origin of transfer; URA3, gene encoding orotidine 5'-phosphate decarboxylase from *S. cerevisiae*, and ShBle, phleomycin resistance cassette with *P. tricornutum* FcpF promoter and FcpA terminator. B) Graph and table providing average number of *P. tricornutum* colonies obtained per conjugation for different cargo plasmid variants of p0521s. The cargo plasmids listed in the table are aligned with the X axis of the graph.

The invention is not limited to the particular compositions, methods, and experimental conditions described, as such compositions, methods, and conditions may vary in the context of the invention. The terminology used herein is for purposes of describing particular embodiments and is not intended to be limiting, since the scope of the present invention will be limited only in the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. The definitions set forth below are for understanding of the disclosure but shall in no way be considered to supplant the understanding of the terms held by those of ordinary skill in the art.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

As used herein, "about" means either: within plus or minus 10% of the provided value, or a value rounded to the nearest significant figure, in all cases inclusive of the provided value. Where ranges are provided, they are inclusive of the boundary values.

As used herein, "amino acid" refers to naturally-occurring and synthetic amino acids, as well as amino acid analogs and amino acid mimetics that function in a manner similar to the naturally-occurring amino acids. Naturally-occurring amino acids are those encoded by the genetic code, including D/L optical isomers, as well as those amino acids that are later modified, e.g., hydroxyproline, y-carboxyglutamate, and O-phosphoserine. Amino acid analogs refer to compounds that have the same basic chemical structure as a naturally-occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics, as used herein, refer to chemical compounds that have a structure that is different from the general chemical structure of an amino acid, but that functions in a manner similar to a naturally-occurring amino acid.

A "nucleotide" is the basic unit of a nucleic acid molecule and typically includes a base such as adenine, guanine, cytosine, thymine, or uracil linked to a pentose sugar such as ribose or deoxyribose that is in turn linked to a phosphate group. Nucleotides can also include alternative or non-naturally occurring bases or sugars that do not occur in naturally-occurring DNA or RNA. In peptide nucleic acids one or more sugars may be substituted by amino acids, and in some nucleic acid analogs at least a portion of the phosphates may be replaced by hydroxyl groups. Although nucleotides are often used to denote the length of a single-stranded nucleic acid molecule, and "base pairs" (i.e., base paired nucleotides) are often used to denote the length of double-stranded nucleic acid molecules, in the present application, "nucleotides" or "nt" may be used interchangeably with "base pairs" or "bp", and the use of one term or the other does not meant restrict the type of nucleic acid molecule being described to being either single-stranded or double-stranded. The use of kilobases (kb) or megabases (Mbp) as units of length also applies equally to single-stranded and double-stranded nucleic acid molecules.

An "autonomously replicating sequence" or "ARS" is a sequence that serves as an origin of DNA replication on eukaryotic chromosomes. An ARS, when incorporated into a DNA molecule, supports replication of the DNA molecule by binding a protein complex that unwinds and replicates the DNA. An ARS can be confirmed (functionally validated) by incorporating the sequence into a DNA molecule that is not self-replicating in a given host and demonstrating that the DNA molecule replicates autonomously in the host only when the ARS is present.

A "nucleic acid construct", "DNA construct" or simply "construct" is a nucleic acid molecule produced by recombinant means that includes at least two juxtaposed or operably linked nucleic acid sequences that are not juxtaposed or operably linked to one another in nature.

An "episomal DNA molecule" or "EDM" or "episome" is an independently replicating nucleic acid molecule that is not integrated into the genome of the host organism in which the EDM resides and replicates. An EDM may be stable, in which it persists for many generations or unstable, where the EDM is gradually diluted out of the population by successive cell divisions. A stable EDM may be maintained in a cell population by selective pressure (e.g., the presence of an antibiotic).

As used herein, the term "exconjugate" refers to a cell that has received a nucleic acid molecule via conjugation.

A "detectable marker" is a gene or the polypeptide encoded by the gene that confers some detectable phenotype on a cell that expresses the gene. Detection can be colorometric (for example, the blue color by expression of beta galactosidase or beta-glucuronidase in the presence of a colorometric substrate) or by detection of luminescence or fluorescence. A detectable marker generally encodes a detectable polypeptide, for example, a green fluorescent protein or a signal producing enzyme such as luciferase, which, when contacted with an appropriate agent (a particular, wavelength of light or luciferin, respectively) generates a signal that can be detected by eye or using appropriate instrumentation (Giacomin, *Plant Sci.* 116:59-72, 1996; Scikantha, *J. Bacteriol.* 178:121, 1996; Gerdes, *FEBS Lett.* 389:44-47, 1996; see, also, Jefferson, *EMBO J.* 6:3901-3907, 1997).

The term or "selectable marker" or "selection marker" refers to a gene (or the encoded polypeptide) that confers a phenotype that allows the organism expressing the gene to survive under selective conditions. For example, a selectable marker generally is a molecule that, when present or expressed in a cell, provides a selective advantage (or, if a negative selectable marker, disadvantage) to the cell containing the marker, for example, the ability to grow in the presence of an agent that otherwise would kill the cell (e.g., a toxin or antibiotic), or the ability to grow in the absence of a particular nutrient.

A "cDNA" is a DNA molecule that comprises at least a portion the nucleotide sequence of an mRNA molecule, with the exception that the DNA molecule substitutes the nucleobase thymine, or T, in place of uridine, or U, occurring in the mRNA sequence. A cDNA can be single-stranded or double-stranded, and can be the complement of the mRNA sequence. In preferred embodiments, a cDNA does not include one or more intron sequences that occur in the naturally-occurring gene (in the genome of an organism) that the cDNA corresponds to. For example, a cDNA can have sequences from upstream (5') of an intron of a naturally-occurring gene juxtaposed to sequences downstream (3') of the intron of the naturally-occurring gene, where the upstream and downstream sequences are not juxtaposed in a DNA molecule (i.e., the naturally occurring gene) in nature. A cDNA can be produced by reverse transcription of mRNA molecules by a polymerase (e.g., a reverse transcriptase), or can be synthesized, for example, by chemical synthesis and/or by using one or more restriction enzymes, one or more ligases, one or more polymerases (including, but not limited to, high temperature tolerant polymerases that can be used in polymerase chain reactions (PCRs)), one or more recombinases, e.g., based on knowledge of the cDNA sequence, where the knowledge of the cDNA sequence can optionally be based on the identification of coding regions from genome sequences and/or the sequences of one or more cDNAs.

A "centromere" is a region of a eukaryotic chromosome at which the kinetochore forms. Thus, the centromere is responsible for equal portioning of chromosomes to daughter cells during mitosis and meiosis.

A "coding sequence" or "coding region", as used herein in reference to an mRNA or DNA molecule, refers to the portion of the mRNA or DNA molecule that codes for a polypeptide. It typically consists of the nucleotide residues of the molecule which are matched with an anticodon region of a transfer RNA molecule during translation of the mRNA molecule or which encode a stop codon. The coding sequence may include nucleotide residues corresponding to amino acid residues which are not present in the mature protein encoded by the mRNA molecule (e.g., amino acid residues in a protein export signal sequence).

"Derived from" refers to the source of a nucleotide or amino acid sequence, and typically means the sequence of the nucleic acid molecule, protein, or peptide is based on that of the referenced nucleic acid molecule, protein, or peptide. The nucleic acid molecule, protein, or peptide is either a variant having at least 60% identity (and, in various examples, at least 75%, at least 70%, at least 75%, at least 80%, at least 85% at least 90%, or at least 95% identity) to the referenced nucleic acid molecule, protein, or peptide, and/or is a truncated or internally deleted variant of the referenced nucleic acid molecule, protein, or peptide. For example, a protein or peptide may be C-terminally or N-terminally truncated or internally deleted with respect to the protein or peptide it is derived from and may have a C-terminal, N-terminal, or internal deletion of any number of amino acids, for example, at least 1, 2, 3, 4, 5, 10, 20, 30, 40, 50, 60, 70, 80, 90, or 100 amino acids. A nucleic acid molecule may be 5' or 3' truncated or internally deleted with respect to the nucleic acid molecule it is derived from and may have a 5', 3', or internal deletion of any number of nucleotides, for example, at least 1, 2, 3, 4, 5, 10, 20, 30, 40, 50, 60, 70, 80, 90, 100, 150, or 200 nucleotides.

As used herein, the terms "percent identity" or "homology" with respect to nucleic acid or polypeptide sequences are defined as the percentage of nucleotide or amino acid residues in the candidate sequence that are identical with the known or referenced nucleic acid molecule or polypeptide, after aligning the sequences for maximum percent identity and introducing gaps, if necessary, to achieve the maximum percent homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), *Nucleic Acids Res.* 25, 3389-3402, and Karlin (1990), *Proc. Natl. Acad. Sci. USA* 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), *Nature Genetics* 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), *Proc. Natl. Acad. Sci. USA* 89, 10915-10919), recommended for query sequences over 85 in length (nucleotide bases or amino acids).

Unless otherwise specified, in referring to nucleic acid molecules having a given percent identity to a reference sequence, insertions or deletions of less than about 100 nucleotides, for example, less than about 90, less than about 75, less than about 60, less than about 45, less than about 30 or less than about 15 nucleotides shall not be construed as affecting homology, and 5' or 3' end extensions shall not be construed as affecting homology, nor shall 5' or 3' deletions of less than about 100 nucleotides, for example, less than about 90, less than about 75, less than about 60, less than about 45, less than about 30 or less than about 15 nucleotides be construed as affecting homology. For polypeptide sequences, N-terminal or C-terminal insertion or deletions shall not be construed as affecting homology (percent identity), and internal deletions and/or insertions into the polypeptide sequence of less than about 30, less than about 20, or less than about 10 amino acid residues shall not be construed as affecting homology.

Thus, when referring to the polypeptide or nucleic acid sequences of the present invention, included are sequence identities of at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the full-length polypeptide or nucleic acid sequence and variants of such sequences, including truncated versions of the sequences and variants wherein at least one nucleotide or amino acid residue has been inserted N- and/or C-terminal to (or 5' and/or 3' of), and/or within, the disclosed sequence(s) which contain(s) the insertion and substitution. Contemplated variants can additionally or alternatively include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion, deletion, and/or substitution. Also contemplated are polypeptide derivatives in which the polypeptide has been covalently modified by substitution, chemical, enzymatic, or other appropriate means with a moiety other than a naturally occurring amino acid which contains the insertion and substitution (for example, a detectable moiety such as an enzyme).

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) Principles of Protein Structure, Springer-Verlag). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

Gene and protein Accession numbers, commonly provided in parenthesis after a gene or species name, are unique identifiers for a sequence record publicly available at the National Center for Biotechnology Information (NCBI) website (ncbi.nlm.nih.gov) maintained by the United States National Institutes of Health. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appear in a specific GenBank record. Searching and obtaining nucleic acid or gene sequences or protein sequences based on Accession numbers and GI numbers is well known in the arts of, e.g., cell biology, biochemistry, molecular biology, and molecular genetics. Protein-encoding regions of a genome may also be identified by "Protein ID" which is an identifier that can be used to search genome databases at genome.jgi.doe.gov. Organisms can be searched by genus and/or species and the particular chromosomal sequence can be searched using the protein ID number.

"Expression cassette" as used herein means a DNA sequence capable of directing expression of a particular nucleotide sequence in an appropriate host cell, comprising a promoter operably linked to a nucleotide sequence of interest, which can optionally be operably linked to termination signals and/or other regulatory elements. An expression cassette may also comprise sequences that enable, mediate, or enhance translation of the nucleotide sequence. The coding region usually codes for a protein of interest but may also code for a functional RNA of interest, for example antisense RNA or a non-translated RNA, in the sense or antisense direction. An expression cassette may be assembled entirely extracellularly (e.g., by recombinant cloning techniques). However, an expression cassette may also be assembled using in part endogenous components. For example, an expression cassette may be obtained by placing (or inserting) a promoter sequence upstream of an endogenous sequence, which thereby becomes functionally linked and controlled by said promoter sequences. The expression of the nucleotide sequence in the expression cassette may be under the control of a constitutive promoter or of an inducible promoter which initiates transcription only when the host cell is exposed to some particular external stimulus.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Examples of expression vectors known in the art include cosmids, plasmids and viruses (e.g., retroviruses, lentiviruses, adenoviruses, and adeno-associated viruses) that incorporate the recombinant polynucleotide.

An "oligonucleotide", as used herein, is a nucleic acid molecule 200 or fewer nucleotides in length. An oligonucleotide can be RNA, DNA, or a combination of DNA and RNA, a nucleic acid derivative, or a synthetic nucleic acid, for example, an oligonucleotide can be a peptide nucleic acid or a locked nucleic acid, and can be single-stranded, double-stranded, or partially single-stranded and partially double-stranded. An oligonucleotide can be, for example, between about 4 and about 200 nucleotides in length, between about 6 and about 200 nucleotides in length, between about 10 and about 200 nucleotides in length, between about 15 and about 200 nucleotides in length, between about 17 and about 200 nucleotides in length, between about 20 and about 200 nucleotides in length, or between about 40 and about 200 nucleotides in length. In additional examples, an oligonucleotide can be between about 15 and about 180 nucleotides in length, between about 15 and about 160 nucleotides in length, between about 15 and about 140 nucleotides in length, between about 15 and about 120 nucleotides in length, between about 17 and about 100 nucleotides in length, between about 17 and about 80 nucleotides in length, or between about 17 and about 70 nucleotides in length, for example between about 20 and about 65 nucleotides in length.

When used in reference to a polynucleotide, a gene, a nucleic acid, a polypeptide, or an enzyme, the term "heterologous" refers to a polynucleotide, gene, a nucleic acid, polypeptide, or an enzyme not derived from the host species, e.g., from a different species with respect to the host cell. When referring to nucleic acid sequences operably linked or otherwise joined to one another ("juxtaposed") in a nucleic acid construct or molecule, "heterologous sequences", as used herein, are those that are not operably linked or are not in proximity or contiguous to each other in nature. Similarly, when referring to a gene regulatory sequence or to an auxiliary nucleic acid sequence used for maintaining or manipulating a gene sequence (e.g. a 5' un-translated region, 3' un-translated region, Kozak sequence, poly A addition sequence, intron sequence, splice site, ribosome binding site, internal ribosome entry sequence, genome homology region, recombination site, e.g.), "heterologous" means that the regulatory sequence or auxiliary sequence is from a different source (e.g., different gene, whether from the same or different species as the host organisms) than the gene with which the regulatory or auxiliary nucleic acid sequence is juxtaposed or operably linked in a construct, genome, chromosome, or episome.

The terms "nucleic acid molecule" and "polynucleotide molecule" are used interchangeably herein, and refer to both DNA and RNA molecule, including cDNA, genomic DNA, synthetic DNA, and DNA or RNA containing nucleic acid analogs. Polynucleotides can have any three-dimensional structure. Polynucleotides can be natural-occurring or synthetic origin. A nucleic acid molecule can be double-stranded or single-stranded. Non-limiting examples of polynucleotides include genes, gene fragments, exons, introns, messenger RNA (mRNA), transfer RNA (tRNA), ribosomal RNA (rRNA), siRNA, micro-RNA, ribozymes, tracr RNAs, crRNAs, chimeric guide RNAs, cDNA, recombinant polynucleotides, branched polynucleotides, nucleic acid probes and nucleic acid primers. A polynucleotide may contain unconventional or modified nucleotides.

As used herein, "operably linked" is intended to mean a functional linkage between two or more sequences such that activity at or on one sequence affects activity at or on the other sequence(s). For example, an operable linkage between a polynucleotide of interest and a regulatory sequence (e.g., a promoter) is a functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site. Operably linked elements may be contiguous or non-contiguous. When used to refer to the joining of two protein coding regions, by "operably linked" is intended that the coding regions are in the same reading frame. When used to refer to the effect of an enhancer, "operably linked" indicated that the enhancer increases the expression of a particular polypeptide or polynucleotides of interest. "Juxtaposed with" in the context of nucleic acid sequences, means the referenced sequences are part of the same continuous nucleic acid molecule.

A "promoter" refers to a transcription control sequence that is capable of initiating transcription in a host cell and can drive or facilitate transcription of a nucleotide sequence or fragment thereof of the instant invention. Such promoters need not be of naturally-occurring sequences. In addition, it will be understood that such promoters need not be derived from the target host cell or host organism.

"Polypeptide" and "protein" are used interchangeably herein and refer to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition. In various embodiments the polypeptides can have at least 10 amino acids or at least 25, or at least 50 or at least 75 or at least 100 or at least 125 or at least 150 or at least 175 or at least 200 amino acids.

As used herein "progeny" means a descendant, offspring, or derivative of an organism. For example, daughter cells from a transgenic alga are progeny of the transgenic alga. Because certain modifications may occur in succeeding generations due to mutations or environmental influences, such progeny, descendant, or derivatives may not, in fact, be identical to the parent cell, but are still included within the scope of the term as used herein.

The terms "recombinant" or "engineered" as used herein in reference to a nucleic acid molecule, refer to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence. A "recombinant protein" is a protein produced by genetic engineering, for example, by expression of a genetically engineered nucleic acid molecule in a cell.

The term "regulatory region", "regulatory sequence", "regulatory element", or "regulatory element sequence", as used in the present invention, refer to a nucleotide sequence that influences transcription or translation initiation or rate, and stability and/or mobility of a transcription or translation product. Such regulatory regions need not be of naturally-occurring sequences. Regulatory sequences include but are not limited to promoter sequences, enhancer sequences, response elements, protein recognition sites, inducible elements, protein binding sequences, 5' and 3' un-translated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR).

As used herein, "transgenic organism" refers to an organism which comprises a heterologous polynucleotide. When applied to organisms, the terms "transgenic" or "recombinant" or "engineered" or "genetically engineered," used interchangeably herein, refer to organisms that have been manipulated by introduction into the organism of an exogenous or recombinant nucleic acid sequence. Generally, the heterologous polynucleotide is stably integrated within the genome such that the polynucleotide is passed on to successive generations, although it can also be present on an episome, and may be present on a synthetic chromosome of the transgenic organism. The non-native polynucleotide may be integrated into the genome alone or as part of a recombinant expression cassette. In additional examples, a transgenic microorganism can include an introduced exogenous regulatory sequence operably linked to an endogenous gene of the transgenic microorganism. Non-limiting examples of such manipulations include gene knockouts, targeted mutations and gene replacement, promoter replacement, deletion, or insertion, as well as introduction of transgenes into the organism. Recombinant or genetically engineered organisms can also be organisms into which constructs for gene "knock down" have been introduced. Such constructs include, but are not limited to, RNAi, microRNA, shRNA, antisense, and ribozyme constructs. Also included are organisms whose genomes have been altered by the activity of meganucleases, TALENs, zinc finger nucleases, or RNA guided endonucleases, e.g., CRISPR nucleases. As used herein, "recombinant microorganism" or "recombinant host cell" includes progeny or derivatives of the recombinant microorganisms of the invention. Because certain modifications may occur in succeeding generations from either mutation or environmental influences, such progeny or derivatives may not, in fact, be identical to the parent cell, but are still included within the scope of the term as used herein.

For nucleic acids and polypeptides, the term "variant" is used herein to denote a polypeptide, protein, or polynucleotide molecule with some differences, generated synthetically or naturally, in their base or amino acid sequences as compared to a reference polypeptide or polynucleotide, respectively, such that the variant has at least 70% sequence identity with the reference polypeptide or polynucleotide. In other embodiments the variant can have at least 80%, at least 85%, at least 90%, at least 95%, at least 96%, at least 97%, at least 98%, or at least 99% sequence identity with the reference polypeptide or polynucleotide. Alternatively or in addition, a variant can have one or more insertions or deletions in response to a reference polypeptide or polynucleotide. For example, protein variants may be N-terminally truncated or C-terminally truncated with respect to the reference sequence, or can have one or more internal deletions, while nucleic acid variants may have a 5' end and/or 3' end sequence truncation and/or can have one or more internal deletions. Further, a protein variant may have an additional sequence added to the N-terminus and/or C-terminus with respect to the reference sequence, or can have one or more internal additional sequences, while nucleic acid variants may have a 5' end and/or 3' end addition and/or can have one or more internal sequence additions. A variant can have any desired combination of substitutions, insertions, and/or deletions with respect to a reference polypeptide or polynucleotide. Polypeptide and protein variants can further include differences in post-translational modifications (such as glycosylation, methylation. phosphorylation, e.g.). When the term "variant" is used in reference to a microorganism, it typically refers to a strain microbial strain having identifying characteristics of the species to which it belongs, while having at least one nucleotide sequence variation or identifiably different trait with respect to the parental strain, where the trait is genetically based (heritable).

A "vector" is any genetic element capable of serving as a vehicle of genetic transfer, expression, or replication for a foreign polynucleotide in a host cell. For example, a vector may be an artificial chromosome or a plasmid, and may be capable of stable integration into a host cell genome, or it may exist as an independent genetic element (e.g., episome, plasmid). A vector may exist as a single polynucleotide or as two or more separate polynucleotides. Vectors may be single copy vectors or multicopy vectors when present in a host cell.

Algae are a very large and diverse group of eukaryotic organisms, ranging from unicellular genera such as *Chlorella* and the diatoms to multicellular forms such as the giant kelp, a large brown alga that may grow up to 50 meters in length. Unicellular algae are often called "microalgae" to distinguish them from large aquatic plants ("seaweed"). Eukaryotic microalgae include green algae (chlorophytes), red algae (rhodophytes), diatoms (bacillariophytes), eustigmatophytes, pelagophytes, prasinophytes, glaucophytes, chlorarachniophytes, euglenophytes, chromophytes, xanthophytes, and dinoflagellates.

Representative algae that may be transformed by conjugation include eukaryotic microalgae, e.g., green algae (chlorophytes), red algae (rhodophytes), diatoms (bacillariophytes), pelagophytes, prasinophytes, glaucophytes, chlorarachniophytes, euglenophytes, chromophytes, xanthophytes, and dinoflagellates. As nonlimiting example, eukaryotic microalgal species used in the invention herein can be members of any of the genera *Amphora, Ankistrodes-* mus, *Aplanochytrium, Asteromonas, Aureococcus, Boekelovia, Bolidomonas, Borodinella, Botrydium, Botryococcus, Bracteacoccus, Carteria, Chaetoceros, Chlamydomonas, Chlorella, Chlorococcum, Chlorogonium, Chrococcidiopsis, Chroomonas, Chrysophyceae, Chrysosphaera, Cricosphaera, Crypthecodinium, Cryptococcus, Cryptomonas, Cyanidioschyzon, Cyclotella, Cylindrotheca, Cymbella, Desmodesmus, Dunaliella, Elina, Elhpsoidon, Emiliania, Eremosphaera, Ernodesmius, Euglena, Eustigmatos, Fragilaria, Fragilariopsis, Franceia, Gloeothamnion, Haematococcus, Hantzschia, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phaeodactylum, Picochlorum, Platymonas, Pleurochrysis, Pleurococcus, Porphyridium, Prototheca, Pseudochlorella, Pseudoneochloris, Pseudostaurastrum, Pyramimonas, Pyrobotrys, Rholdella, Scenedesmus, Schizochlamydella, Skeletonema, Spirulina, Spyrogyra, Staurastrum, Stichococcus, Tetrachlorella, Tetraselmis, Thalassiosira, Tribonema, Vaucheria, Vibrio, Viridiella, Vischeria,* and *Volvox.*

The green algae (chlorophytes) are a large group of algae. The green algae include unicellular and colonial flagellates, most with two flagella per cell, as well as various colonial, coccoid and filamentous forms, and macroscopic seaweeds. There are about 8,000 species of green algae. Many species live most of their lives as single cells, while other species form colonies, long filaments, or highly differentiated macroscopic seaweeds. Exemplary green algae (Chlorophytes) may include members of the genera *Bryopsidophyceae, Chlorodendrophyceae, Chlorophyceae, Chlorophyta incertae sedis, Dasycladophyceae, Mamiellophyceae, Nephroselmidophyceae, Pedinophyceae, Pleurastrophyceae, Prasinophyceae, Siphonocladophyceae, Trebouxiophyceae, Ulvophyceae.* Chlorophytes that can be used for genetic modification or nucleic acid isolation include, for example, species of *Botryococcus, Chlamydomonas, Chlorella, Desmodesmus, Dunaliella, Elipsoidon, Haematococcus, Micromonas, Nannochloris, Ostreococcus, Parachlorella, Pseudochlorella, Scendedesmus, Tetrachlorella, Tetraselmis,* and *Vovlox.* In some examples, an algal recipient can be a species of *Chlamydomonas, Chlorella, Desmodesmus, Haematococcus, Parachlorella,* or *Tetraselmis.*

Diatoms are algae and are also heterokonts (stramenopiles). Diatom cells are contained within a unique silica cell wall comprising two separate valves (or shells). The biogenic silica that the cell wall is composed of is synthesized intracellularly by the polymerization of silicic acid monomers. This material is then extruded to the cell exterior and added to the wall.

Additional heterokont species in which may be used as recipients for conjugative transfer of DNA include, but are not limited to, species of the taxonomic groups bacillariophytes (diatoms), eustigmatophytes, pelagophytes, and xanothophytes, as well as nonphotosynthetic heterokonts including, for example, oomycetes, labrinthulids, and thraustochytrids. In some examples, a strain used in the invention may be a species of Labrinthulid or Thraustochytrid such as a *Labrynthula, Labrinthuloides, Thraustochytrium, Schizochytrium, Aplanochytrium, Aurantiochytrium, Oblongichytrium, Japonochytrium, Diplophrys,* or *Ulkenia* species. Heterokont unicellular algae include bacillariophytes (diatoms) and eustigmatophytes. Eustigmatophytes that can be used for genetic modification or nucleic acid isolation include, for example, species of *Eustigmatos,* *Monodus, Nannochloropsis,* and *Vischeria.* Particularly suitable species of *Nannochloropsis* include *N. gaditana, N. granulata, N. limnetica, N. maritime, N. oceanica, N. oculata,* and *N. salina.* Exemplary diatoms may include members of the genera *Achnanthes, Amphora, Chaetoceros, Coscinodiscus, Cylindrotheca, Cyclotella, Cymbella, Fragilaria, Fragilariopsis, Hantzschia, Navicula, Nitzschia, Pavlova, Pseudo-Nitzschia, Phaeodactylum, Psammodictyon, Skeletonema, Thalassionema,* and *Thalassiosira.*

Bacterial conjugation is a process by which genetic material is transferred from donor cells to recipient cells. The transfer of these conjugative genes requires a sophisticated machinery that ensures DNA mobilization (brought about by MOB genes) and mating pair formation (organized by MPF genes). These genes can be encoded by an autonomous replicating plasmid or by integrative conjugative elements inserted in the chromosome. Conjugation in Gram-negative bacteria is mediated by the Type IV secretion system (T4SS), a large macromolecular complex involved in substrate transport and pilus biogenesis. T4SSs are implicated not only in bacterial conjugation, but also in the secretion of virulence factors to eukaryotic cells. Many effectors secreted by T4SS are virulence factors involved in pathogenic diseases, such as brucellosis, whooping cough, cat scratch disease, pneumonia or gastric ulcer, caused by bacterial infection with *Brucella suis, Bordella pertussis, Bartonella henselea, Legionella pneumonia* or *Helicobacter pylori,* respectively. Further, bacterial conjugation is one of the main mechanisms whereby bacteria become resistant to antibiotics.

Conjugative T4SSs are essential for mating pair formation (MPF) and are encoded by MPF genes. Along with other proteins T4SS proteins assemble into macromolecular complexes which span the inner and outer membrane and periplasm in between. Four protein domains can be distinguished in T4SS: the pilus, the core channel complex, the inner membrane platform and the hexameric ATPases that supply energy for pilus biogenesis and substrate transport. Pilus generation involves prepilin processing, pili extraction from the inner membrane and pilus elongation. The next step is the assembly of the secretion channel (core complex) which spans across the inner and outer membranes and the periplasm in between.

Substrate transport during conjugation is a four step process. The first step involves the donor cell contacting the recipient cells mediated by the pilus. This can be triggered by specific factors in the recipient. The plasmid DNA to be transferred by conjugation contains an origin of transfer (oriT) which is a short sequence (up to 500 bp) of DNA consisting of three functionally defined domains: a nicking (nic) domain, a transfer domain, and a termination domain. Auxiliary factors bind to the oriT and cleaves the oriT at a nic site resulting in a nucleoprotein complex called a relaxosome being formed. During the second step, the nucleoprotein complex is recruited to the membrane channel to initiate transfer. This step is mediated by the coupling protein, which binds to the relaxosome with the assistance of the auxiliary proteins. Upon cell contact, the retraction of the extracellular pilus facilitates the interaction between membranes of the donor and recipient cells, resulting in the membrane fusion process. Simultaneously, or prior to this membrane fusion, the coupling protein drives the relaxosome towards the secretion channel. The third step involves the transfer of the substrate to proteins associated with the T4SS. The relaxase is unfolded and translocated through the channel covalently bound to the DNA. In the final step, proteins associated with the T4SS are displaced at the base of the secretion channel by the coupling protein, which assists DNA translocation in a 5' to 3' direction.

Genes required for conjugation (mobilization of the DNA transfer construct) include the mobilization MOB genes and MPF genes, encoded by the tra1 and tra2 gene clusters in *E. coli*, which may be present in the host cell chromosome or on a separate episome, e.g., a "conjugative plasmid" or "mobilization plasmid" See, for example, Lawley et al. (2003) *FEMS Microbiol. Lett.* 224:1-15; Strand et al. (2014) *PLoS One* 9:e90372 and Cabezon et al. (2015) *FEMS Microbiol. Rev.* 39:81-95, all incorporated herein in their entireties.

During conjugation, donor cells are contacted with the recipient cells under suitable conditions. The conditions for conjugation are dependent on the nature of the donor and recipient cells, and can be empirically determined by one of skill in the art. As described in the Examples, where the bacterial species used for conjugation and algal recipient have different temperature optimums, these conditions can optionally include two sequential incubations under different conditions followed by selection. During first incubation, the bacterial and algal cells may be incubated together for from about 10 minutes to one day or longer, for example, from about ten minutes to about 16 hours, or from about 20 minutes to about 12 hours, or from about 30 to about 120 min at a temperature which is optimal or beneficial for bacterial cells while tolerated for at least a period of time by algal cells (e.g., from about 25-37° C., or for example about 30° C.). For example, the incubation of bacterial donor cells with eukaryotic algal or heterkont recipient cells can be at a temperature higher than the optimal growth temperature of the heterokont or algal cells, and may be at a temperature higher than the optimal growth temperature of the heterokont or algal cells and lower than the optimal growth temperature of the bacterial cells. During the second incubation the cells may be incubated for a longer period of time, e.g., 1-2 days, at a temperature which is lower than optimal culture conditions for bacteria but more beneficial for the algal species (e.g., about 15-28° C., e.g., about 18° C.). Such conditions will depend on the algal and bacteria species used in the methods.

The bacterial donor cell can be any bacterial cell that has conjugative capability, e.g., any bacterial cell that includes genes encoding the necessary conjugative functions, which may be native genes or may be genes that have been introduced into the conjugative donor cell. The bacterial donor cell can be of a species of gram negative or gram positive bacteria. For example, the recipient cell can be a diatom and the donor bacterium can be a species of any of the genera *Escherichia, Actinomycetes, Alcaligenes, Bacillus, Corynebacter, Envinia, Flavobacterium, Helicobacter, Klebsiella, Lactobacillus, Moraxella, Neisseria, Paracoccus, Pseudomonas, Salmonella, Shigella, Streptococcus, Streptomyces, Vibro, Agrobacterium, Rhizobium, Sinorhizobium, Mesorhizobium,* or *Ensifer.*

The Rhizobiaceae are a family of bacteria that are parasitic on plant cells. Included among the Rhizobiaceae are the genera *Agrobacterium, Allorhizhobium, Carbophilus, Ensifer, Kaistia, Neorhizobium, Pararhizobium, Rhizobium, Shinella, Sinorhizobium,* and *Candidatus*. Bacteria of this family are adapted to insert DNA into a eukaryotic host cell, and more particularly a walled plant cell, using the T4SS mentioned above. The invention contemplates conjugation systems for algal and heterokont cells, e.g., eukaryotic microalgae and heterokont microorganisms, where the donor cell is not a species of the Rhizobiaceae, for example, is not a species of an *Agrobacterium, Allorhizhobium, Carbophilus, Ensifer, Kaistia, Neorhizobium, Pararhizobium, Rhizobium, Shinella, Sinorhizobium,* or *Candidatus* genus.

The invention illustrates the use of a non-Rhizobiaceae conjugative donor bacterium in conjugative transfer of DNA to heterokonts, such as, for example, a species of *Bacillus, Escherichia, Clostridium, Pseudomonas, Vibrio,* or *Streptomyces*. In an exemplary embodiment, the bacterial cell used to transfer DNA into an algal cell is *Escherichia coli*, a well-developed cloning host. The necessary MPF and MOB genes for conjugation-based DNA transfer can be present in the host chromosome, on an episome (e.g., conjugative plasmid), or a combination thereof.

Provided herein is a method of delivering a nucleic acid molecule to an algal cell comprising contacting the algal cell with a bacterium comprising a DNA transfer construct comprising the nucleic acid molecule such that the nucleic acid molecule is delivered to the cell. In various embodiments, the bacterium is not a member of the Rhizobiaceae. For example, the bacterium can be a gram positive or gram negative non-Rhizobiaceae bacterium that includes the required genes encoding the DNA transfer functions, e.g., mobilization (MOB) genes and mating pair formation (MPF) genes. In one embodiment, the bacterium is *E. coli*. The nucleic acid molecule is preferably provided in the *E. coli* donor cell in a DNA transfer construct that includes an origin of transfer (oriT). In some embodiments, all or a portion of the DNA transfer construct becomes established as an episome in the algal recipient cell.

The DNA transfer constructs used in the methods provided herein can include, in addition to an origin of transfer, an ARS. An ARS is a DNA sequence required for DNA replication during cell division (Gilbert (2001) *Science* 294:96-100). An ARS present on a DNA transfer construct as provided herein can be a sequence from an algal genome, or can be from a non-algal species, or can be a synthetic sequence that has been demonstrated to act as an ARS. For example, an ARS used in a DNA transfer construct can be a sequence isolated from a plant, algal, fungal, or heterokont species that is demonstrated to support replication of an episomal DNA molecule in a host cell of interest, or a sequence derived therefrom that supports episomal replication (see for example US2015/0094209, incorporated herein by reference). In some examples an ARS sequence is a *Saccharomyces* ARS sequence. One example of an ARS that can be present on a DNA transfer construct for conjugative transformation of algae is ARSH4 of *S. cerevisiae* (SEQ ID NO:2) or a sequence at least 80%, at least 85%, at least 90%, at least 95%, or at least 98% identical thereto.

The DNA transfer constructs used in the methods provided herein can alternatively or in addition include a centromere sequence. Centromeres are the regions of chromosomes at which the kinetochore assembles. The kinetochore is the multi-protein complex responsible for the segregation of paired chromosomes during cell division, thus functional centromeres allow for stable inheritance and consistent copy number of chromosomes over generations (Kalitsis & Choo (2012) *Chromosoma* 121:327-340). The centromere is an important element in an artificial chromosome, mediating faithful chromosome segregation between the two daughter cells in cell division.

Centromere sequences that may find use in a DNA transfer construct as provided herein include, without limitation, plant centromere sequences, fungal centromere sequences, and centromere sequences identified in other algal species, such as, for example, those described in Maruyama et al. (2008) *Plant Signal Behav.* 3:140-141 and US 2010/0041035, both incorporated herein by reference. As demonstrated herein, a yeast centromere sequence can be used effectively in a DNA transfer construct for transformation of algae. For example, the *Saccharomyces* CEN6 sequence (SEQ ID NO:1) and sequences having at least 80%, at least 85%, at least 90%, at least 95%, or at least 98% identity thereto are exemplary embodiments of a centromere sequences that can be included in a DNA transfer construct as provided herein.

An ARS, a centromere sequence, or both, present in a DNA transfer construct can have a GC content lower than the GC content of the intended recipient cell. In some examples, the GC content of ARS, centromere sequence, or both present on a DNA transfer construct is less than 50%, less than 40%, less than 30%, less than 20%, or less than 15%.

A DNA transfer construct as provided herein can include a maintenance cassette that comprises a centromere sequence and an ARS, which can be derived from the same or different species (which can be the same as or different from the algal species to be transformed), or either or both can be at least partially synthetic. In a specific example, in the maintenance cassette exemplified herein the centromere sequence can be *Saccharomyces* centromere sequence, such as *S. cerevisiae* CEN6 (SEQ ID NO:1) or a sequence having at least 85%, at least 90%, at least 95%, or at least 98% identity thereto and the ARS can be a *Saccharomyces* ARS, such as *S. cerevisiae* ARSH4 (SEQ ID NO:2) or a sequence having at least 85%, at least 90%, at least 95%, or at least 98% identity thereto. Other nonlimiting examples of centromere sequences and additional ARSs can be found in U.S. Patent Publication Nos. US 2010/0041035 and US 2015/0094209, incorporated herein by reference. Additionally, the maintenance cassette may include additional nucleic acids. For example, the maintenance cassette may include a selectable marker (e.g., HIS3 (SEQ ID NO:3)). The DNA transfer construct can include, for example SEQ ID NO:1 and SEQ ID NO:2, which may be present contiguously (CEN6-ARSH4; SEQ ID NO:4) on the DNA transfer construct. The DNA transfer construct can include, for example all of SEQ ID NO:1, SEQ ID NO:2, and SEQ ID NO:3, in any order, including contiguously (CEN6-ARSH4-HIS3, SEQ ID NO:5).

In various embodiments a maintenance cassette can comprise a nucleic acid sequence having at least 80%, at least 85%, at least 90%, at least 95%, at least 96%, at least 97%, at least 98%, at least 99% identity to at least 200, at least 300, at least 400, at least 500, at least 600, at least 700, at least 800, at least 900, at least 1000, at least 1100, at least 1200, at least 1300 contiguous nucleotides of SEQ ID NO:4 or SEQ ID NO:5.

An episome of the present invention (such as a transfer construct after conjugation with the recipient cell) can be tested for autonomous replication (nonintegration) in a recipient host cell by isolating uncut DNA from the recipient host cell that includes the DNA transfer grown with or without selection construct and demonstrating transformation of a convenient host, such as, for example, *E. coli* or *Saccharomyces*, with the DNA transfer construct (where the DNA transfer construct also includes an origin of replication and selectable marker functional in *E. coli* or *Saccharomyces*), by demonstration by enzyme digestion followed by gel electrophoresis and Southern hybridization that the transfer construct is maintained in the host in circular form, and/or demonstration by PCR and/or DNA sequencing that the transfer construct sequences are maintained intact and non-integrated in the host. In some instances, there may be additional host genomic DNA inserted into the DNA transfer construct.

The transfer construct, after becoming established in the recipient cell, can be also be tracked by including a gene encoding a fluorescent reporter, such as for example GFP, on the DNA transfer construct. The fluorescent reporter can conveniently be used to determine whether the transfer construct persists in the cells over generations (with or without selection), and can be detected in cell populations using a flow cytometer or in cells using any other feasible cellular fluorescence detection device, including a plate reader or fluorescence microscope.

Detectable markers or reporter genes can include genes encoding a variety of fluorescent proteins, including without limitation green, cyan, blue, yellow, orange, and red fluorescent proteins and their variants. Other markers that can be used include enzymes that produce fluorescent or chromogenic products include luciferase (Falciatore et al., *J. Mar. Biotechnol.*, 1: 239-251, 1999; Fuhrmann et al., *Plant Mol. Biol.*, 2004; Jarvis and Brown, *Curr. Genet.*, 19: 317-322, 1991), β-glucuronidase (Chen et al., 2001, supra; Cheney et al., 2001, supra; Chow and Tung, 1999, supra; El-Sheekh, 1999, supra; Falciatore et al., 1999, supra; Kubler et al., *J. Mar. Biotechnol.*, 1:165-169, 1994), and β-galactosidase (Gan et al., *J. Appl. Phycol.*, 15:345-349, 2003; Jiang et al., *Plant Cell Rep.*, 21:1211-1216, 2003; Qin et al., *High Technol. Lett.*, 13:87-89, 2003). Further nonlimiting examples of enzymes that can be used for detecting a colored or labeled product include aryl sulfatase (Davies et al. (1992) *Nucl. Acids. Res.* 20:2959-2965; Hallman and Sumper (1994) *Eur. J Biochem.* 221:143-150), alkaline phosphatase (El-Sankary et al. (2001) *Drug Metab. Disposition* 29:1499-1504), and chloramphenicol acetyl transferase (Sekiya et al. (2000) *J. Biol. Chem.* 275:10738-10744).

A selectable marker can provide a means to obtain heterokont cells, algal cells, yeast cell, plant cells or any combination that express the marker and, therefore, include the synthetic chromosome construct, and can therefore be useful as a component of a synthetic chromosome of the present disclosure. Examples of selectable markers include genes encoding deaminase, such as the deaminase from *Aspergillus terreus*, which confers resistance to Blasticidin S (Tamura, *Biosci. Biotechnol. Biochem.* 59: 2336-2338, 1995), as well as genes conferring resistance to antibiotics such as bleomycin, gentamycin, glyphosate, hygromycin, kanamycin, neomycin, nourseothricin, phleomycin, puromycin, spectinomycin, and streptomycin. For example, neomycin phospho-transferase confers resistance to the aminoglycosides neomycin, kanamycin and paromycin (Herrera-Estrella, *EMBO J.* 2:987-995, 1983) and the "hygro" gene confers resistance to hygromycin (Marsh, *Gene* 32:481-485, 1984). Several different antibiotic resistance genes have been used successfully for selection of microalgal transformants, including blastocydin, bleomycin (see, for example, Apt et al., 1996, supra; Fischer et al., 1999, supra; Fuhrmann et al., *Plant J.*, 19, 353-61, 1999, Lumbreras et al., *Plant J.*, 14(4):441-447, 1998; Zaslayskaia et al., *J. Phycol.*, 36:379-386, 2000), spectinomycin (Cerutti et al., *Genetics*, 145: 97-110, 1997; Doetsch et al., *Curr. Genet.*, 39, 49-60, 2001; Fargo, *Mol. Cell. Biol.*, 19:6980-90, 1999), streptomycin (Berthold et al., *Protist*, 153:401-412, 2002), paromomycin (Jakobiak et al., *Protist*, supra.; Sizova et al., *Gene*, 277: 221-229, 2001), nourseothricin (Zaslayskaia et al., 2000, supra), G418 (Dunahay et al., 1995, supra; Poulsen and Kroger, *FEBS Lett.*, 272:3413-3423, 2005, Zaslayskaia et al., 2000, supra), hygromycin (Berthold et al., 2002, supra), chloramphenicol (Poulsen and Kroger, 2005, supra), and others. Additional selectable markers for use in microalgae can be markers that provide resistance to kanamycin and amikacin (Bateman, *Mol. Gen. Genet.* 263:404-10, 2000), zeocin and phleomycin (e.g., ZEOCIN™ pheomycin D1) (Stevens, *Mol. Gen. Genet.* 251:23-30, 1996), and paramomycin and neomycin (Sizova et al., 2001, supra).

Also considered are genes conferring resistance to antimetabolites, such as methotrexate, e.g., genes encoding dihydrofolate reductase, (Reiss, *Plant Physiol. (Life Sci. Adv.*) 13:143-149, 1994); trpB, which allows cells to utilize indole in place of tryptophan; hisD, which allows cells to utilize histinol in place of histidine (Hartman, *Proc. Natl. Acad. Sci., USA* 85:8047, 1988); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, 1987, In: *Current Communications in Molecular Biology*, Cold Spring Harbor Laboratory ed.). Additional selectable markers include those that confer herbicide resistance, for example, phosphinothricin acetyltransferase gene, which confers resistance to phosphinothricin (White et al., *Nucl. Acids Res.* 18:1062, 1990; Spencer et al., *Theor. Appl. Genet.* 79:625-631, 1990), a mutant EPSPV-synthase, which confers glyphosate resistance (Hinchee et al., *BioTechnology* 91:915-922, 1998), a mutant acetolactate synthase, which confers imidazolione or sulfonylurea resistance (Lee et al., *EMBO J.* 7:1241-1248, 1988), a mutant psbA, which confers resistance to atrazine (Smeda et al., *Plant Physiol.* 103:911-917, 1993), or a mutant protoporphyrinogen oxidase (see U.S. Pat. No. 5,767,373), or other markers conferring resistance to an herbicide such as glufosinate, sulfonamide, or phosphinothricin or sulfonylurea (see, for example, Maliga et al., *Methods in Plant Molecular Biology*, Cold Spring Harbor Laboratory Press, 1995, page 39). Genes conferring resistance to antibiotics such as tetracycline; ampicillin, kanamycin, and chloramphenicol can be used for selection of the synthetic chromosome construct in prokaryotes such as *E. coli*.

Auxotrophic markers are selectable markers that can be used in a host having a mutation in a gene encoding a metabolic enzyme, such as, for example, arginosuccinate lyase, for arginine synthesis, nitrate reductase for nitrogen assimilation (ability to utilize nitrate), thi10 for thiamine biosynthesis, and nic for nicotinamide biosynthesis.

Negative selection markers that may be included on a DNA transfer construct, include, without limitation, thymidine kinase (Lupton et al. (1991) *Molecular and Cellular Biology* 11: 3374-3378), DAOO (Erikson et al. (2004) *Nature Biotechnology* 22: 455-458) URA, and sacB (Quenee et al. (2005) *Biotechniques* 38: 63-67).

A DNA transfer construct of the present invention typically will be a plasmid. The nucleic acid molecule to be transferred by conjugation may be large, for example at least about 1 kb, 10 kb, 25 kb, 50 kb, 75 kb, 100 kb, 125 kb, 150 kb, 175 kb, 200 kb, 250 kb, 300 kb, 350 kb, 400 kb, 500 kb, 600 kb, 700 kb, 800 kb, 900 kb or 1 Mbp. Additionally, the nucleic acid molecules of the present invention may be about 1 kb to 10 kb, about 1 kb to 25 kb, 1 kb to 50 kb, about 1 kb to 75 kb, 1 kb to 100 kb, about 10 kb to 125 kb, 10 kb to 150 kb, about 10 kb to 175 kb, 10 kb to 200 kb, about 20 kb to 250 kb, 30 kb to 300 kb, about 30 kb to 350 kb, 40 kb to 400 kb, about 40 kb to 450 kb, 50 kb to 500 kb, about 100 kb to 500 kb, 100 kb to 600 kb, about 100 kb to 700 kb, 200 kb to 800 kb, about 200 kb to 900 kb and 100 kb to 1 Mbp.

The nucleic acid molecule can include a gene encoding a metabolic enzyme, structural protein, cytoskeleton protein, kinase, phosphatase, nucleotide cyclase, phosphodiesterase, transcriptional regulator, transcriptional activator, transporter, secretory protein, ion channel, porin, receptor, photosynthetic protein, chaperonin, ribosomal protein, or nuclear scaffold protein. A gene included on a DNA transfer construct can be a gene derived from the host species into which the DNA transfer construct is introduced, or can be derived from another species. In various examples, a DNA transfer construct as provided herein can include a gene encoding a meganuclease, including an engineered meganuclease (Smith et al. (2006) *Nucl. Acids Res.* 34: e149), a zinc finger nuclease (Durai et at (2005) *Nucl. Acids Res.* 33: 5978-5990), a TALEN (Christian et al. (2010) *Genetics* 186: 757-761), an RNA-guided endonuclease such as a cas protein (e.g., cas9 or a variant or homolog thereof, see for example, Jinek et al. (2012) *Science* 337:816-821; Makarova et al. (2006) *Biology Direct* 1:7; US20140068797; all herein incorporated by reference in their entireties), a recombinase, an integrase, a topoisomerase, or a transposase. A nuclease, recombinase, integrase, topoisomerase or transposase can be operably linked to a heterologous promoter that can optionally be inducible. In some examples, a nucleic acid molecule as provided herein can include two or more genes that are not found on the same naturally-occurring chromosome.

The RNA-guided nuclease can be, for example, a Cas protein, such as a Cas9 protein, of which a large number have been identified, and can be for example a Cas9 protein of *Streptococcus pyogenes, Streptococcus thermophilus*, or *Neisseria meningitidis*. Other Cas proteins of interest includes, without limitation, the Cpf1 RNA-guided endonuclease (Zetsche et al. (2015) *Cell* 163:1-13) as well as the C2c1, C2c2, C2c3 RNA-guided nucleases (Shmakov et al. (2015) *Molecular Cell* 60:1-13. The nucleic acid sequence encoding the Cas protein can be codon optimized for the host cell of interest. In some instances, a Cas9 protein encoded by a nucleic acid molecule introduced into a host cell can comprise at least one mutation with respect to a wild-type Cas9 protein; for example, the Cas9 protein can be inactivated in one of the cleavage domains of the protein resulting in a "nickase" variant. Nonlimiting examples of mutations include D10A, H840A, N854A, and N863A.

A DNA transfer construct in some examples can have at least one gene that is operably linked to a promoter other than its natural promoter, i.e., a promoter that is heterologous with respect to the gene. The promoter can be a promoter sequence isolated from the intended recipient species or a variant thereof. DNA transfer constructs that include a gene of interest for expression in a host cell can include regulatory sequences such as but not limited to promoter sequences and terminator sequences that are operably linked to the gene of interest. Such regulatory sequences, for example, promoter sequences, may be regulatable, e.g., inducible by environmental conditions or media components. The promoters may be from the same genus or species as the host organism, or may be of a different species than the host organism.

A variety of known promoter sequences can be usefully deployed for transformation systems of microalgal and heterokont species. For example, the promoters commonly used to drive transgene expression in microalgae include various versions of the of cauliflower mosaic virus promoter 35S (CaMV35S), which has been used in both dinoflagellates and *chlorophyta* (Chow et al, *Plant Cell Rep.*, 18:778-780, 1999; Jarvis and Brown, *Curr. Genet.*, 317-321, 1991; Lohuis and Miller, *Plant J.*, 13:427-435, 1998). The SV40 promoter from simian virus has also reported to be active in several algae (Gan et al., *Appl. Phycol.,* 151 345-349, 2003; Qin et al., *Hydrobiologia* 398-399, 469-472, 1999). The promoters of RBCS2 (ribulose bisphosphate carboxylase, small subunit) (Fuhrmann et al., *Plant J.,* 19:353-361, 1999) and PsaD (abundant protein of photosystem I complex; Fischer and Rochaix, *FEBS Lett.* 581:5555-5560, 2001) from *Chlamydomonas* can also be useful. The fusion promoters of HSP70A/RBCS2 and HSP70A/β2TUB (tubulin) (Schroda et al., *Plant J.,* 21:121-131, 2000) can also be useful for an improved expression of transgenes, in which HSP70A promoter may serve as a transcriptional activator when placed upstream of other promoters. High-level expression of a gene of interest can also be achieved in heterokonts, for example diatoms species, under the control of a promoter of an fcp gene encoding a diatom fucoxanthin-chlorophyll a/b binding protein (Falciatore et al., *Mar. Biotechnol.,* 1:239-251, 1999; Zaslayskaia et al., *J. Phycol.* 36:379-386, 2000) or the vcp gene encoding a eustigmatophyte violaxanthin-chlorophyll a/b binding protein (see U.S. Pat. No. 8,318,482). If so desired, inducible promoters can provide rapid and tightly controlled expression of genes in transgenic microalgae. For example, promoter regions of the NR genes encoding nitrate reductase can be used as such inducible promoters. The NR promoter activity is typically suppressed by ammonium and induced when ammonium is replaced by nitrate (Poulsen and Kroger, *FEBS Lett* 272: 3413-3423, 2005), thus gene expression can be switched off or on when microalgal cells are grown in the presence of ammonium/nitrate. Other regulatable promoters from *Nannochloropsis* include those disclosed in U.S. Patent Application Publication No. US2013/0023035, incorporated by reference herein. Additional algal promoters that can find use in the constructs and transformation systems provided herein include those disclosed in U.S. Pat. No. 8,709,766; U.S. Patent Application Publication No. US2013/0323780; U.S. Pat. No. 8,883,993; and U.S. Patent Application Publication No. 2014/0363892; all incorporated by reference herein.

Alternatively or in addition, a DNA transfer construct as provided herein can include at least one engineered site that is recognized by a nuclease, integrase, or recombinase. An engineered nuclease, integrase, or recombinase site is a sequence recognized by a nuclease, integrase, or recombinase that is not naturally occurring at the position it is designed into on the synthetic chromosome construct but is introduced by DNA synthesis or cloning techniques. Examples of sites that may be engineered into a synthetic chromosome that are recognized by recombinases and integrases include, without limitation, lox sites, FLP sites, and att sites. A nuclease can be, as nonlimiting examples, a meganuclease, a zinc finger nuclease (Beerli et al. (1998) *Proc. Nat. Acad. Sci.* 95:14628-14633; Townsend et al. (2009) *Nature* 459:442-445; Shukla et al. (2009) *Nature* 459:437-441, or a cas nuclease, e.g., a cas9 nuclease (WO2013142578; US20140068797; U.S. Pat. No. 8,697, 359), including a variant of a cas9 nuclease (e.g., a "nickase" D10A cas9 mutant; see for example Cong et al. (2013) *Science* 339:819-823; US20140068797). A recombinase can be, as nonlimiting examples, a cre recombinase, a FLP recombinase, or an R recombinase (Srivastava & Ow (2004) *Trends Biotechnol.* 22:627-629; Zhang et al. (2003) *Theor. Appl. Genetics* 107:1157-1168; Wang et al. (2005) *Transgenic Res.* 14:605-614)), or any of the phage recombinases disclosed in Fogg et al. (2014) *J Mol. Biol.* For example, a synthetic chromosome can include one or more lox sites (Albert et al. (1995) *Plant J.* 7:649-659; Vega et al. (2008) *Plant Mol. Biol.* 66:587-598) FRT sites, RS sites, or att sites or can include an engineered PAM sequence that is recognized by a cas9-type nuclease (for example, NG, NGG, NGGNG, NNAAAAW, NNNNACA, NNNNGATT, or GNNNCNNA; see, for example, Fonfara et al. (2013) *Nucl. Acids Res.* doi: 10.1093/nar/gkt1074; Chylinski et al. (2013) *RNA Biol.* 10:726-737; Makarova et al. (2014) *Nat. Rev. Microbiol.* 9:467-477; U.S. Pat. No. 8,697,359; and U.S. Patent Application Publication US2014/0068797; all incorporated herein by reference in their entireties). Nuclease sites or recombination sites can be designed and incorporated into primers or synthesized genes, and can be designed, in some examples, to flank a marker gene or reporter gene such that the marker gene or reporter gene can be removed or exchanged for another gene, for example, a gene encoding a metabolic enzyme (see, for example, Gleave et al. (1999) *Plant Mol. Biol.* 40:223-235; Radhakrishnan & Srivastava (2005) *Plant Cell Rep.* 23:721-726; Ebinuma et al. (2005) *Methods Mol. Biol.* 286:237-254).

In another aspect, the present invention provides a method of delivering a nucleic acid molecule to an algal cell comprising: contacting the alga cell with a bacterium comprising a DNA transfer construct containing the nucleic acid molecule, wherein the transfer construct becomes established as an episome in the algal cell, thereby delivering the nucleic acid to the algal cell. The method can use any of the constructs, maintenance cassettes, bacterial donor strains, recipient strains, and methods described herein, e.g., as disclosed hereinabove. In one aspect, the algal cell is a green algae (chlorophyte), red algae (rhodophyte), diatom (bacillariophyte), pelagophyte, prasinophyte, glaucophyte, chlorarachniophyte, euglenophyte, chromophyte, xanthophyte, or dinoflagellate. In a particular aspect, the algal cell is green algae (chlorophyte) or a diatom (bacillariophyte). For example, the algal cell can be a member of the genera including *Amphora, Ankistrodesmus, Aplanochytrium, Asteromonas, Aureococcus, Boekelovia, Bolidomonas, Borodinella, Botrydium, Botryococcus, Bracteacoccus, Carteria, Chaetoceros, Chlamydomonas, Chlorella, Chlorococcum, Chlorogonium, Chrococcidiopsis, Chroomonas, Chrysophyceae, Chrysosphaera, Cricosphaera, Cryptheco-dinium, Cryptococcus, Cryptomonas, Cyanidioschyzon, Cyclotella, Cylindrotheca, Cymbella, Desmodesmus, Dunaliella, Elina, Ellipsoidon, Emiliania, Eremosphaera, Ernodesmius, Euglena, Eustigmatos, Fragilaria, Fragilariopsis, Franceia, Gloeothamnion, Haematococcus, Hantzschia, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phaeodactylum, Picochlorum, Platymonas, Pleurochrysis, Pleurococcus, Porphyridium, Prototheca, Pseudochlorella, Pseudoneochloris, Pseudostaurastrum, Pyramimonas, Pyrobotrys, Rholdella, Scenedesmus, Schizochlamydella, Skeletonema, Spirulina, Spyrogyra, Staurastrum, Stichococcus, Tetrachlorella, Tetraselmis, Thalassiosira, Tribonema, Vaucheria, Vibrio, Viridiella, Vischeria,* or *Volvox.* In some examples, the algal cell is *Nannochloropsis, Chlamydomonas, Tetraselmis, Haematococcus, Chlorella, Parachlorella,* or *Desmodesmus.* In some examples, the algal cell is a diatom, such as a species of any of the genera *Achnanthes, Amphora, Chaetoceros, Coscinodiscus, Cylindrotheca, Cyclotella, Cymbella, Fragilaria, Fragilariopsis, Hantzschia, Navicula, Nitzschia, Pavlova, Pseudo-Nitzschia, Phaeodactylum, Psammodictyon, Skeletonema, Thalassionema,* and *Thalassiosira.*

The donor bacterium can be any bacterium that has the conjugative functions enabling transfer of the DNA transfer construct to another cell. For example, the donor bacterium can be a species of any of the genera *Escherichia, Actinomycetes, Alcaligenes, Bacillus, Corynebacter, Envinia, Flavobacterium, Helicobacter, Klebsiella, Lactobacillus, Moraxella, Neisseria, Paracoccus, Pseudomonas, Salmonella, Shigella, Streptococcus, Streptomyces, Vibro, Agrobacterium, Rhizobium, Sinorhizobium, Mesorhizobium*, or *Ensifer*. and *Candidatus*. In exemplary embodiments, the bacterium is *E. coli*.

The DNA transfer construct can include a nucleic acid molecule that a polypeptide and/or a functional RNA. In one aspect, the nucleic acid molecule is at least about 1 kb, 10 kb, 25 kb, 50 kb, 75 kb, 100 kb, 125 kb, 150 kb, 175 kb, 200 kb, 250 kb, 300 kb, 350 kb, 400 kb, 500 kb, 600 kb, 700 kb, 800 kb, 900 kb or 1 Mbp. In a specific aspect, the nucleic acid molecule is at least about 50 kb or at least about 100 kb. In an additional aspect, the nucleic acid molecule is heterologous.

The DNA transfer construct can be any described herein. For example, the DNA transfer construct can comprise a maintenance cassette, an origin of transfer, and optionally a selectable marker. In one aspect, the maintenance cassette comprises a centromere sequence and an autonomous replication sequence (ARS). In a specific aspect, the maintenance cassette comprises a yeast, e.g., *Saccharomyces* centromere sequence and ARS, for example, CEN6-ARSH4 (SEQ ID NO:4) or CEN6-ARSH4-111153 (SEQ ID NO:5), or a nucleotide sequence having at least 80%, at least 85%, at least 90%, at least 95%, at least 96%, at least 97%, at least 98%, at least 99% identity to at least 200, at least 300, at least 400, at least 500, at least 600, at least 700, at least 800, at least 900, at least 1000, at least 1100, at least 1200, at least 1300 contiguous nucleotides of SEQ ID NO:4 or SEQ ID NO:5. In an additional aspect, the selectable marker may be an antibiotic resistance gene, a gene encoding a polypeptide conferring resistance to a toxin, an auxotrophic marker, and a combination thereof. In some aspects, the antibiotic resistance gene confers resistance to antibiotics including blasticidin, bleomycin, gentamycin, glyphosate, hygromycin, kanamycin, neomycin, nourseothricin, phleomycin, puromycin, spectinomycin, zeocin, and streptomycin. In a further aspect, the plasmid further comprises a promoter, a reporter gene, a regulatory element or a combination thereof. In one aspect, the transformation efficiency is increased at least about 100-fold using a DNA transfer construct that includes a maintenance cassette as disclosed herein as compared to a plasmid without a maintenance cassette. In an aspect, the nucleic acid molecule is maintained as a replicating extrachromosomal vector in the algal cell.

In an additional aspect, the present invention provides a method of producing a recombinant algal cell comprising contacting the algal cell with a bacteria comprising a plasmid containing a nucleic acid molecule, wherein the plasmid remains episomal for at least ten, at least twenty, or at least thirty generations, thereby producing a recombinant algal cell. The plasmid in some examples remains episomal least ten, at least twenty, or at least thirty generations in the absence of selection. The method can utilize any of the methods, constructs, donor cells, and recipient cells disclosed herein. In one aspect, the algal cell is green algae (chlorophytes), red algae (rhodophytes), diatoms (bacillariophytes), pelagophytes, prasinophytes, glaucophytes, chlorarachniophytes, euglenophytes, chromophytes, xanthophytes, and dinoflagellates. In another aspect, the algal cell is green algae (chlorophytes) or a diatom (bacillariophytes).

In an additional aspect, the algal cell is a member of the genera including *Amphora, Ankistrodesmus, Aplanochytrium, Asteromonas, Aureococcus, Boekelovia, Bolidomonas, Borodinella, Botrydium, Botryococcus, Bracteacoccus, Carteria, Chaetoceros, Chlamydomonas, Chlorella, Chlorococcum, Chlorogonium, Chrococcidiopsis, Chroomonas, Chrysophyceae, Chrysosphaera, Cricosphaera, Cryptheco-dinium, Cryptococcus, Cryptomonas, Cyclotella, Cyanidioschyzon, Desmodesmus, Dunaliella, Elina, Elhpsoidon, Emiliania, Eremosphaera, Ernodesmius, Euglena, Eustigmatos, Fragilaria, Fragilariopsis, Franceia, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phaeodactylum, Picochlorum, Platymonas, Pleurochrysis, Pleurococcus, Porphyridium, Prototheca, Pseudochlorella, Pseudoneochloris, Pseudostaurastrum, Pyramimonas, Pyrobotrys, Rholdella, Scenedesmus, Schizochlamydella, Skeletonema, Spirulina, Spyrogyra, Staurastrum, Stichococcus, Tetrachlorella, Tetraselmis, Thalassiosira, Tribonema, Vaucheria, Vibrio, Viridiella, Vischeria*, or *Volvox*. In specific aspects, the algal cell is *P. tricornutum, T. pseudonana*, or *Nannochloropsis, Chlamydomonas, Tetraselmis, Haematococcus Chlorella, Parachlorella*, or *Desmodesmus*. In an exemplary embodiment, the bacterium is *E. coli*.

In a further aspect, the present invention provides for a kit for transforming an algal cell comprising a nucleic acid molecule comprising an origin of transfer and a selectable marker, and *E. coli* cells comprising genes required for conjugation. The *E. coli* cells can be provided in a solution comprising a cryoprotective agent such as glycerol or DMSO. For example, the *E. coli* cells can be provided in a solution comprising at least 5%, at least 10%, at least 15%, or at least 20% glycerol.

The nucleic acid molecule provided in the kit can be a plasmid. The nucleic acid molecule can further comprisean ARS, such as disclosed herein, a centromere sequence, such as any disclosed herein, or a maintenance cassette as disclosed herein. In one aspect, the plasmid includes a maintenance cassette that comprises a centromere sequence and an ARS. In a specific example, the maintenance cassette comprises a yeast maintenance cassette, e.g., CEN6-ARSH4 (SEQ ID NO:4) or a sequence having at least 80%, at least 85%, at least 90%, at least 95%, at least 96%, at least 97%, at least 98%, at least 99% identity to at least 200, at least 300, at least 400, at least 500, at least 600, at least 700, at least 800, at least 900, at least 1000, at least 1100, at least 1200, at least 1300 contiguous nucleotides of SEQ ID NO:4 or SEQ ID NO:5. In an additional aspect, the selectable marker may be an antibiotic resistance gene, a gene encoding a polypeptide conferring resistance to a toxin, an auxotrophic marker, and a combination thereof. In some aspects, the antibiotic resistance gene confers resistance to antibiotics including bleomycin, gentamycin, glyphosate, hygromycin, kanamycin, neomycin, nourseothricin, phleomycin, puromycin, spectinomycin, and streptomycin. In an additional aspect, the plasmid further comprises a promoter, a reporter gene, a regulatory element or a combination thereof.

The kit can further optionally include at least one media formulation for diluting, responding, or plating bacterial cells, algal cells, or both. The kit can further include instructions for use.

As described in the examples below, a conjugation-based protocol to transfer and stably maintain replicating transfer constructs p0521 and p0521s in *Phaeodactylum tricornutum* was developed. Further, it is shown that this system can be used to introduce DNA into two species of diatoms (*P. tricornutum* and *Thalassiosira pseudonana*) by conjugation with *E. coli*. Transferred DNA was maintained on an extra-chromosomal vector when the transferred plasmid contained the yeast maintenance cassette (CEN6-ARSH4, SEQ ID NO:4 or CEN6-ARSH4-HIS3, SEQ ID NO:5). The region of the p0521s vector responsible for maintenance as an extra-chromosomal vector was identified. Surprisingly, this region "the yeast maintenance cassette" (CEN6-ARSH4-HIS3, SEQ ID NO:5, approximately 1.4 kb) is the sequence that allows for vector replication and selection in the yeast *Saccharomyces cerevisiae*. Several aspects of these data are unexpected. First, due to the silica outer layer characteristic of diatoms, it is unexpected that bacterial conjugation would be successful in transferring DNA to the diatom. However, as discussed above and in more detail in the Examples below, the presently described methods were successful at using bacterial conjugation to transfer DNA to two diatoms, *P. tricornutum* and *T. pseudonana*. Further, given the species specific nature of centromere sequences it would not be expected that sequences not derived from the host species, such as the yeast sequences used in the present constructs, would function in an algal cell as is shown in the data.

The invention in all its aspects is illustrated further in the following Examples. The Examples do not, however, limit the scope of the invention, which is defined by the appended claims.

EXAMPLES

Example 1. Development of an Extra-Chromosomal Replicating Vector for Diatoms To develop an extra-chromosomal replicating vector for diatoms, experiments were designed to identify sequences that can function as a centromere or origin of replication in *P. tricornutum*. Classical centromere signatures, based on DNA composition, are absent from putative full length *P. tricornutum* chromosomes. Therefore, an experimental workflow based on iterative transformation of *P. tricornutum* with large cloned fragments (24-94 kb) of a scaffold of chromosome 25, which is fully assembled between telomeres, was implemented. Molecules maintained as episomes in *P. tricornutum* could be extracted and successfully reintroduced into *E. coli* by electroporation (a technique defined as "episome rescue" henceforth). Episome rescue cycles were performed by 1) growing diatom exconjugant colonies in small liquid cultures, 2) extracting diatom DNA, 3) electroporating *E. coli* with the diatom DNA, and 4) extracting and analyzing plasmids from *E. coli* using standard techniques, including gel electrophoresis, PCR, sequencing, and/or hybridization.

*P. tricornutum* chromosome fragments were cloned into vectors that could be replicated in yeast or *E. coli* using TAR cloning (see Karas et al. *J Biol Eng* (2013) 7:30; Noskov et al. (2001) *Nucl Acids Res.* 29:6 e32). Vectors for cloning *P. tricornutum* DNA fragments were constructed as in Karas et al. (Ibid), where the vector pBK-RBYV (SEQ ID NO:6) was used as the cloning plasmid. The pBK-RBYV vector included a pCCBac1-LCyeast backbone (SEQ ID NO:7); the shble (bleomycin resistance) cassette (SEQ ID NO:8) for expression in *Phaeodactylum* that included a *Phaeodactylum* fucoxanthin chlorophyll a/c binding protein (Fcp) F promoter (SEQ ID NO:9) followed by a sequence encoding the *Streptoalloteichus hindustanus* (Sh) bleomycin resistance gene (SEQ ID NO:10) followed by a *Phaeodactylum* FcpA gene terminator (SEQ ID NO:11); an OriT sequence (SEQ ID NO:12), allowing transfer of the cargo plasmid; and a URA3 marker (SEQ ID NO:13) for selection in yeast.

Several diatom colonies were obtained from transformations with the chromosome 25 fragments using electroporation and polyethylene glycol (PEG)-mediated transformation methods to prevent shearing of the large plasmids. *P. tricornutum* transformation efficiency using the PEG-mediated methods was low and often yielded only 1 colony per transformation with an approximate efficiency of $1 \times 10^{-8}$. Of the episomes rescued from these colonies, a plasmid containing the *P. tricornutum* chromosome 25 region 25-1, p0521, and a spontaneously minimized version of p0521, p0521s (Genbank Accession No. KP745602.1, GI:825091387) were chosen for further study; both plasmids were rescued successfully after a second round of *P. tricornutum* transformation.

Delivery of p0521 and p0521s to *P. tricornutum* was improved by developing a conjugation-based method that transferred p0521s at an efficiency of $4.0 \times 10^4$ diatom cells, a transformation efficiency significantly higher than was observed in our attempts at electroporation and PEG-mediated transformations and higher than reported electroporation and particle bombardment efficiencies ($4.5 \times 10^{-5}$-$10^{-7}$). *P. tricornutum* cells were prepared for conjugation with *E. coli* by growing *P. tricornutum* in liquid culture, adjusting the concentration of the culture to $1.0 \times 10^8$ cells/mL, and plating 250 μL of the cell suspension on ½L1, 1% agar plates. The plates were then incubated in the light for 4 days. L1 media (500 μL) was then added to the plates and cells were scraped off of the plate surface and counted using a hemocytometer. The cell concentration was adjusted to $5 \times 10^8$ cells/mL. *E. coli* cells carrying the conjugation plasmid pRL443 (Elhae et al. (1997) *J. Bacteriol.* 179:1998-2005; Addgene plasmid #70261 (addgene.com)) and a cargo plasmid that included the *Phaeodactylum* sequences were prepared for conjugation by growing a 50 mL culture at 37° C. to an OD600 of 0.8-1.0 and then spinning down the cells for 10 min at 3,000×g. The *E. coli* cells were resuspended in 500 μL of SOC media.

For conjugation of *P. tricornutum* with *E. coli*, 200 μL of *P. tricornutum* cells were moved to a 1.5 mL microfuge tube and then 200 μL of *E. coli* cells were added and mixed by pipetting up and down few times. Next the cell mixture was plated on ½×L1, 5% LB, 1% agar plates and incubated for 90 minutes at 30° C. in the dark, after which the plates were moved to 18° C. in the light allowed to grow without selection for 2 days. After two days, 1 mL of L1 media was added to the plates and cells were scraped of the plates. 200 μL of the scraped cells was plated on ½×L1, phleomycin 20 μg/mL, 1% agar plate and incubated at 18° C. in the light. Diatom colonies appeared after 10-14 days.

Results of multiple transformation experiments varying co-incubation times, amounts of *Phaeodactylum* and *E. coli* cells, and other parameters are provided in the table of FIGS. 1A-J. The transformation protocols included incubation of *E. coli* carrying the cargo plasmid and diatom cells at 30° C., a temperature significantly higher than the optimal growth temperature of *Phaeodactylum* (approximately 18° C.) and closer to the growth optimum temperature of *E. coli* (37° C.). In various experiments, incubation at the elevated temperature (30° C.) was from thirty to one hundred twenty minutes, and transformants were obtained at all incubation temperatures. Following the 0.5 to 2 hour incubation at 30°

C., the cell mixtures (bacterial cells and diatom cells) were incubated in the light at 18° C. for a period of one to two days. Following this second incubation, the cell mixture was subjected to selection on phleomycin, an antibiotic to which the ShBle cassette (SEQ ID NO:8), which included a eukaryotic promoter only (FcpF promoter, SEQ ID NO:9) conferred resistance.

Figure 2B:
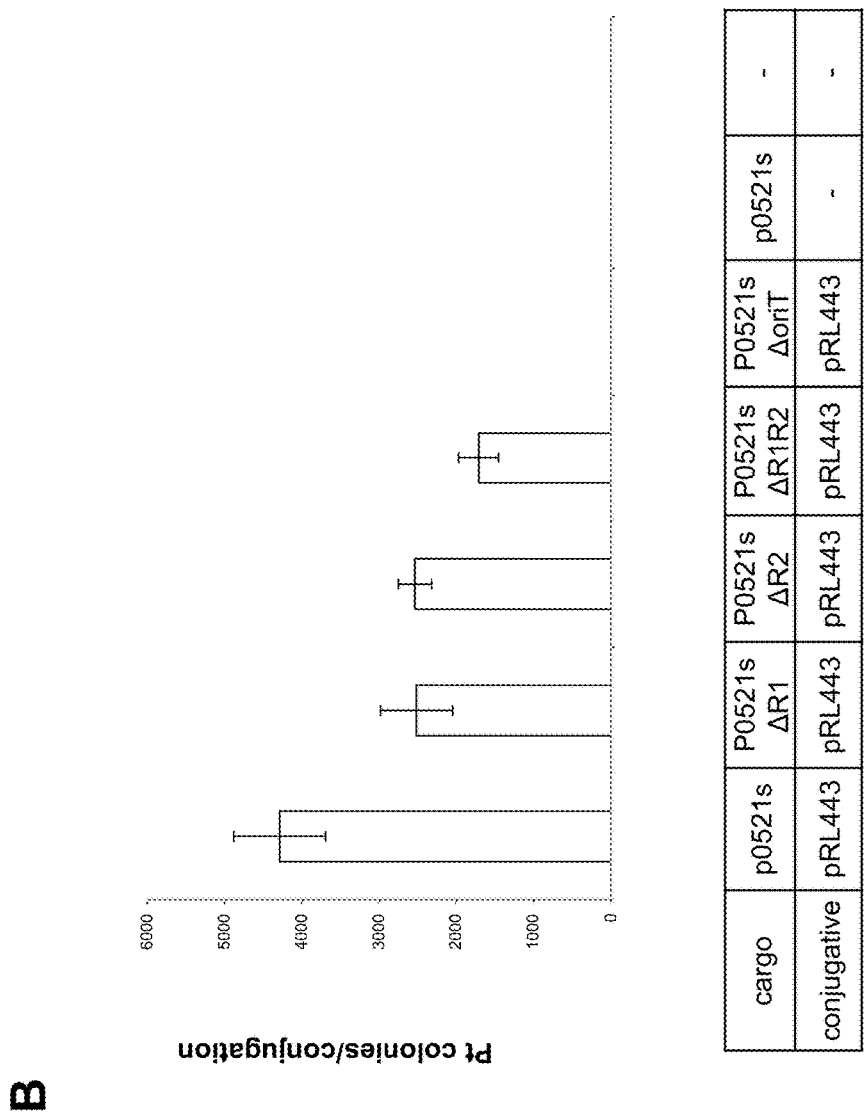

Trans-kingdom conjugation has been demonstrated previously for yeasts and mammalian cells, but never before in the Stramenopile (heterokont) lineage. Two important controls verified that conjugation was the mechanism of gene transfer: 1) phleomycin-resistant P. tricornutum colonies were only obtained when E. coli contained the conjugative plasmid (RP4 variant pRL443, see Elhae et al. (1997) J. Bacteriol. 179:1998-2005; available at Addgene (addgene.org) as plasmid #70261), and 2) the origin of transfer (oriT, SEQ ID NO:12) on the mobilizable cargo plasmid (e.g. p0521s, FIG. 2A) was essential to obtain phleomycin-resistant P. tricornutum colonies (FIG. 2B). Physical association between E. coli and diatoms, a necessary prerequisite for conjugation, was identified by scanning electron microscope analysis. It was also verified that rescued episomes were from P. tricornutum and not from any E. coli that might have remained with the P. tricornutum cells after the conjugation process: Streaking P. tricornutum exconjugant cultures on LB plates and incubating the plates at 37° C. did not yield any E. coli colonies. This confirmed that any E. coli culture containing the plasmid donor was eliminated during selection of P. tricornutum exconjugants.

Figures 3A, 3B:
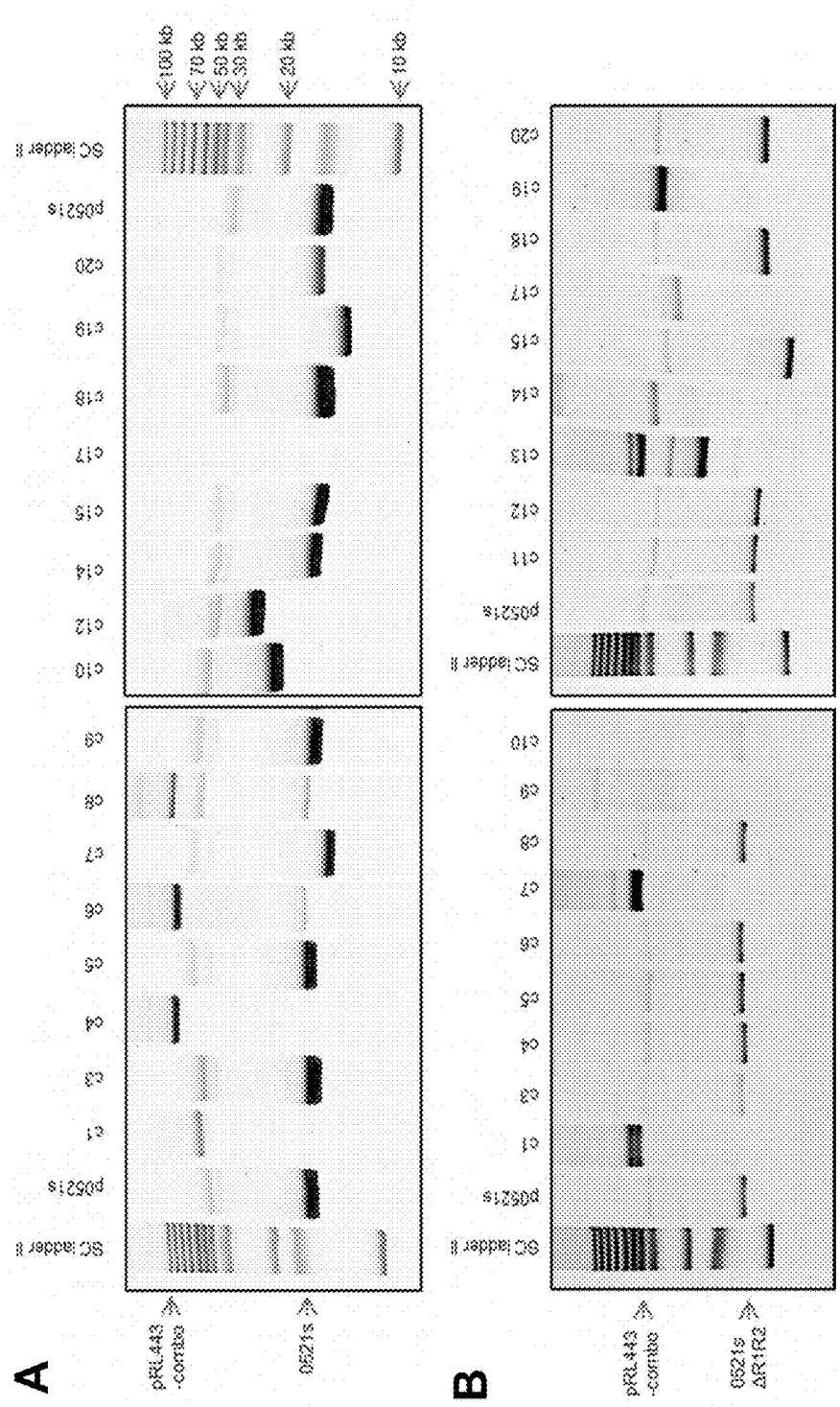
FIGS. 3A-B show episomes rescued from *P. tricornutum* exconjugant lines. A) Agarose gel showing electrophoresed rescued plasmids isolated from *E. coli* cells that were electroporated with DNA isolated from 16 exconjugant *P. tricornutum* lines containing plasmid p0521s. B) Agarose gel showing electrophoresed rescued plasmids isolated from *E. coli* cells that were electroporated with DNA isolated from 16 exconjugant *P. tricornutum* lines containing plasmid p0521s-ΔR1R2 (lacking *P. tricornutum* scaffold 25 sequences).

After episome rescue and analysis of the resulting plasmids, approximately 30% of P. tricornutum lines were found to have plasmids of the same size as the original starting plasmid (FIGS. 3A and 3B). One class of incorrectly sized plasmids, chimeras between the conjugative and the cargo plasmids (RP4 and p0521s, respectively, bands corresponding to the chimeras are denoted "RPL443-combo" in FIG. 3A and FIG. 3B) was later eliminated by using a variant of the RP4 conjugative plasmid (pTA-MOB) lacking the oriT sequence (SEQ ID NO:12). A second class of incorrectly sized plasmids was occasionally recovered with minor size differences. Although sequencing of several plasmids identified small deletions and a retrotransposon element insertion event, plasmids were stably maintained once identified as having the correct size as discussed below.

Example 2. Diatom Episome Maintenance

To identify the elements of p0521s allowing replication in diatoms, variants either lacking the P. tricornutum-derived region or lacking other components of the plasmid were engineered. First, two distinct sub-fragments within the 2.5-kb P. tricornutum 25-1 sequence in cargo plasmid p0521s, R1 and R2 (FIG. 2A), which together make up the entire 2.5-kb P. tricornutum 25-1 sequence of the p0521s plasmid, were separately included in derivative cargo plasmid constructs. Compared to conjugation with the full length p05201s plasmid, deletion of either of the two sub-fragments that make up the 2.5-kb region led to approximately half as many P. tricornutum exconjugants per mating (FIG. 2B). Surprisingly, complete removal of the P. tricornutum-derived region still yielded exconjugants at high efficiency (FIG. 2B), although plasmid p0521s, containing the P. tricornutum-derived region, yielded approximately 2.5-fold more ex-conjugants than the version with all of the P. tricornutum 2.5-kb sequence deleted. Similar numbers of correctly sized plasmids were rescued regardless of the presence of the P. tricornutum region (7/20 or 8/20 for p0521s or p0521s-ΔR1R2, respectively) (Table 1). Thus, while P. tricornutum fragments appeared to modestly increase conjugation efficiency, they were not essential for this process and therefore, another sequence on the cargo plasmid was responsible for replication of the introduced construct in P. tricornutum.

TABLE 1

Rescue of plasmid constructs introduced into Algae by Conjugation

| Plamids used in Conjugation | Total # P. tricornutum colonies | # Algal colonies from which a plasmid was rescued in E. coli | # Algal colonies from which correct plasmid was rescued in E. coli |
|---|---|---|---|
| p0521s/pRL443 | 5,660 | 16/20 | 7/20 |
| p0521s ΔR1R2/pRL443 | 895 | 18/20 | 8/20 |
| p0521s/pTA-MOB | 10,628 | 18/20 | 14/20 |
| p0521s ΔR1R2/pTA-MOB | 4,915 | 17/20 | 11/20 |
| p0521se/pTA-MOB | 1,900 | 17/20 | 7/20 |
| pPtPuc1/pTA-MOB | 2,750 | 20/20 | 8/20 |
| pPtPuc2/pTA-MOB | 64 large, 373 small | 0/20 | 0/20 |
| pPtPuc3/pTA-MOB | 2, 130 | 19/20 | 10/20 |
| pPtPuc4/pTA-MOB | 31 large, 31 small | 0/20 | 0/20 |
| pPtPuc3/TpA-MOB | 500 | 16/18 | 16/20 |
| pPtPuc4/TpA-MOB | 85 | 0/20 | 0/20 |

Figure 4A:
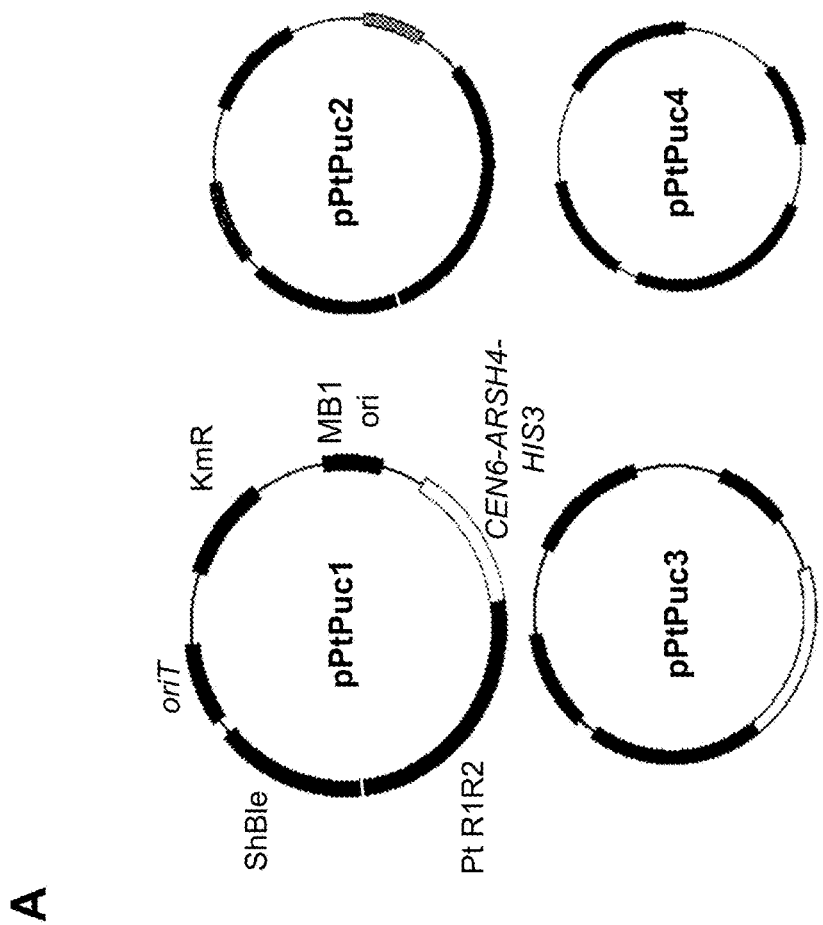
FIGS. 4A-B Average number of *P. tricornutum* colonies obtained per conjugation for different "cargo" plasmid variants of p0521s. A) Maps of plasmids used to test the *P. tricornutum*- and yeast-derived regions: pPtPuc1 includes the yeast maintenance region (CEN6-ARSH4-HIS3, SEQ ID NO:5) as well as the *P. tricornutum*-derived region of the chromosome 25 scaffold present in p0521s; pPtPuc2 includes the *P. tricornutum*-derived region of the chromosome 25 scaffold of p0521s but does not include the yeast maintenance region (SEQ ID NO:5); pPtPuc3 includes the yeast maintenance region (SEQ ID NO:5) but does not include the *P. tricornutum*-derived region of the chromosome 25 scaffold; and pPtPuc4 did not contain either of the yeast maintenance region (SEQ ID NO:5) or the *P. tricornutum*-derived region of the chromosome 25 scaffold. All four plasmids included the bacterial maintenance region from pUC19 along with the oriT (SEQ ID NO:12) for conjugal transfer of the cargo plasmid and ShBle cassette (SEQ ID NO:8) for phleomycin resistance in *P. tricornutum*. B) provides the average number of *P. tricornutum* colonies obtained per conjugation with the different cargo plasmid variants of p0521s depicted in A). The cargo plasmids listed in the table are aligned with the X axis of the graph.

To identify the non-diatom sequence responsible for replication in P. tricornutum three possible regions of the p0521s plasmid were varied: the bacterial maintenance region, the yeast maintenance region (CEN6-ARSH4-HIS3), and the P. tricornutum-derived region. The influence of the bacterial maintenance region from p0521s (i.e. pCC1-BAC) was tested by replacing it with the pUC19 origin of replication. The four test plasmids pPtPuc1 through pPtPuc4 (FIG. 4A, Table 1) used this bacterial replication origin together with the P. tricornutum ShBle cassette (SEQ ID NO:8) and oriT sequence (SEQ ID NO:12). The yeast maintenance region (CEN6-ARSH4-HIS3, SEQ ID NO:5) was cloned in plasmids pPtPuc1 and pPtPuc3 only, and the P. tricornutum-derived region was cloned in plasmids pPtPuc1 and pPtPuc2 only. The final plasmid, pPtPuc4, contained only the bacterial maintenance region from pUC19 along with the oriT (SEQ ID NO:12) and ShBle cassette (SEQ ID NO:8) for phleomycin resistance in P. tricornutum.

Figure 4B:
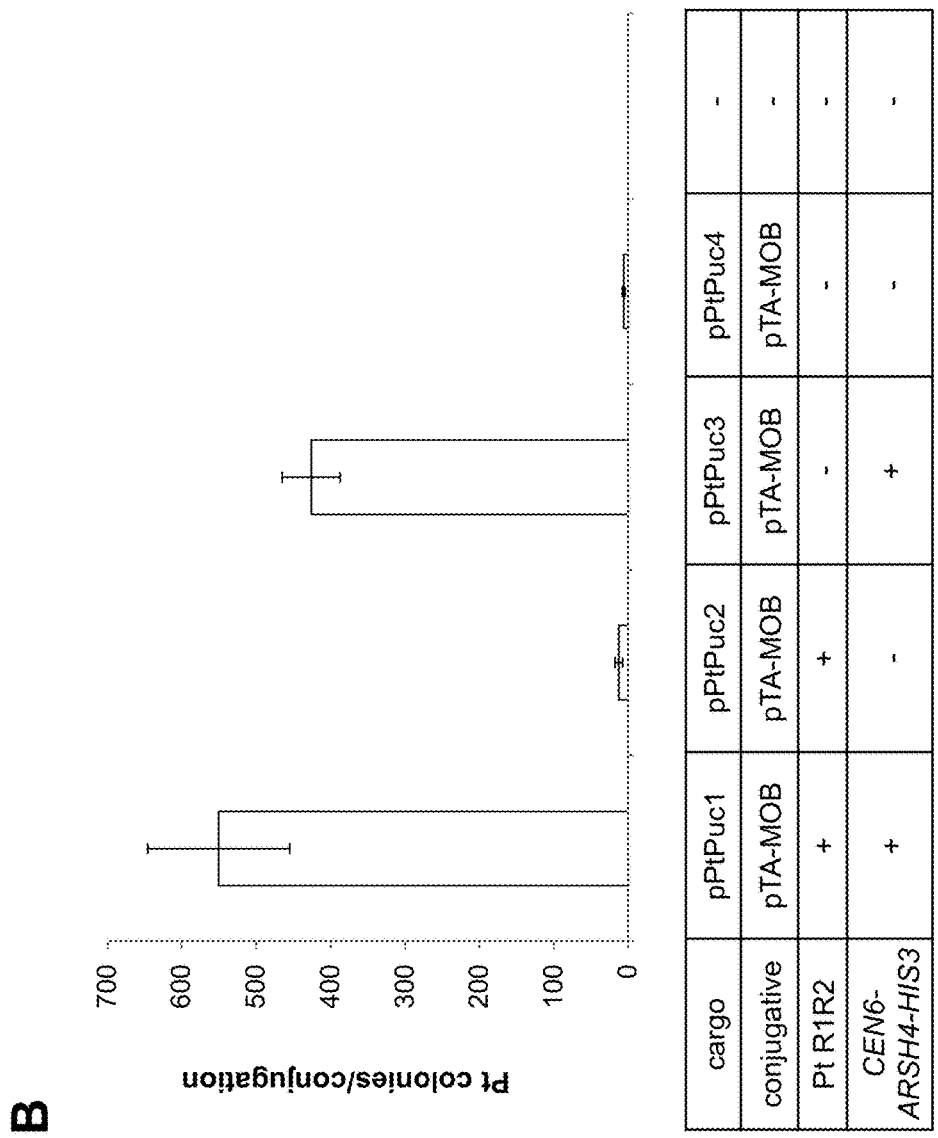

P. tricornutum exconjugants were obtained for all four pPtPuc plasmids; however, pPtPuc1 and pPtPuc3, both containing the yeast maintenance region CEN6-ARSH4-HIS3 (SEQ ID NO:5), yielded over 30-fold more colonies than pPtPuc2 and pPtPuc4 that did not include this region (FIG. 4B and Table 1). Episome rescue was successful for 20/20 and 19/20 P. tricornutum pPtPuc1 and pPtPuc3 colonies, respectively (Table 1). No episomes could be rescued from P. tricornutum pPtPuc2 and pPtPuc4 exconjugants that lacked the yeast maintenance region (SEQ ID NO:5); bleomycin resistant colonies obtained with these plasmids were likely the result of chromosomal integration (Table 1). This result was consistent with the 1.4-kb CEN6-ARSH4-HIS3 fragment (SEQ ID NO:5, present on plasmids pPtPuc1 and pPtPuc3) containing a sequence establishing episomal replication in P. tricornutum.

When rescued, episomes from pPtPuc1 and pPtPuc3 isolated from E. coli were analyzed by gel electrophoresis: 8/20 and 10/20, respectively, had sizes identical to the cargo construct of the bacterial conjugation partner P. tricornutum (Table 1). Thus, the originally isolated P. tricornutum sequence found in p0521s (i.e. R1 and R2) was not essential for episomal replication in *P. tricornutum*, and the vector-derived sequence, CEN6-ARSH4-HIS3 (SEQ ID NO:5), was sufficient to establish replicating episomes. The presence of this cassette resulted in increased numbers of colonies after conjugation (pPtPuc1 and pPtPuc3, FIGS. 4A and 4B), and the colonies that were obtained maintained the plasmid as an extra-chromosomal element (Table 1). In the absence of the cassette (pPtPuc2 and pPtPuc4, FIGS. 4A and 4B), the few colonies that were obtained from conjugation contained the plasmid randomly integrated into the native diatom chromosomes (Table1).

A fifth plasmid, pPtPuc7, was constructed containing the ShBle coding region (SEQ ID NO:10) operably linked to the *Cylindrotheca fusiformis* fcp promoter and terminator (Poulsen & Kroger (2005) *FEBS J.* 272:3413-3423) and the CEN6-ARSH4-HIS3 fragment (SEQ ID NO:5). Thus, this plasmid contained no *P. tricornutum* sequence. In conjugation experiments, the pPtPuc7 DNA transfer construct gave high numbers of transformants, comparable to the p0521s, pPtPuc1, and pPtPuc3 constructs (Table 1) that were able to be recovered as episomes. Because we found that high transformation frequencies resulting from conjugation correlated with replication of the DNA transfer construct as an episome post-conjugation, we consider that pPtPuc7, lacking any *P. tricornutum* sequences (including gene regulatory sequence, e.g., the promoter and terminator regulating expression of the ShBle selectable marker), was able to replicate and be maintained in *P. tricornutum* after being introduced by conjugation, and further that a promoter from a different diatom species (*Cylindrotheca fusiformis*) functions in *P. tricornutum*, allowing selection of transformants.

Figures 5A, 5B, 5C, 5D, 5E:
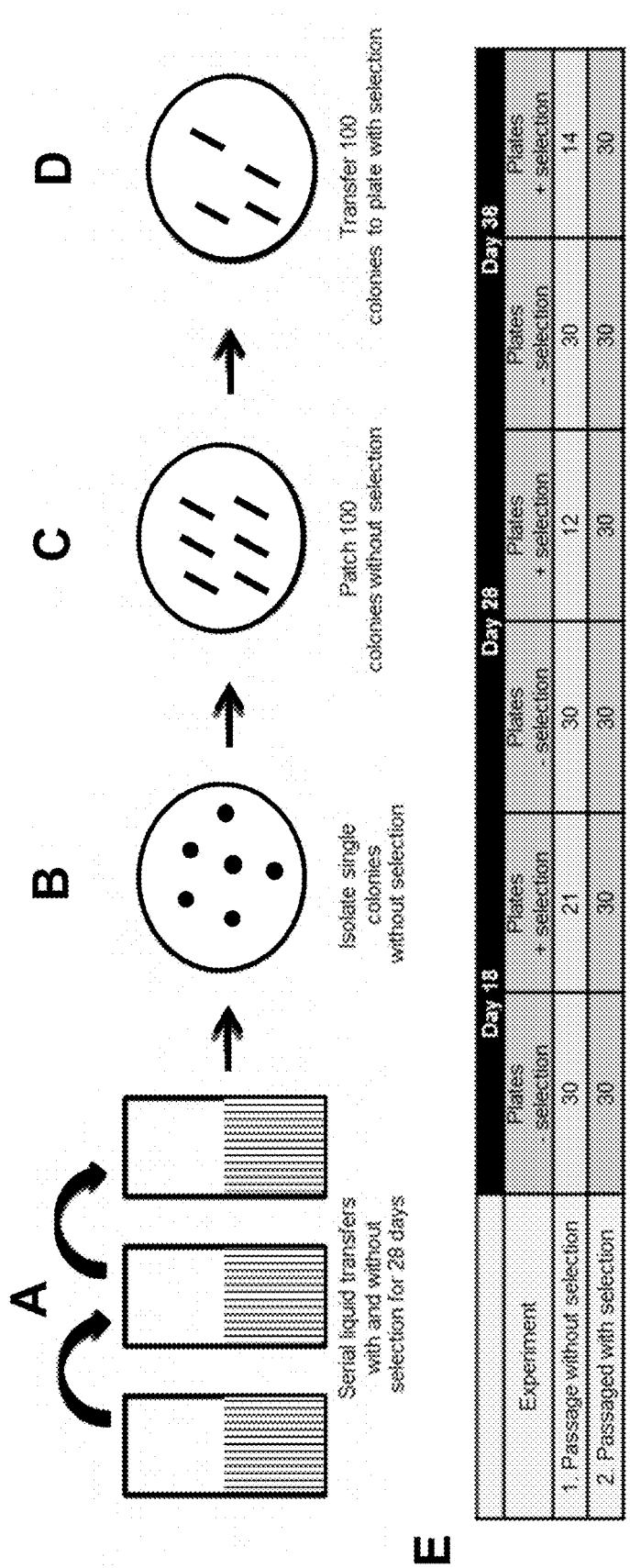

Once the episomes were established in the diatom cell, they were maintained with high fidelity. FIG. 5A-D shows the general scheme for testing stability of constructs transferred to the diatom host by conjugation. FIG. 5E shows that in the absence of selection after an estimated 30 generations (28 days of culturing), an average of 35% of the cells retained the p0521s plasmid corresponding to a segregation efficiency of 97% (Table 2). FIG. 5F-G demonstrate by gel electrophoresis that rescued plasmids from cultures grown for 18 and 38 days, respectively, with or without antibiotic, maintained their original size.

TABLE 2

Maintenance of p0521s Without Selection

| Experiment | # *P. tricornutum* colonies surviving on plates (out of 100) | |
|---|---|---|
| | Without antibiotic selection | With antibiotic selection |
| *P. tricornutum* exconjugant line #3 passaged for 28 days with antibiotic selection | 100 | 93 |
| *P. tricornutum* exconjugant line #3 passaged for 28 days without antibiotic selection | 100 | 27 |
| *P. tricornutum* exconjugant line #9 passaged for 28 days with antibiotic selection | 100 | 90 |
| *P. tricornutum* exconjugant line #9 passaged for 28 days without antibiotic selection | 100 | 42 |

Figures 6A, 6B, 6C:
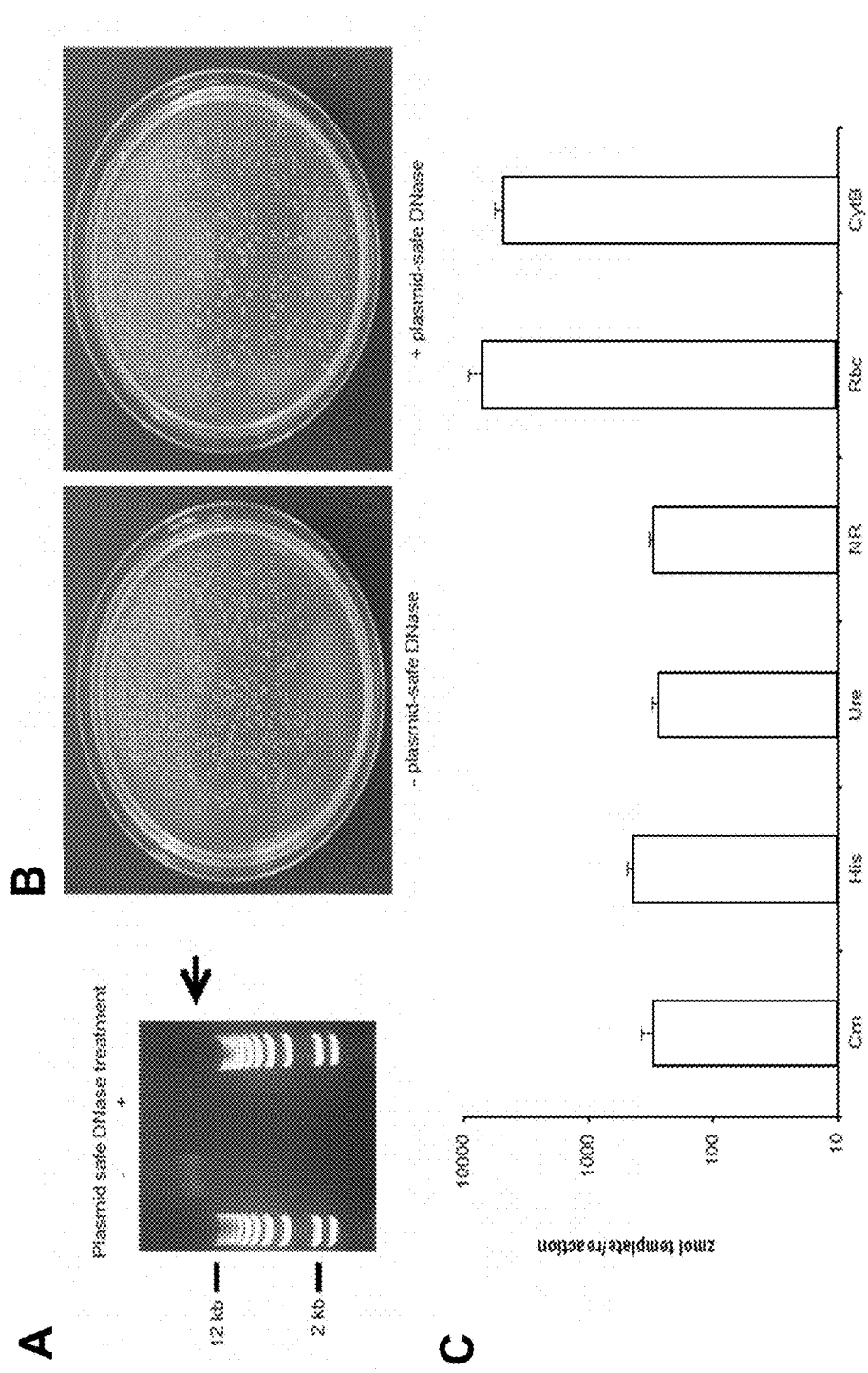
FIGS. 6A-C show that plasmid p0521 replicates as a circle in *P. tricornutum* and with copy number equivalent to native chromosomes. A) DNA isolated from *P. tricornutum* lines containing p0521 untreated (−) or treated (+) with Plasmid-safe exonuclease (Epicentre) separated by agarose gel electrophoresis. Arrow indicates *P. tricornutum* genomic DNA that was degraded by the exonuclease treatment (+) but still present in control treatment (−). B) Plates showing transformed colonies resulting from introduction of the treated or control DNA from part A into *E. coli*. C) Results of qPCR with DNA isolated from *P. tricornutum* lines containing p0521.
Figures 7A, 7B:
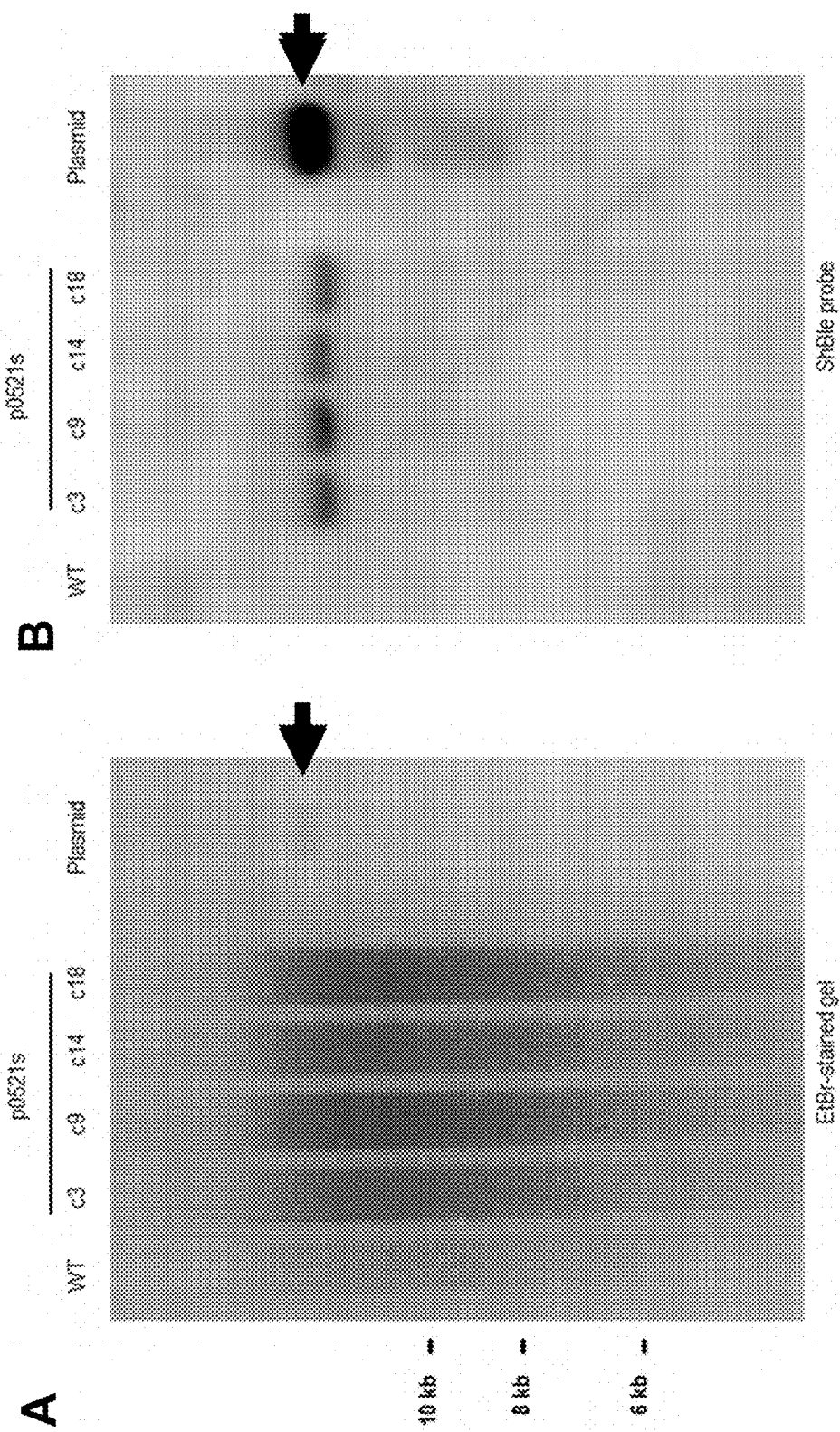
FIGS. 7A-B is an ethidium bromide stained gel and Southern blot of *P. tricornutum* genomic DNA was extracted from wild type (WT) or p0521s ex-conjugate lines (c3, c9, c14, and c18, see FIGS. 3A and 3B) and digested with ClaI. A. DNA (30 µg) was separated by agarose gel electrophoresis. B. Gels were blotted and hybridized with a probe to the ShBle gene. The single band is consistent with lack of integration of the construct into the chromosome.

Episomes p0521s and p0521 were maintained in *P. tricornutum* in closed circular form as determined by exonuclease treatment on extracted *P. tricornutum* DNA before episome rescue. FIG. 6A shows a gel of DNA isolated from *P. tricornutum* exconjugants transformed with the p0521 plasmid treated with an exonuclease ("plasmid safe DNase") that does not digest circular DNA. Equal numbers of bacterial transformants were obtained from treated and untreated rescued p0521 (FIG. 6B). The copy number of the p0521 plasmid in *P. tricornutum* exconjugants as determined by qPCR was equivalent to the chromosomal copy number (where Cm and HIS are found on the p0521 episome backbone, UR (urease) and NR (nitrate reductase) are on host chromosomes 18 and 20, and Rbc and CytB are found in the host plastid and mitochondrial genomes, respectively.) Southern blot analysis in which DNA was extracted from *P. tricornutum* p0521-containing lines also supported circular replication and absence of genomic integration (FIG. 7B).

Figures 8A, 8B:
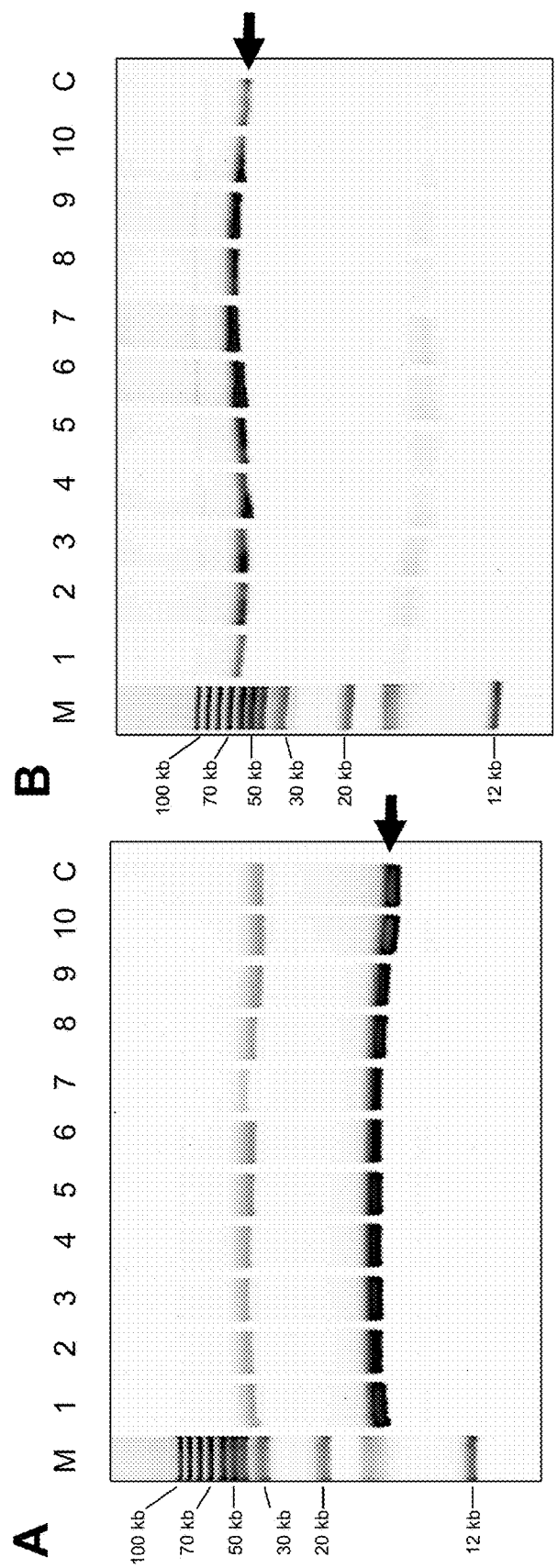
FIGS. 8A-E show that *P. tricornutum* episomes introduced by conjugation replicate as stable, circular, low copy plasmids. A) Agarose gel of rescued p0521 s plasmids derived from separate *P. tricornutum* colonies that were initially sub-cultured for 28 days without (lanes 1-5) or with (lanes 6-10) antibiotic selection. "M" designates supercoiled marker and "C" designates the original plasmid (isolated from clone 9) introduced into *P. tricornutum*. Arrow denotes supercoiled plasmid band. B) Agarose gel of rescued cargo plasmid p0521-Se containing a 49-kb *S. elongatus* fragment. Arrow denotes supercoiled plasmid band. C) Graph showing number of *E. coli* transformants using plasmids extracted from *P. tricornutum* which were untreated, treated with exonuclease, ClaI endonuclease, or treated with a combination of exonuclease and ClaI. D) Agarose gel electrophoresis of plasmids extracted from *P. tricornutum* and treated with nucleases. Lanes from left to right: 1) 1 kb+ ladder, 2) p0521s control, 3) p0521s exonuclease-treated, 4) p0521s untreated, 5) 1 kb+ ladder. E) Copy number of p0521s in *P. tricornutum* determined by qPCR. Cm and His are loci found on the episome backbone; Ure and NR are loci encoded on *P. tricornutum* nuclear chromosomes 18 and 20, respectively; Rbc and CytB are loci found on the *P. tricornutum* chloroplast and mitochondrial chromosomes, respectively.
Figures 8C, 8D, 8E:
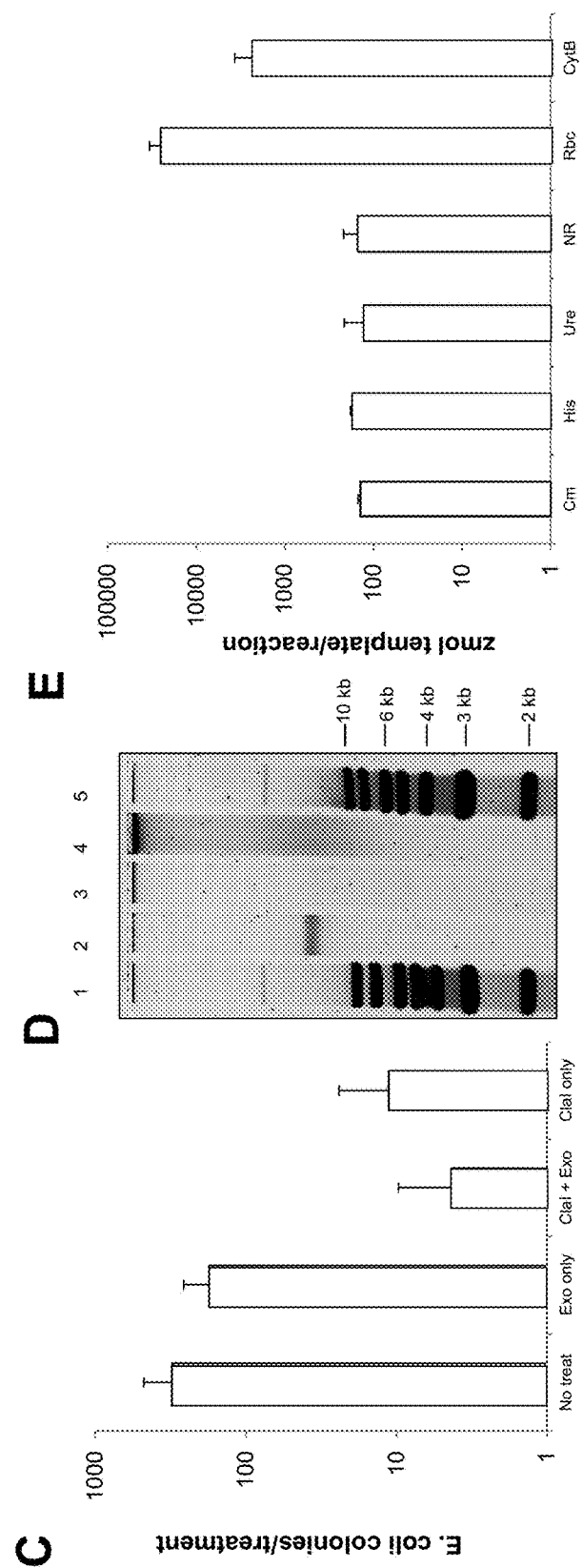
Figures 9A, 9B, 9C, 9D:
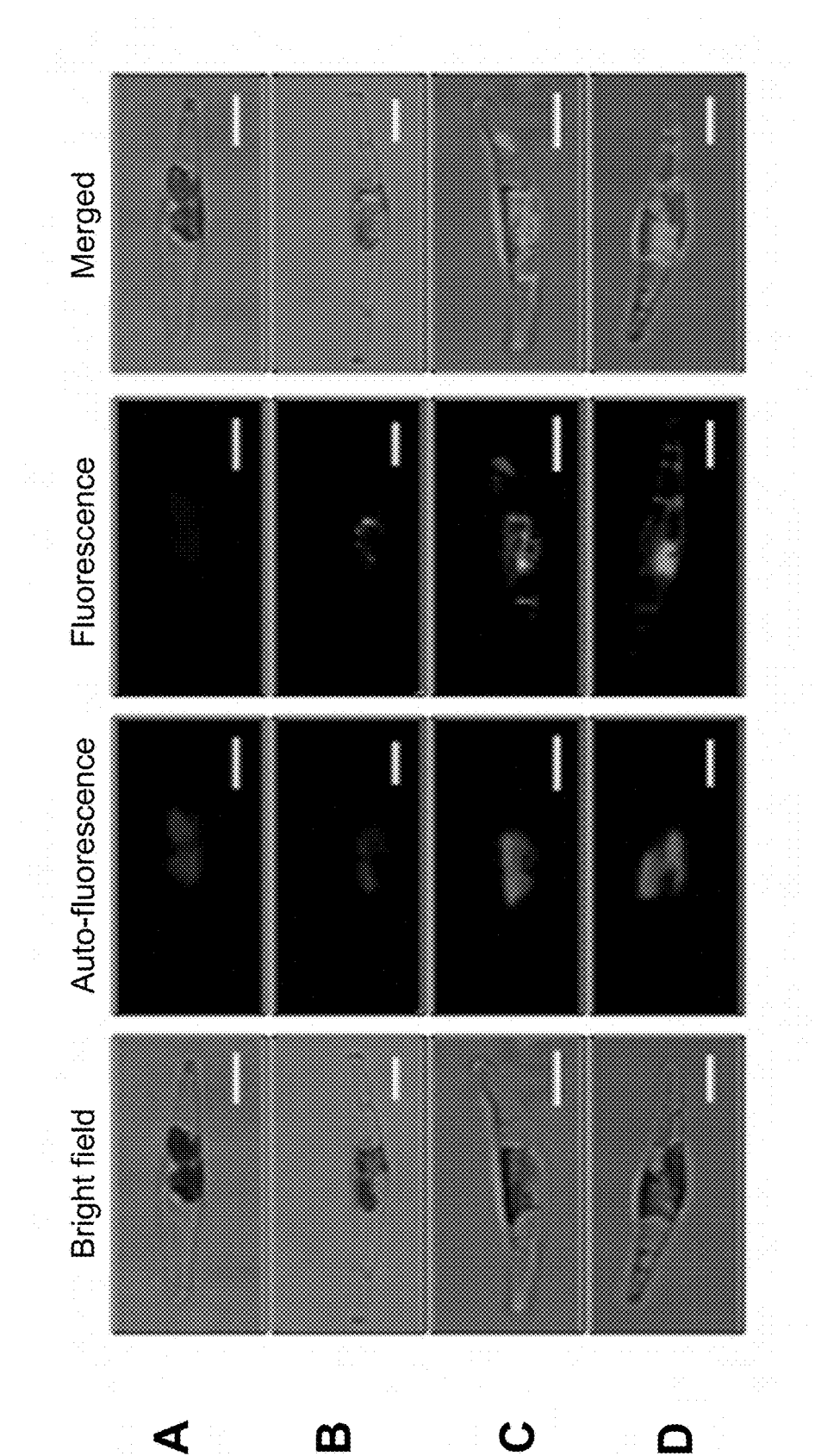
FIGS. 9A-D show laser scanning confocal microscopy of *P. tricornutum* ex-conjugants containing variants of p0521s with fluorescently-tagged proteins. A) Wild type *P. tricornutum*, fluorescence measured with GFP settings. B) *P. tricornutum* expressing GFP localized to the cytoplasm. C) *P. tricornutum* expressing YFP translationally fused to mitochondrial urea transporter (Protein ID 39772). D) *P. tricornutum* expressing CFP translationally fused to beta-carbonic anhydrase (Protein ID 51305) localized to the chloroplast pyrenoid. Scale bar indicates 5 µm.

After 28 days of culturing *P. tricornutum* exconjugants transformed with the p0521s cargo plasmid with and without antibiotics, isolated and rescued plasmids showed no size changes (FIG. 8A). This was also true of a cargo plasmid having a large amount of foreign DNA: A 49-kb heterologous sequence corresponding to the sequence extending from chromosome coordinate 223,718 to 272,317 of the cyanobacterium *Synechococcus elongatus* (*S. elongatus* PCC7942 genome sequence Genbank Accesssion NC_007604.1, GI:81298811) was also maintained on the p0521s episome at the correct size for two months in the presence of antibiotic (p0521-Se, FIG. 8B). The *S. elongatus* chromosomal sequence was TAR cloned from a BAC construct (Noskov et al. (2012) *ACS Synth Biol.* 1:267-273) after digesting the BAC construct with the restriction enzyme FseI. Three regions of the *S. elongatus* insert in the final construct were checked by multiplex PCR and plasmids were analyzed by agarose gel electrophoresis to confirm that they had the correct size. Rescued plasmids after extended culture were also found to be resistant to the "plasmid safe" exonuclease (FIGS. 8C and 8D), consistent with autonomous replication, and present in copy number equivalent to chromosomes (FIG. 8E).

The biotechnological utility of the diatom episome was tested by expressing multiple fusions of fluorescent proteins with proteins of known localization (FIG. 9A-D). To make the fluorescent protein translational fusion expression vectors, expression cassettes consisting of a promoter, a fluorescent protein by itself or fused in frame to a protein of known localization, and a terminator, were first assembled in pUC19 vectors. For pXFP11, the *P. tricornutum* nitrate reductase promoter (Uniprot Protein ID 54983) was amplified from *P. tricornutum* genomic DNA using primers NewXFP1 (SEQ ID NO:14) and NewXFP12 (SEQ ID NO:15), the GFP gene was amplified using primers NewXFP13 (SEQ ID NO:16) and NewXFP14 (SEQ ID NO:17), and a nitrate reductase terminator sequence was amplified from *P. tricornutum* genomic DNA using primers NewXFP15 (SEQ ID NO:18) and NewXFP16 (SEQ ID NO:19). These three PCR products were purified using the QIAquick PCR purification kit (Qiagen) and assembled into an EcoRI- and HindIII-digested pUC19 plasmid using Gibson Assembly. The cassette was then reamplified with primers YeastXFPF4 (SEQ ID NO:20) and YeastXFPR2 (SEQ ID NO:21) and assembled into p0521s using yeast assembly.

To make a mitochondrion-localized fluorescent protein fusion expression cassette, the mitochondrial urea transporter gene (XP_002183652.1, GI:219126831) was amplified from *P. tricornutum* genomic DNA using primers NewXFP11 (SEQ ID NO:22) and HA-MTUT-YFP-Term-4 (SEQ ID NO:23), omitting the stop codon. YFP was amplified using primers Fcp-MtUT-YFP-Term-5 (SEQ ID NO:24)

and HA-MtUT-YFP-Term-6 (SEQ ID NO:25). Regulation for this cassette was provided by the FcpB promoter amplified from *P. tricornutum* using primers NewXFP9 (SEQ ID NO:26) and NewXFP10 (SEQ ID NO:27) and the FcpA terminator using primers HA-MtUT-YFP-Term-7 (SEQ ID NO:28) and HA-MTUT-YFP-Term-8 (SEQ ID NO:29). These four PCR products were purified using the QIAquick PCR purification kit (Qiagen) and assembled into an EcoRI- and HindIII-digested pUC19 plasmid using Gibson Assembly (Gibson et al. (2009) *Nature Methods* 6:343-345 and U.S. Pat. No. 8,968,999, both incorporated by reference in their entireties. The cassette was then amplified using primers YeastXFPF5 (SEQ ID NO:30) and YeastXFPR1 (SEQ ID NO:31) and assembled into p0521s using yeast assembly.

To make pXFP3, the cassette consisting of FcpB promoter, the beta-carboxyanhydrase open reading frame (*Phaeodactylum tricornutum* protein ID 51305) translationally fused to cyan fluorescent protein (CFP), and the FcpA terminator was amplified from a previously constructed plasmid (Hopkinson et al. (2011) *Proc. Natl. Acad. Sci. USA* 108:3830-3837) using primers YeastXFPF2 (SEQ ID NO:32) and YeastXFPR1 (SEQ ID NO:33) and assembled into p0521s using yeast assembly.

FIGS. 9A-D demonstrate by confocal microscopy that genes encoded on the cargo plasmid were expressed in all cases. Altogether, the data presented is consistent with p0521s maintained as a stable, circular, episome replicating at a similar copy number as native nuclear *P. tricornutum* chromosomes and allowing efficient protein expression.

Example 3. Genetic Manipulation of *Thalassiosira pseudonana*

Figure 10:
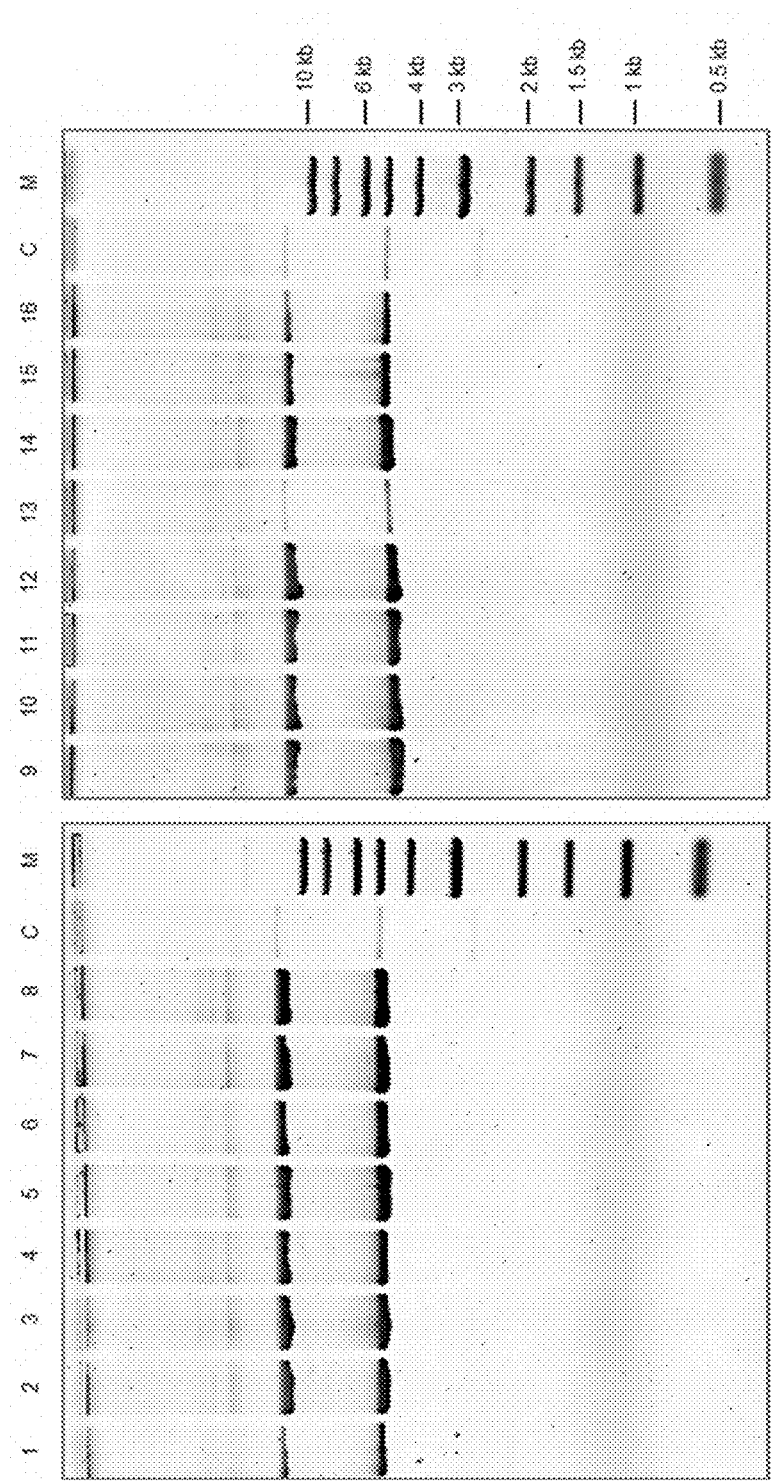
FIG. 10 is a gel showing plasmid pTpPuc3 rescued from *T. pseudonana* exconjugant lines. DNA from 16 *T. pseudonana* exconjugant lines was extracted and transformed to *E. coli* for subsequent isolation and separation by agarose gel electrophoresis. Lanes marked with "M" indicate 1-kb ladder (NEB) and with "C" indicate pTpPuc3 plasmid control.

It was further investigated to determine if this system for genetic manipulation of *P. tricornutum* could be transposed to the centric diatom *Thalassiosira pseudonana* that has a fully silicified shell. Episomes were modified to include the nourseothricin antibiotic selectable marker cassette that functions in *T. pseudonana* (SEQ ID NO:34). Using a variant of plasmid pPtPuc3 (Genbank Accession KP745601.1, GI:825091366) that was called pTpPuc3 (Genbank Accession KP745603.1, GI:825091403), the episome was successfully conjugated into *T. pseudonana* with an efficiency of $2.0 \times 10^4$ diatom cells. While plasmids with the CEN6-ARSH4-HIS3 (SEQ ID NO:5) region (pTpPuc3) or without the CEN6-ARSH4-HIS3 region (pTpPuc4) both yielded *T. pseudonana* colonies (FIG. 11A), only the pTp-Puc3 episome could be successfully rescued. This was consistent with the results in *P. tricornutum* in which the yeast sequence conferred episomal replication ability. Plasmids recovered after episome rescue from *T. pseudonana* were identical in size to the original plasmid control (FIG. 10 and Table 1).

A version of p0521s was constructed that had the nourseothricin resistance gene driven by a *T. pseudonana* promoter and that also encoded a translational fusion between YFP and *T. pseudonana* phosphoenolpyruvate carboxykinase (PEPCK). The phosphoenolpyruvate carboxykinase (PEPCK) from *T. pseudonana* (protein ID 5186) was cloned from cDNA using the primers Tp-PEPCK-F (SEQ ID NO:35) and Tp-PEPCK-R (SEQ ID NO:36), replacing the stop codon with TTA-leucine. The PCR product was then introduced into pENTR/D/Topo (Invitrogen) and sequenced. PEPCK was then transferred into a custom-built Gateway-compatible destination vector for YFP fusion in C-terminal (pTpDEST-C'YFP) by LR recombination according to manufacturer's instructions (Invitrogen). The plasmid, pTp-ExpPEPCK-YFP, contained the *T. pseudonana*-specific nourseothricin resistance marker flanked by the LHCF9 promoter (983-nt upstream of the *T. pseudonana* protein ID 268127) and the LHCF9 terminator (503-nt downstream of the *T. pseudonana* protein ID 268127) amplified from pTp-fcp/nat5 followed by the expression cassette composed of the PEPCK-YFP fusion flanked by the LHCF9 promoter and terminator. The junction between PEPCK and YFP was checked by sequencing to ensure in frame cloning. Finally, the 6,377-bp region containing the resistance cassette and the expression cassette was re-amplified using the primers Tpconj-F1 (SEQ ID NO:37) and Tpconj-R1 (SEQ ID NO:38) and assembled into the p0521S-URA by yeast recombination as described above to give the final vector p0521-Tp-PEPCK-YFP.

*T. pseudonana* cells were prepared for conjugation by centrifuging 500 mL of liquid grown culture for 5 min at 4000×g at 10° C., removing most of the media, and counting suspended cells using a hemocytometer to adjust the cell concentration to $2 \times 10^8$ cells/mL. *E. coli* cells (150 mL) grown at 37° C. to OD600 of 0.3 were spun down for 10 min at 3000×g and resuspended in 800 μL of SOC media.

For conjugation, 200 μL of *T. pseudonana* cells was moved to 1.5 mL microfuge tube and then 200 μL of *E. coli* cells were added and mixed by pipetting up and down a few times. Next cells were plated on ½× *T. pseudonana* medium, 5% LB, 1% agar plates and incubated for 90 minutes at 30° C. in the dark, then moved to 18° C. in the light and grown for 4 hr. Then 1 mL of *T. pseudonana* medium was added to the plate and cells were scraped. 200 μL of the scraped cells was plated on ½× *T. pseudonana* medium, Nourseothricin 50 μg/ml, 1% agar plate and incubated at 18° C. in the light. Colonies appeared after 7-14 days.

Figures 11A, 11B, 11C:
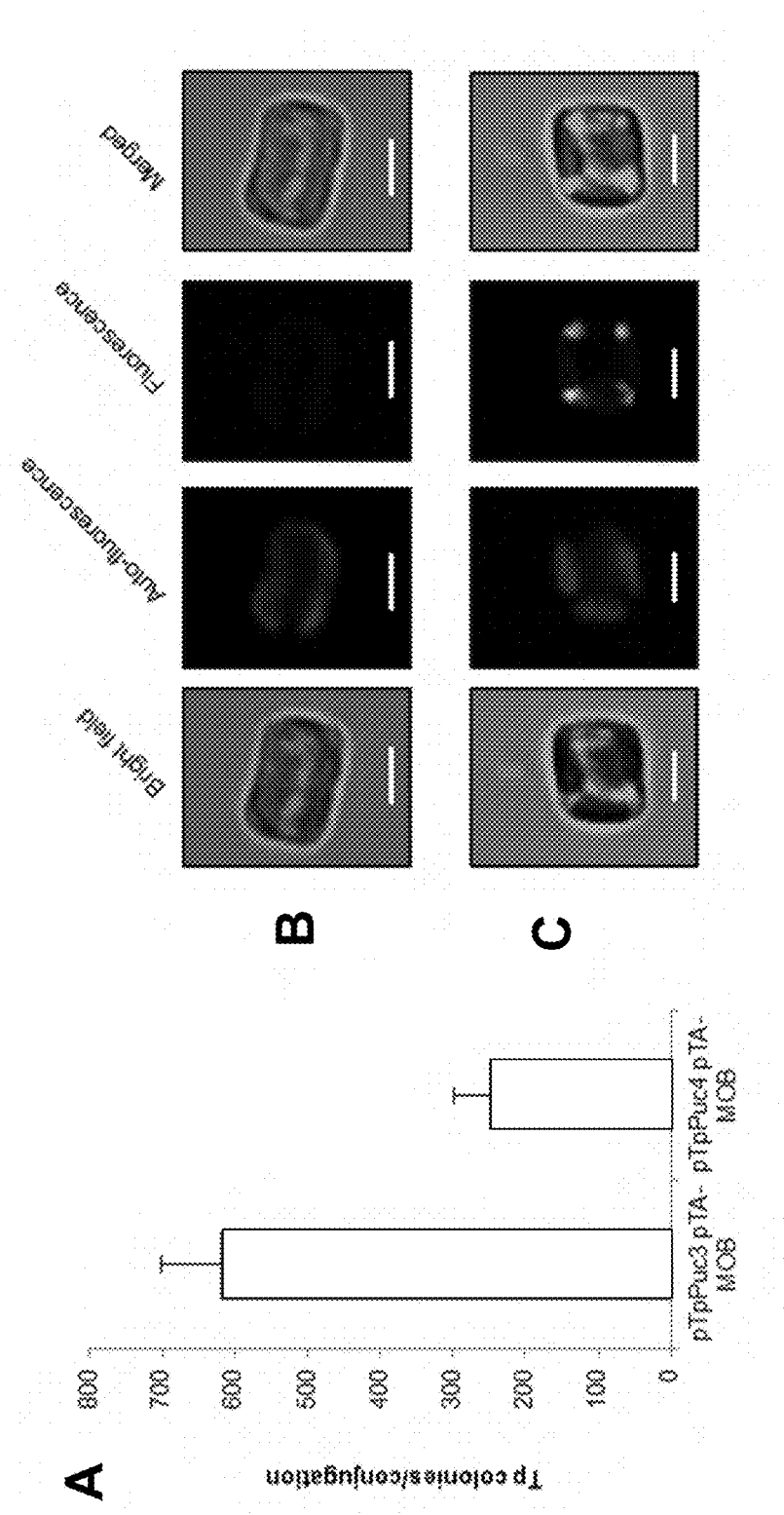
FIGS. 11A-C show episome replication in *T. pseudonana*. A) Conjugation efficacy of transfer from *E. coli* to *T. pseudonana* with and without yeast CEN6-ARSH4-HIS3 region. B) Images of *T. pseudonana* wild type (not transformed) cells and C) *T. pseudonana* ex-conjugants expressing YFP translationally fused to PEPCK encoded on a p0521s-derived episome. Scale bar indicates 2.5 µm.

Introduction of this plasmid resulted in *T. pseudonana* exconjugants with highly visible YFP signal in the mitochondria as expected (FIG. 11C). Altogether the results observed for *T. pseudonana* mirror the findings in *P. tricornutum* and established that the episome/conjugation system operates in a similar fashion in both diatom species.

Discussion

A small sequence (1.4-kb) from yeast that permits low copy episomal replication in the diatoms *P. tricornutum* and *T. pseudonana* was discovered. This small yeast sequence (CEN6-ARSH4-HIS3; SEQID NO:5) contains the plasmid maintenance functions for yeast centromeric plasmids (CEN6 and ARSH4) and the HIS3 gene to complement yeast histidine auxotrophy. Two replicating plasmids for *P. tricornutum*, p0521s (GenBank Accession KP745602.1, GI:825091387) and pPtPuc3 (GenBank Accession KP745601) were constructed, and each contains the CEN6-ARSH4-HIS3 sequence. A plasmid identical to pPtPuc3, but with the antibiotic selection replaced with the *T. pseudonana* nourseothricin resistance cassette, was also constructed (pT-pPuc3, GenBank accession KP745603). Plasmid p0521s has an ShBle cassette for *P. tricornutum* selection with phleomycin as well as the pCC1BAC backbone to support large inserts (up to several hundred kilobases) in *E. coli*. Cloning sequences of interest into this backbone can be performed using yeast assembly methods and inserts can be designed to replace the URA3 gene with counter selection on 5-fluororitic acid (5FOA). When cloning genes of interest into p0521s using yeast assembly, pre-digestion of the plasmid with I-CeuI is recommended to linearize the plasmid at one of the URA3 junctions to increase recombination efficiency. For expression of smaller sequences in *P. tricornutum* (e.g. single gene expression cassettes), pPtPuc3 is better suited with a smaller backbone that can be amplified by PCR and assembled with sequences of interest using Gibson assembly. Note that the high copy number of pUC19-based plasmids may complicate cloning sequences larger than 10-kb. To clone sequences into pPtPuc3, the sequences of interest were typically inserted immediately following the 3' end of the CEN6-ARSH4-HIS3 region. Plasmid pTpPuc3 can be engineered with genes in a similar manner as described above for pPtPuc3. Alternatively, the CEN6-ARSH4-HIS3 region can simply be amplified and added to any plasmid to permit replication as an episome, provided a means of selection for transformed cells is also present on the plasmid. Further inclusion of a sequence that allows mobilization of the cargo plasmid such as an oriT sequence (e.g., SEQ ID NO:12) is necessary for introduction by conjugation.

While the initial approach was to discover diatom DNA sequences that function as centromeres, the resulting finding that a yeast-derived sequence could function in a similar manner was surprising and could help elucidate native diatom centromere sequences and sequence requirements in ongoing research. Whether the yeast-derived sequence functions as a true centromere in diatoms remains to be tested. Although maintenance of the P. tricornutum episome without antibiotic selection was not as high as the ~80-95% retention observed for yeast centromeric vectors, it is higher than yeast vectors based on replication origins (ARSs) in which only 1% of cells maintain the plasmid in the absence of selection after an equivalent number of generations. Furthermore, as noted for yeast, most of the rearrangements of the diatom episome appear to occur during plasmid introduction; once a line was verified to have the correctly sized plasmid in P. tricornutum, the episome replicated without significant alteration over long periods of time (FIG. 5A-G, FIG. 8A-E). Interestingly, the CEN6 (13% GC) and ARSH4 (30% GC) regions have much lower GC content relative to the average for P. tricornutum (48% GC). Low GC regions are known key features in red algal and other protist centromeres and may be functioning in a similar manner in P. tricornutum.

The diatom system described above is the second system (apart from yeasts) in which an episome was introduced into a eukaryotic cell by conjugation and stably maintained. Conjugative delivery of such elements results in order of magnitude gains in efficiency over widely used particle bombardment methods, both in time and materials, at the genetic manipulation and screening stages. Additionally, large DNA sequence (49-kb) were successfully introduced and maintained in P. tricornutum using this system, suggesting that an entire metabolic pathway could be introduced into the diatom, which may facilitate and accelerate biotechnological applications in these organisms. Great flexibility in the conditions that favor conjugation (FIG. 1) was observed, but presented the optimum protocols that were developed. For P. tricornutum, it was found that diatom cells grown on agar plates were transformed by conjugation at a higher rate than liquid grown cells, while T. pseudonana cells were best grown in liquid culture due to difficulties growing this diatom on plates for extended periods. In adapting the technique to other diatom species, plasmids should minimally have the CEN6-ARSH4-HIS3 region, an origin of transfer (oriT), and a selectable marker functioning in the diatom of interest. Conditions during the conjugation (60-90 min at 30° C. on ½ strength L1 agar+5% LB medium) are a compromise between those optimal for E. coli (LB agar, 37° C.) and those optimal for the diatom (L1 medium, 18° C.) and will likely require empirical determination for other diatom species.

In addition to its biotechnological utility, bacterial conjugation to diatoms is interesting in light of the complex evolutionary history of the Stramenopile clade that is characterized by multiple endosymbiotic events and recent horizontal gene transfers from marine bacteria. Diatom genomes contain a high percentage of recently transferred bacterial genes, and trans-kingdom conjugation may provide a possible mechanism to explain the acquisition of some of the bacterial DNA that makes up 5-10% of diatom genomes. The results also add credence to the increasing awareness that conjugation influences microbial ecology in the oceans.

The ease, simplicity and scalable nature of these novel tools makes them amenable to an efficient and high throughput functional genetic system for diatoms. This system represents a new and exciting development to begin to make rapid and fundamental advances in gene function and to start understanding the molecular regulation controlling the biology of these globally significant marine phytoplankton species.

Example 5. General Methods

Strains, media, growth conditions: *Saccharomyces cerevisiae* VL6-48 (ATCC MYA-3666: MATα his3-Δ200 trp1-Δ1 ura3-52 lys2 ade2-1 met14 cir0) cells were grown in rich medium (YEPD) or complete minimal (CM) medium lacking histidine or histidine and uracil or histidine to which 1 g/L of 5-fluoroorotic acid (5FOA) was added (Teknova). In addition of 60 mg/L adenine sulfate was added to all yeast media.

*Escherichia coli* (Epi300, Epicentre) were grown on Luria broth or agar supplemented with chloramphenicol (20 mg/L) or kanamycin (50 mg/L) or ampicillin (50 mg/L) or tetracycline (10 mg/L) or gentamicin (20 mg/L) or combinations of these as needed.

*Phaeodactylum tricornutum* was grown in L1 medium at 18° C. under cool white fluorescent lights (50 µE m-2 s-1). L1 medium. For liquid medium combine: 1 L Aquil Salts (Synthetic Seawater), 2 mL NP stock, 1 mL L1 trace metals stock, 0.5 mL f/2 vitamin solution. Filter sterilize through a 0.2 µm filter. For agar plates, combine 1 part sterilized liquid L1 medium and 1 part autoclaved 2% Bacto agar and pour into petri dishes. Aquil salts: (Two separate solutions, anhydrous and hydrous salts, are made at 2× strength and mixed to make Aquil salts). Anhydrous salts (resuspend in 500 mL): NaCl 24.5 g, $Na_2SO_4$ 4.09 g, KCl 0.7 g, $NaHCO_3$ 0.2 g, KBr 0.1 g, $H_3BO_3$ 0.03 g or 3 ml 10 mg/ml stock, NaF 0.003 g or 300 ul 10 mg/ml stock. Hydrous Salts (resuspend in 500 mL): $MgCl_2$ 6 $H_2O$ 11.1 g, $CaCl_2$ $2H_2O$ 1.54 g. NP stock: $NaNO_3$ 37.5 g per 100 ml, $NaH_2PO_4$—$H_2O$ 2.5 g per 100 ml. L1 trace metals, mix up the following to make 1 L at 1000× (stock solutions in parentheses): $FeCl_3.6H_2O$=3.15 g, $Na_2EDTA.2H_2O$ 4.36 g, $CuSO_4.5H_2O$ (9.8 g/L $dH_2O$) 0.25 ml, $Na_2MoO_4.2H_2O$ (6.3 g/L $dH_2O$) 3.0 ml, $ZnSO_4.7H_2O$ (22.0 g/L $dH_2O$) 1.0 ml, $CoCl_2.6H_2O$ (10.0 g L-1 $dH_2O$) 1.0 ml, $MnCl_2.4H_2O$ (180.0 g L-1 $dH_2O$) 1.0 ml, $H_2SeO_3$ (1.3 g L-1 $dH_2O$) 1.0 ml, $NiSO_4.6H_2O$ (2.7 g L-1 $dH_2O$) 1.0 ml, $Na_3VO_4$ (1.84 g L-1 $dH_2O$) 1.0 ml, $K_2CrO_4$ (1.94 g/L $dH_2O$) 1.0 ml. F/2 vitamin solution: Thiamine-HCl add 200 mg powder/L, Biotin add 10 ml/L of a 0.1 g/L stock, Cyanocobalamin add 1 ml/L of a 1 g/L stock.

*Thalassiosira pseudonana* (Hustedt) Hasle et Heimdal (clone CCMP 1335) from the Provasoli Guillard NCMA (National Center for Marine Algae and microbiota, Maine, USA) were grown between 18-22° C., using 0.2 µm filtered and boiled nutrient-poor seawater (Scripps pier, La Jolla, Calif.: lat-long N 32.86671 and W 117.25587, collected Apr.

4, 2014) with metals and vitamins added to achieve f/2 trace element concentrations (Poulsen & Kroger (2005) Mid). Phosphate was supplied as 25 silicate was provided at 100 μM ($Na_2SiO_3 \cdot 9H_2O$) and nitrogen was supplied as a mixture of 200 μM ammonium chloride ($NH_4Cl$) plus 200 μM sodium nitrate ($NaNO_3$). Cultures were illuminated on a light/dark cycle of 16/8 h with cool-white fluorescent lamps (Vita-Lite 5500K, DUROTEST, USA) at photon flux densities (PFDs) between 80-130 μE m-2/s. *T. pseudonana* cell plating was conducting using ¾ of the sea water media described above, plus ¼ double distilled water and 8 g/L of bactoagar (Sigma).

DNA isolation: Preparation of agarose-embedded DNA was performed as previously described in Karas et al. (2013) Ibid. Plasmid DNA was isolated using the modified alkaline lysis protocol described below. Steps 1-3 are variable depending on the species while steps 4-10 are common for all species.

Step 1-3 for *S. cerevisiae*. 1) 5-10 mL of yeast culture was grown to high density. 2) Next yeast cells were pelleted at 3000×g for 5 min and supernatant was discarded. 3) Cells were resuspended in 250 μL resuspension buffer which contained 240 μL P1 (Qiagen), 5 μL of 1.4 M β-Mercaptoethanol and 5 μL Zymolyase solution (Zymolyase solution: 200 mg Zymolyase 20T (USB), 9 mL $H_2O$, 1 ml 1M Tris pH7.5, 10 mL 50% glycerol, stored at −20° C.) and incubated at 37° C. for 60 min.

Step 1-3 for *P. tricornutum* and *T. pseudonana*. 1. 10-20 mL cultures were harvested during exponential growth phase. 2. Cells were pelleted at 4000×g for 5 min, supernatant was discarded. 3. Cells were resuspended in 250 μL resuspension buffer which contained 235 μL P1 (Qiagen), 5 μL hemicellulose 100 mg/mL, 5 μl of lysozyme 25 mg/L, and 5 μL Zymolyase solution (Zymolyase solution: 200 mg Zymolyase 20T (USB), 9 mL $H_2O$, 1 mL 1M Tris pH7.5, 10 mL 50% glycerol, stored at −20° C.) and then cells were incubated at 37° C. for 30 min.

Step 1-3 for *E. coli*. 1) 2 mL overnight cultures were used to inoculate 25 mL LB median containing appropriate antibiotic and induction solution (Epicenter) and grown for 4-5 hours in 37° C. shaker. 2) Next *E. coli* cells were pelleted at 4,000×g for 5 min, supernatant was discarded. 3) Cells were resuspended in 250 μL.

Steps 4-10 common for all species. 4) 250 μL lysis buffer P2 (Qiagen) was added and samples were inverted 5-10 times to mix. 5) Then 250 μL of Neutralization buffer P3 was added and samples were inverted 5-10 times to mix. 6) Then samples were spun down at 16,000×g, 10 min. 7. Supernatant was transferred to a clean tube and 750 μL isopropanol was added and samples were mixed by inversion and spun down at 16,000×g, 10 min. 8. Next supernatant was removed and 750 μL 70% EtOH was added and samples were mixed by inversion and span down at 16,000×g, 5 min 9. Next supernatant was discarded and pallets were resuspended in 50-100 μL of TE buffer. 10. After that samples were kept at 37° C. for 30-60 min to dissolve.

Transfer of DNA into *P. tricornutum* by electroporation: 200 mL culture in exponential phase (bulk florescence=50) were centrifuged at 3,000×g for 5 min. Supernatant was removed, cells were resuspended in 1 mL of 0.5 M NaCl, 50 mM mannitol and centrifuged at 3,000×g for 5 min. Next supernatant was removed and cells were resuspended in 1 mL of 1M Sorbitol. Next 400 μL of cells were removed and mixed with 10 μL plasmid DNA (~2 μg μL−1). The mixture was moved to a 0.2 cm electroporation cuvette (Bio-Rad) and subjected to electroporation at 700V, 200 Ohm, 25 μF. Then cells were resuspended in 20 mL of L1 media and grow for two days before transfer to selection plates containing phleomycin (20 μg/mL).

Transfer of DNA into *P. tricornutum* by polyethylene glycol transformation method: *P. tricornutum* cells were grown in L1 liquid medium or on plates. Liquid cultures were spun for 5 min at 4,000×g at 10° C. Supernatant was removed and cells were counted using hemocytometer. Next cells were resuspended to give final concentration in the range of 3-6×$10^8$ cells/mL. For *P. tricornutum* grown on plates, 250 μL of *P. tricornutum* culture adjusted to 1.0×$10^8$ cells/mL was plated on ½L1, 1% agar plates and grown for 4 days, then 500 μL of L1 media was added to the plate and plate was scraped to collect the cells. Then cell concentration was adjusted to 3-6×$10^8$ cells/mL. Next 1 mL of cells was resuspended in 9 mL of filter sterilized spheroplasting solution (20 μL of Zymolase 100T (10 mg/mL), 100 μL of freshly made lysozyme (25 mg/mL), 0.1 g of hemicellulase, and L1 solution was added to final volume of 9 mL) and incubated for 30 min at 37° C. Next 40 mL of L1 solution was added, and mixed by inverting, followed by centrifugation for 5 min at 3,000×g, 10° C. Then supernatant was removed and cells were resuspended in 500 μL of L1 media. 250 μL of spheroplasts were transferred to 1.5 mL Eppendorf tube, and 25 μL of DNA (~1 μg/μL) was added and immediately 1 mL of 25% PEG 8000, 10 mM Tris pH 8, 10 mM $CaCl_2$, 2.5 mM $MgCl_2$, pH 8 equilibrated at 37° C. was added and tubes were invert 4-6 times. Then mixture was incubated at room temperature for 10 min. Next the mixture was centrifuged for 7 min at 1500×g. Supernatant was removed and cells were resuspended in 30 mL of L1 and incubated for 45 min without selection at 18° C. Then cells were centrifuged for 5 min at 3000 RPM, 15° C. Then cells were resuspended in 600 μL of L1 and 200 μL was plated on ½×L1, 20 μg/mL chloroamphenicol. After 2 days cells were scraped (in 500 μL of L1 media) and plated on 0.5×L1, 1% agar plates containing 20 μg/mL phleomycin. Colonies appeared after 10-14 days.

Isolation of p0521: Plasmids containing one of each of the five fragments were introduced into *P. tricornutum*. Plasmids containing what was thought to be fragment 5 from scaffold 25 were later found to be a concatenation of fragments 1 and 5 after Ion Torrent Sequencing. Plasmids recovered from *P. tricornutum* contained either fragment 1 (e.g. p0319 or p0521) or a reduction of fragment 5 (e.g. p0524_3 and p0524_4). A plasmid containing fragment 4 was unexpectedly obtained by an unknown mechanism (p0413). After reintroduction into *P. tricornutum*, plasmid p0521 was recovered at its identical size while plasmid p0524_4 was further reduced.

Sequence analysis of plasmids passaged through *P. tricornutum*: Plasmids isolated from *P. tricornutum* colonies transformed with plasmids containing large fragments of scaffold 25 were transformed to *E. coli* and purified from agarose gels by RECO chips (Takara). Sequencing libraries were prepared for each plasmid for the Ion Torrent platform using the Ion Xpress Plus gDNA Fragment Library Kit (Life Technologies). Samples were barcoded, pooled, and sequencing on an Ion Torrent 314 chip. Reads were mapped to the *P. tricornutum* genome using CLC Genomics Workbench and visualized using GenomeView45. Plasmid p0521s was sequenced after purification using the QIAprep kit using appropriate primers.

Calculation of segregation efficiency for p0521s: Segregation efficiency (Seff) was calculated according to the following equation: $Seff=(Pphleo/100)1/n$ In this calculation, Pphleo is the percentage of phleomycin resistant colonies in cultures passaged without selection and n is the number of nuclear division cycles estimated to have occurred during that time. To calculate Seff for p0521s maintenance in *P. tricornutum*, a value of 30 was used for the variable n and the average Pphleo of 35 was used to arrive at a Seff of 0.97.

Quantitative PCR Experiments: To create standard templates to calibrate the qPCR experiments, templates for each qPCR primer set were assembled onto plasmids. Plasmid pNorm1 was created by amplifying template regions for the yeast HIS3 gene, the chloramphenicol resistance gene (CmR) from pCC1BAC, *P. tricornutum* nitrate reductase (NR, Protein ID 54983), and *P. tricornutum* urease gene (Ure, Protein ID 29702), and assembling them into an EcoRI- and HindIII-digested pUC19 vector using Gibson assembly. Plasmid pNorm2 was created by first amplifying template regions for *P. tricornutum* RuBisCO small subunit located on the chloroplast chromosome (RbcS) and for *P. tricornutum* cytochrome B located on the mitochondrion chromosome (CytB). These amplified products were assembled into an EcoRI- and HindIII-digested pUC19 vector using Gibson assembly. Plasmids pNorm1 and pNorm2 were extracted from *E. coli* using Qiagen QIAprep kit and treated with Plasmid-Safe exonuclease (EpiCentre) to remove any residual genomic DNA. Treated plasmids were extracted twice with phenol:chloroform, precipitated, and quantified by Nanodrop (Thermo) to calibrate qPCR standard curves.

Quantitative PCR analysis was performed using 7900HT Fast Real-Time PCR System (Applied Biosystems) using Fast SYBR Green MasterMix (Applied Biosystems). Reactions consisted of master mix diluted to ix, plasmid or *P. tricornutum* genomic extract and 5 µM primers in 20 µL total volume. To perform qPCR experiments, total DNA was extracted from *P. tricornutum* cells containing plasmid p0521s or pPtPuc3 using a modified CTAB protocol (Hildebrand et al. (1991) *J Bacteriol.* 173:5924-5927). Standard curves were performed for each primer pair using serial dilutions of pNorm1 or pNorm2 plasmid, as appropriate. The reactions were cycled under the following conditions: 95° C. for 20 s, 40 cycles of 95° C. for 1 sec followed by 60° C. for 20 sec during which data was collected. Ct values were calculated by the SDS software, plotted as a function of number of template molecules, and fit to a logarithmic trend line. Curves were linear over at least four orders of magnitude. Three biological replicates (plasmids extracted from different *P. tricornutum* strains containing plasmid) were tested, each with 2-4 technical replicates at each dilution. Ct values resulting from experimental samples were used to calculate the number of molecules of template molecule in the qPCR reaction. The experiment was repeated at least twice for both p0521s and pPtPuc3 plasmids.

Plasmid Safe experiments: Plasmids from *P. tricornutum* lines containing the p0521s plasmid were extracted using the modified alkaline lysis extraction protocol described above. A 2×2 factorial experimental design was set up to test the effects of restriction digest and exonuclease treatment on the ability of plasmids extracted from *P. tricornutum* to transform *E. coli*. First, ClaI restriction digest or mock reaction was performed on samples using 1-2 µg total DNA in a 100 µL total reaction with 1× CutSmart buffer and ClaI (NEB) or water in digested or mock-digested samples, respectively. Reactions were incubated for 1 h at 37° C. To each 100 µl digest or mock digest, 10 µL Plasmid-Safe reaction buffer was added and 8 µL ATP solution, and 3 µL Plasmid-safe exonuclease or water (mock) to a final volume of 200 µL. The reactions were incubated at 37° C. for 1 h. Finally, the reactions were incubated at 70° C. for 1 h to inactivate the enzymes. Treated DNA was precipitated, resuspended in water, and transformed into *E. coli* strain Epi300.

Southern blot: For Southern blot analysis of *P. tricornutum* genomic DNA from lines containing the p0521s plasmid, DNA was extracted using a modified CTAB protocol (Hildebrand et al. Ibid) from *P. tricornutum* cultures grown on L1 agar containing phleomycin (20 µg/l). DNA (~30 µg) was digested with ClaI that cuts a single time within the p0521s plasmid and still cuts frequently within the *P. tricornutum* genome. Plasmid control DNA from *E. coli* was digested with RsrII that also cuts a single time within the p0521s sequence but is not affected by Dam methylation. Digested DNA was separated by agarose gel electrophoresis overnight at 0.1 V/cm in a 1% gel. Southern blot and hybridization was performed as previously described (Hildebrand et al. Ibid) using a probe to the ShBle cassette constructed by the DIG PCR Probe Synthesis Kit (Roche) according to the manufacturer's instruction using primers SB2 and 3' ShBle.

Laser Scanning Confocal Microscopy: A Leica TCS SP5 confocal laser scanning microscope equipped with a 100× oil immersion objective was used to visualize the fluorescently tagged proteins. CFP, GFP and YFP were excited with 458, 488 and 514 nm lasers, with emission monitored at 470-520 (CFP), 505-530 nm (GFP) and 525-560 nm (YFP). Autoflourescence of the plastid was monitored at 700-740 nm.

SEM Microscopy. Sample preparation protocol. Cells were spun at RT for 4 min at 2,000×g to produce a loose pellet. 950 µL of media was removed and replaced with 1 mL of fixative. The fixative solution was 2.5% glutaraldehyde, 100 mM sodium cacodylate, 2 mM calcium chloride, and 2% sucrose (fixative was added cold and samples were stored at 4° C.). Cells were immobilized on polyethylenimine or poly-d-lysine coated ITO glass coverslips for 2 minutes and washed in 0.1M cacodylate buffer with 2 mM calcium chloride and 2% sucrose for 5×2 minutes on ice. Cells were post fixed in 2% osmium tetroxide with 2% sucrose in 0.1 M cacodylate for 30 min on ice. Cells were rinsed in double-distilled water and dehydrated in an ethanol series (20%, 50%, 70%, 100%) for 2 min each on ice. Samples were critical point dried (with $CO_2$) and sputter-coated with a thin layer of Au/Pd. Samples were imaged with a Zeiss Merlin Fe-SEM at 2.5 key, 83 pA probe current and 2.9 mm working distance (zero tilt) using the in-lens SE detector.

All publications and patent applications mentioned in this specification are herein incorporated by reference to the same extent as if each individual publication or patent application was specifically and individually indicated to be incorporated by reference.

Although the invention has been described with reference to the above examples, it will be understood that modifications and variations are encompassed within the spirit and scope of the invention. Accordingly, the invention is limited only by the following claims.

What is claimed is:

1. A method of delivering a nucleic acid molecule to a diatom comprising:
contacting the diatom with an *Escherichia coli* (*E. coli*) bacterium, wherein the *E. coli* bacterium comprises mobilization (MOB) and mating pair formation (MPF) genes and further comprises a DNA transfer construct comprising the nucleic acid molecule and an origin of transfer,
thereby delivering the nucleic acid molecule to the diatom.

2. The method of claim 1, wherein the diatom is a species of a genus selected from the group consisting of *Achnanthes, Amphora, Chaetoceros, Coscinodiscus, Cylindrotheca, Cyclotella, Cymbella, Fragilaria, Fragilariopsis, Hantzschia, Navicula, Nitzschia, Pavlova, Pseudo-Nitzschia, Phaeodactylum, Psammodictyon, Skeletonema, Thalassionema,* and *Thalassiosira*.

3. The method of claim 2, wherein the diatom is a species of *Cyclotella, Cylindrotheca, Phaeodactylum*, or *Thalassiosira*.

4. The method of claim 1, wherein the DNA transfer construct comprises an episomal maintenance cassette that comprises an autonomous replication sequence (ARS).

5. The method of claim 4, wherein the ARS is derived from a plant, alga, fungus or heterokont.

6. The method of claim 5, wherein the ARS is a yeast ARS.

7. The method of claim 6, wherein the ARS is *Saccharomyces* ARSH4 (SEQ ID NO:2) or a sequence having at least 80% identity thereto.

8. The method of claim 4, wherein the ARS is a synthetic ARS.

9. The method of claim 8, wherein the ARS is less than about 50% GC.

10. The method of claim 9, wherein the ARS is less than about 40% GC.

11. The method of claim 10, wherein the ARS less than or equal to about 30% GC.

12. The method of claim 4, wherein the episomal maintenance region comprises a centromere sequence.

13. The method of claim 12, wherein the centromere sequence is derived from a plant, alga, fungus, or heterokont.

14. The method of claim 13, wherein the centromere sequence comprises a yeast centromere sequence.

15. The method of claim 14, wherein the centromere sequence is *Saccharomyces* CEN6 (SEQ ID NO:1) or a sequence having at least 80% identity thereto.

16. The method of claim 1, wherein the DNA transfer construct comprises a selectable marker.

17. The method of claim 1, wherein the selectable marker is selected from the group consisting of an antibiotic resistance gene, a gene encoding a polypeptide conferring resistance to a toxin, an auxotrophic marker, and a combination thereof.

18. The method of claim 1, wherein the DNA transfer construct further comprises a reporter gene.

19. A method according to claim 16, wherein the DNA transfer construct becomes established as an episome in the algal cell.

20. The method of claim 1, wherein the nucleic acid molecule comprises at least one gene encoding a polypeptide or functional RNA.

21. The method of claim 20, wherein the at least one gene encodes a metabolic enzyme, a growth regulator, a transcription factor, a transcriptional activator, a transcriptional repressor, a polymerase, a nuclease, a transposase, a recombinase, an RNA binding protein, a component of a spliceosome, a component of a ribosome, a structural protein, an antibody or a subunit thereof, a peptide hormone, a cytoskeletal protein, a transporter, an ion channel, a receptor, a chaperonin, a kinase, a G protein, a phosphodiesterase, a nucleotide cyclase, or a photosynthetic protein.

22. The method of claim 20, wherein the nucleic acid molecule comprises at least two genes.

23. The method of claim 22, wherein the nucleic acid molecule comprises at least three genes.

24. The method of claim 1, wherein the DNA transfer construct is at least about 1 kb, 10 kb, 25 kb, 50 kb, 75 kb, 100 kb, 125 kb, 150 kb, 175 kb, 200 kb, 250 kb, 300 kb, 350 kb, 400 kb, 500 kb, 600 kb, 700 kb, 800 kb, 900 kb or 1 Mbp.

25. The method of claim 24, wherein the DNA transfer construct is at least about 100 kb.

26. The method of claim 1, wherein the contacting is performed at a temperature other than the optimal growth temperature of the diatom.

27. The method of claim 26, wherein the contacting is performed at a temperature closer to the optimal growth temperature of the bacterium than to the optimal growth temperature of the diatom.

28. The method of claim 27, wherein the contacting is performed at a temperature higher than the optimal growth temperature of the diatom and lower than the optimal growth temperature of the bacterium.

29. The method of claim 26, wherein the contacting is performed at a temperature of at least 25° C.

30. The method of claim 29, wherein the contacting is performed at a temperature of at least about 30° C.

31. The method of claim 1, wherein the contacting is performed for at least 10 minutes.

32. The method of claim 31, wherein the contacting is performed for at least 20 minutes.

33. The method of claim 32, wherein the contacting is performed for at least about 30 minutes.

* * * * *

SEQUENCE LISTING

<160> NUMBER OF SEQ ID NOS: 38

<210> SEQ ID NO 1
<211> LENGTH: 117
<212> TYPE: DNA
<213> ORGANISM: Saccharomyces cerevisiae
<220> FEATURE:
<221> NAME/KEY: misc_feature
<223> OTHER INFORMATION: CEN6

<400> SEQUENCE: 1

```
atcacgtgct ataaaaataa ttataattta aattttttaa tataaatata taaattaaaa      60
atagaaagta aaaaagaaa ttaaagaaaa aatagttttt gttttccgaa gatgtaa         117
```

<210> SEQ ID NO 2
<211> LENGTH: 388
<212> TYPE: DNA
<213> ORGANISM: Saccharomyces cerevisiae
<220> FEATURE:
<221> NAME/KEY: misc_feature
<223> OTHER INFORMATION: ARSH4

<400> SEQUENCE: 2

```
aagactctag ggggatcgcc aacaaatact accttttacc ttgctcttcc tgctctcagg      60
tattaatgcc gaattgtttc atcttgtctg tgtagaagac cacacacgaa atcctgtga      120
ttttacattt tacttatcgt taatcgaatg tatatctatt taatctgctt ttcttgtcta     180
ataaatatat atgtaaagta cgctttttgt tgaaattttt taaaccttg tttattttt      240
tttcttcatt ccgtaactct tctaccttct ttatttactt tctaaaatcc aaatacaaaa     300
cataaaaata aataaacaca gagtaaattc ccaaattatt ccatcattaa aagatacgag    360
gcgcgtgtaa gttacaggca agcgatcc                                          388
```

<210> SEQ ID NO 3
<211> LENGTH: 874
<212> TYPE: DNA
<213> ORGANISM: Saccharomyces cerevisiae
<220> FEATURE:
<221> NAME/KEY: misc_feature
<223> OTHER INFORMATION: HIS3

<400> SEQUENCE: 3

```
tagtacactc tatatttttt tatgcctcgg taatgatttt cattttttt ttccacctag      60
cggatgactc tttttttttc ttagcgattg gcattatcac ataatgaatt atacattata    120
taaagtaatg tgatttcttc gaagaatata ctaaaaaatg agcaggcaag ataaacgaag    180
gcaaagatga cagagcagaa agccctagta aagcgtatta caaatgaaac caagattcag    240
attgcgatct ctttaaaggg tggtcccta gcgatagagc actcgatctt cccagaaaaa    300
gaggcagaag cagtagcaga acaggccaca caatcgcaag tgattaacgt ccacacaggt    360
atagggtttc tggaccatat gatacatgct ctggccaagc attccggctg gtcgctaatc    420
gttgagtgca ttggtgactt acacatagac gaccatcaca ccactgaaga ctgcgggatt    480
gctctcggtc aagcttttaa agaggcccta ggggccgtgc gtggagtaaa aaggtttgga    540
tcaggatttg cgcctttgga tgaggcactt tccagagcgg tggtagatct ttcgaacagg    600
ccgtacgcag ttgtcgaact ggtttgcaa agggagaaag taggagatct ctcttgcgag    660
atgatcccgc atttcttga aagctttgca gaggctagca gaattaccct ccacgttgat    720
tgtctgcgag gcaagaatga tcatcaccgt agtgagagtg cgttcaaggc tcttgcggt    780
```

```
gccataagag aagccacctc gcccaatggt accaacgatg ttccctccac caaaggtgtt        840
cttatgtagt tttacacagg agtctggact tgac                                    874
```

<210> SEQ ID NO 4
<211> LENGTH: 505
<212> TYPE: DNA
<213> ORGANISM: Saccharomyces cerevisiae
<220> FEATURE:
<221> NAME/KEY: misc_feature
<223> OTHER INFORMATION: CEN6-ARSH4

<400> SEQUENCE: 4

```
atcacgtgct ataaaaataa ttataattta aattttttaa tataaatata taaattaaaa         60
atagaaagta aaaaagaaa ttaaagaaaa aatagttttt gttttccgaa gatgtaaaag        120
actctagggg gatcgccaac aaatactacc ttttaccttg ctcttcctgc tctcaggtat        180
taatgccgaa ttgtttcatc ttgtctgtgt agaagaccac acacgaaaat cctgtgattt        240
tacattttac ttatcgttaa tcgaatgtat atctatttaa tctgcttttc ttgtctaata        300
aatatatatg taaagtacgc tttttgttga aattttttaa acctttgttt attttttttt        360
cttcattccg taactcttct accttcttta tttactttct aaaatccaaa tacaaaacat        420
aaaaataaat aaacacagag taaattccca aattattcca tcattaaaag atacgaggcg        480
cgtgtaagtt acaggcaagc gatcc                                              505
```

<210> SEQ ID NO 5
<211> LENGTH: 1379
<212> TYPE: DNA
<213> ORGANISM: Saccharomyces cerevisiae
<220> FEATURE:
<221> NAME/KEY: misc_feature
<223> OTHER INFORMATION: CEN6-ARSH4-HIS3

<400> SEQUENCE: 5

```
atcacgtgct ataaaaataa ttataattta aattttttaa tataaatata taaattaaaa         60
atagaaagta aaaaagaaa ttaaagaaaa aatagttttt gttttccgaa gatgtaaaag        120
actctagggg gatcgccaac aaatactacc ttttaccttg ctcttcctgc tctcaggtat        180
taatgccgaa ttgtttcatc ttgtctgtgt agaagaccac acacgaaaat cctgtgattt        240
tacattttac ttatcgttaa tcgaatgtat atctatttaa tctgcttttc ttgtctaata        300
aatatatatg taaagtacgc tttttgttga aattttttaa acctttgttt attttttttt        360
cttcattccg taactcttct accttcttta tttactttct aaaatccaaa tacaaaacat        420
aaaaataaat aaacacagag taaattccca aattattcca tcattaaaag atacgaggcg        480
cgtgtaagtt acaggcaagc gatcctagta cactctatat ttttttatgc ctcggtaatg        540
attttcattt ttttttttcca cctagcggat gactcttttt ttttcttagc gattggcatt        600
atcacataat gaattataca ttatataaag taatgtgatt tcttcgaaga atatactaaa        660
aaatgagcag gcaagataaa cgaaggcaaa gatgacagag cagaaagccc tagtaaagcg        720
tattacaaat gaaaccaaga ttcagattgc gatctcttta agggtggtc ccctagcgat        780 agagcactcg atcttcccag aaaaagaggc agaagcagta gcagaacagg ccacacaatc        840
gcaagtgatt aacgtccaca caggtatagg gttctggac catatgatac atgctctggc        900
caagcattcc ggctggtcgc taatcgttga gtgcattggt gacttacaca tagacgacca        960
tcacaccact gaagactgcg ggattgctct cggtcaagct tttaaagagg ccctaggggc       1020
cgtgcgtgga gtaaaaaggt ttggatcagg atttgcgcct ttggatgagg cactttccag       1080
```

| | |
|---|---|
| agcggtggta gatctttcga acaggccgta cgcagttgtc gaacttggtt tgcaaaggga | 1140 |
| gaaagtagga gatctctctt gcgagatgat cccgcatttt cttgaaagct ttgcagaggc | 1200 |
| tagcagaatt accctccacg ttgattgtct gcgaggcaag aatgatcatc accgtagtga | 1260 |
| gagtgcgttc aaggctcttg cggttgccat aagagaagcc acctcgccca atggtaccaa | 1320 |
| cgatgttccc tccaccaaag gtgttcttat gtagttttac acaggagtct ggacttgac | 1379 |

<210> SEQ ID NO 6
<211> LENGTH: 13692
<212> TYPE: DNA
<213> ORGANISM: Artificial Sequence
<220> FEATURE:
<223> OTHER INFORMATION: Unknown
<220> FEATURE:
<221> NAME/KEY: misc_feature
<223> OTHER INFORMATION: Plasmid BK-RBYV

<400> SEQUENCE: 6

| | |
|---|---|
| ctcgagcgtt gcaggccatg ctgtccaggc aggtagatga cgaccatcag ggacagcttc | 60 |
| aaggatcgct cgcggctctt accagcctaa cttcgatcac tggaccgctg atcgtcacgg | 120 |
| cgatttatgc cgcctcggcg agcacatgga acgggttggc atggattgta ggcgccgccc | 180 |
| tataccttgt ctgcctcccc gcgttgcgtc gcggtgcatg gagccgggcc acctcgacct | 240 |
| gaatggaagc cggcggcacc tcgctaacgg attcaccact ccaagaattg agccaatca | 300 |
| attcttgcgg agaactgtga atgcgcaaac caacccttgg cagaacatat ccatcgcgtc | 360 |
| cgccatctcc agcagccgca cgcggcgcat cccccccccc ctttcaattc aattcatcat | 420 |
| tttttttttta ttcttttttt tgatttcggt ttctttgaaa ttttttttgat tcggtaatct | 480 |
| ccgaacagaa ggaagaacga aggaaggagc acagacttag attggtatat atacgcatat | 540 |
| gtagtgttga agaaacatga aattgcccag tattcttaac ccaactgcac agaacaaaaa | 600 |
| cctgcaggaa acgaagataa atcatgtcga aagctacata taaggaacgt gctgctactc | 660 |
| atcctagtcc tgttgctgcc aagctattta atatcatgca cgaaaagcaa acaaacttgt | 720 |
| gtgcttcatt ggatgttcgt accaccaagg aattactgga gttagttgaa gcattaggtc | 780 |
| ccaaaatttg tttactaaaa acacatgtgg atatcttgac tgattttttcc atggagggca | 840 |
| cagttaagcc gctaaaggca ttatccgcca agtacaattt tttactcttc gaagacagaa | 900 |
| aatttgctga cattggtaat acagtcaaat tgcagtactc tgcgggtgta tacagaatag | 960 |
| cagaatgggc agacattacg aatgcacacg gtgtggtggg cccaggtatt gttagcggtt | 1020 |
| tgaagcaggc ggcagaagaa gtaacaaagg aacctagagg cctttttgatg ttagcagaat | 1080 |
| tgtcatgcaa gggctcccta tctactggag aatatactaa gggtactgtt gacattgcga | 1140 |
| agagcgacaa agattttgtt atcggcttta ttgctcaaag agacatgggt ggaagagatg | 1200 |
| aaggttacga ttggttgatt atgacacccg gtgtgggttt agatgacaag ggagacgcat | 1260 |
| tgggtcaaca gtatagaacc gtggatgatg tggtctctac aggatctgac attattattg | 1320 |
| ttggaagagg actatttgca aagggaaggg atgctaaggt agagggtgaa cgttacagaa | 1380 |
| aagcaggctg ggaagcatat ttgagaagat gcggccagca aaactaaaaa actgtattat | 1440 |
| aagtaaatgc atgtatacta aactcacaaa ttagagcttc aatttaatta tatcagttat | 1500 |
| tactcgggcg taatgatttt tataatgacg aaaaaaaaaa aattggaaag aaaaggggggg | 1560 |
| gggggcagct tgggtcctg gccacggggtg cgcatgatcg tgctcctgtc gttgaggacc | 1620 |
| cggctaggct ggcggggttg ccttactggt tagcagaatg aatcaccgat acgcgagcga | 1680 |

```
acgtgaagcg actgctgctg caaaacgtct gcgacctgag caacaacatg aatggtcttc   1740
ggtttccgtg tttcgtaaag tctggaaacg cggaagtcag cgccctgcac cattatgttc   1800
cggatctgca tcgcaggatg ctgctggcta ccctgtggaa cacctacatc tgtattaacg   1860
aagcgctggc attgaccctg agtgattttt ctctggtccc gccgcatcca taccgccagt   1920
tgtttaccct cacaacgttc cagtaaccgg gcatgttcat catcagtaac ccgtatcgtg   1980
agcatcctct ctcgtttcat cgctcgagct ggttgccctc gccgctgggc tggcggccgt   2040
ctatggccct gcaaacgcgc cagaaacgcc gtcgaagccg tgtgcgagac accgcggccg   2100
gccgccggcg ttgtggatac ctcgcggaaa acttggccct cactgacaga tgaggggcgg   2160
acgttgacac ttgaggggcc gactcacccg gcgcggcgtt gacagatgag gggcaggctc   2220
gatttcggcc ggcgacgtgg agctggccag cctcgcaaat cggcgaaaac gcctgatttt   2280
acgcgagttt cccacagatg atgtggacaa gcctgggat aagtgccctg cggtattgac   2340
acttgagggg cgcgactact gacagatgag gggcgcgatc cttgacactt gaggggcaga   2400
gtgctgacag atgaggggcg cacctattga catttgaggg gctgtccaca ggcagaaaat   2460
ccagcatttg caaggtttc gccgttt cggccaccg ctaacctgtc ttttaacctg   2520
cttttaaacc aatatttata aaccttgttt ttaaccaggg ctgcgccctg tgcgcgtgac   2580
cgcgcacgcc gaaggggggt gccccccctt ctcgaaccct cccggtcgag tgagcgagga   2640
agcaccaggg aacagcactt atatattctg cttacacacg atgcctgaaa aaacttccct   2700
tggggttatc cacttatcca cggggatatt tttataatta tttttttat agttttaga   2760 tcttcttttt tagagcgcct tgtaggcctt tatccatgct ggttctagag aaggtgttgt   2820
gacaaattgc cctttcagtg tgacaaatca ccctcaaatg acagtcctgt ctgtgacaaa   2880
ttgcccttaa ccctgtgaca aattgccctc agaagaagct gttttttcac aaagttatcc   2940
ctgcttattg actctttttt atttagtgtg acaatctaaa aacttgtcac acttcacatg   3000
gatctgtcat ggcggaaaca gcggttatca atcacaagaa acgtaaaaat agcccgcgaa   3060
tcgtccagtc aaacgacctc actgaggcgg catatagtct ctcccgggat caaaaacgta   3120
tgctgtatct gttcgttgac cagatcagaa atctgatgg caccctacag gaacatgacg   3180
gtatctgcga gatccatgtt gctaaatatg ctgaaatatt cggattgacc tctgcggaag   3240
ccagtaagga tatacggcag gcattgaaga gtttcgcggg gaaggaagtg gttttttatc   3300
gccctgaaga ggatgccggc gatgaaaaag gctatgaatc ttttccttgg tttatcaaac   3360
gtgcgcacag tccatccaga gggctttaca gtgtacatat caacccatat ctcattccct   3420
tctttatcgg gttacagaac cggtttacgc agtttcggct tagtgaaaca aaagaaatca   3480
ccaatccgta tgccatgcgt ttatacgaat ccctgtgtca gtatcgtaag ccggatggct   3540
caggcatcgt ctctctgaaa atcgactgga tcatagagcg ttaccagctg cctcaaagtt   3600
accagcgtat gcctgacttc cgccgccgct tcctgcaggt ctgtgttaat gagatcaaca   3660
gcagaactcc aatgcgcctc tcatacattg agaaaaagaa aggccgccag acgactcata   3720
tcgtattttc cttccgcgat atcacttcca tgacgacagg atagtctgag ggttatctgt   3780
cacagatttg agggtggttc gtcacatttg ttctgaccta ctgagggtaa tttgtcacag   3840
ttttgctgtt ccttcagcc tgcatggatt ttctcatact ttttgaactg taattttaa   3900 ggaagccaaa tttgagggca gtttgtcaca gttgatttcc ttctctttcc cttcgtcatg   3960
tgacctgata tcgggggtta gttcgtcatc attgatgagg gttgattatc acagtttatt   4020
```

```
actctgaatt ggctatccgc gtgtgtacct ctacctggag ttttttcccac ggtggatatt    4080
tcttcttgcg ctgagcgtaa gagctatctg acagaacagt tcttctttgc ttcctcgcca    4140
gttcgctcgc tatgctcggt tacacggctg cggcgagcat cacgtgctat aaaaataatt    4200
ataatttaaa tttttttaata taaatatata aattaaaaat agaaagtaaa aaagaaattt    4260
aaagaaaaaa tagttttttgt tttccgaaga tgtaaaagac tctaggggga tcgccaacaa    4320
atactacctt ttatcttgct cttcctgctc tcaggtatta atgccgaatt gtttcatctt    4380
gtctgtgtag aagaccacac acgaaaatcc tgtgatttta cattttactt atcgttaatc    4440
gaatgtatat ctatttaatc tgcttttctt gtctaataaa tatatatgta aagtacgctt    4500
tttgttgaaa ttttttaaac ctttgtttat tttttttttct tcattccgta actcttctac    4560
cttctttatt tacttctaa aatccaaata caaaacataa aaataaataa acacagagta     4620
aattcccaaa ttattccatc attaaaagat acgaggcgcg tgtaagttac aggcaagcga    4680
tcctagtaca ctctatattt ttttatgcct cggtaatgat tttcattttt ttttttccac    4740
ctagcggatg actcttttttt tttcttagcg attggcatta tcacataatg aattatacat    4800
tatataaagt aatgtgatttt cttcgaagaa tatactaaaa aatgagcagg caagataaac    4860
gaaggcaaag atgacagagc agaaagccct agtaaagcgt attacaaatg aaaccaagat    4920
tcagattgcg atctctttaa agggtggtcc cctagcgata gagcactcga tcttcccaga    4980
aaaagaggca gaagcagtag cagaacaggc cacacaatcg caagtgatta acgtccacac    5040
aggtataggg tttctggacc atatgataca tgctctggcc aagcattccg gctggtcgct    5100
aatcgttgag tgcattggtg acttacacat agacgaccat cacaccactg aagactgcgg    5160
gattgctctc ggtcaagctt ttaaagaggc cctactggcg cgtggagtaa aaaggtttgg    5220
atcaggatttt gcgcctttgg atgaggcact ttccagagcg gtggtagatc tttcgaacag    5280
gccgtacgca gttgtcgaac ttggtttgca aagggagaaa gtaggagatc tctcttgcga    5340
gatgatcccg catttttcttg aaagctttgc agaggctagc agaattaccc tccacgttga    5400
ttgtctgcga ggcaagaatg atcatcaccg tagtgagagt gcgttcaagg ctcttgcggt    5460
tgccataaga gaagccacct cgcccaatgg taccaacgat gttccctcca ccaaaggtgt    5520
tcttatgtag ttttacacag gagtctggac ttgacgctag tgataataag tgactgaggt    5580
atgtgctctt cttatctcct tttgtagtgt tgctcttatt ttaaacaact ttgcggtttt    5640
ttgatgactt tgcgatttttg ttgttgcttt gcagtaaatt gcaagattta ataaaaaaac    5700
gcaaagcaat gattaaagga tgttcagaat gaaactcatg gaaacactta accagtgcat    5760
aaacgctggt catgaaatga cgaaggctat cgccattgca cagtttaatg atgacagccc    5820
ggaagcgagg aaaataaccc ggcgctggag aataggtgaa gcagcggatt tagttggggt    5880
ttcttctcag gctatcagag atgccgagaa agcagggcga ctaccgcacc cggatatgga    5940
aattcgagga cgggttgagc aacgtgttgg ttatacaatt gaacaaatta atcatatgcg    6000
tgatgtgttt ggtacgcgat tgcgacgtgc tgaagacgta tttccaccgg tgatcggggt    6060
tgctgcccat aaaggtggcg tttacaaaac ctcagtttct gttcatcttg ctcaggatct    6120
ggctctgaag gggctacgtg ttttgctcgt ggaaggtaac gacccccagg aacagcctc     6180
aatgtatcac ggatgggtac cagatcttca tattcatgca gaagacactc tcctgccttt    6240
ctatcttggg gaaaaggacg atgtcactta tgcaataaag cccacttgct ggccggggct    6300
tgacattatt ccttcctgtc tggctctgca ccgtattgaa actgagttaa tgggcaaatt    6360
tgatgaaggt aaactgccca ccgatccaca cctgatgctc cgactggcca ttgaaactgt    6420
```

```
tgctcatgac tatgatgtca tagttattga cagcgcgcct aacctgggta tcggcacgat     6480
taatgtcgta tgtgctgctg atgtgctgat tgttcccacg cctgctgagt tgtttgacta     6540
cacctccgca ctgcagtttt tcgatatgct tcgtgatctg ctcaagaacg ttgatcttaa     6600
agggttcgag cctgatgtac gtattttgct taccaaatac agcaatagca atggctctca     6660
gtccccgtgg atggaggagc aaattcggga tgcctgggga agcatggttc taaaaaatgt     6720
tgtacgtgaa acgatgaag ttggtaaagg tcagatccgg atgagaactg ttttttgaaca     6780 ggccattgat caacgctctt caactggtgc ctggagaaat gctctttcta tttgggaacc     6840
tgtctgcaat gaaattttcg atcgtctgat taaaccacgc tgggagatta gataatgaag     6900
cgtgcgcctg ttattccaaa acatacgctc aatactcaac cggttgaaga tacttcgtta     6960
tcgacaccag ctgccccgat ggtggattcg ttaattgcgc gctaggagt aatggctcgc     7020 ggtaatgcca ttactttgcc tgtatgtggt cgggatgtga agtttactct tgaagtgctc     7080
cggggtgata tgttgagaa gacctctcgg gtatggtcag gtaatgaacg tgaccaggag     7140
ctgcttactg aggacgcact ggatgatctc atcccttctt ttctactgac tggtcaacag     7200
acaccggcgt tcggtcgaag agtatctggt gtcatagaaa ttgccgatgg gagtcgccgt     7260
cgtaaagctg ctgcacttac cgaaagtgat tatcgtgttc tggttggcga gctggatgat     7320
gagcagatgg ctgcattatc cagattgggt aacgattatc gcccaacaag tgcttatgaa     7380
cgtggtcagc gttatgcaag ccgattgcag aatgaatttg ctggaaatat ttctgcgctg     7440
gctgatgcgg aaaatatttc acgtaagatt attacccgct gtatcaacac cgccaaattg     7500
cctaaatcag ttgttgctct tttttctcac cccggtgaac tatctgcccg tcaggtgat     7560 gcacttcaaa aagcctttac agataaagag gaattactta agcagcaggc atctaacctt     7620
catgagcaga aaaagctgg ggtgatattt gaagctgaag aagttatcac tcttttaact     7680
tctgtgctta aaacgtcatc tgcatcaaga actagtttaa gctcacgaca tcagtttgct     7740
cctggagcga cagtattgta aagggcgat aaaatggtgc ttaacctgga caggtctcgt     7800
gttccaactg agtgtataga gaaaattgag gccattctta aggaacttga aaagccagca     7860
ccctgatgcg accacgtttt agtctacgtt tatctgtctt tacttaatgt cctttgttac     7920
aggccagaaa gcataactgg cctgaatatt ctctctgggc ccactgttcc acttgtatcg     7980
tcggtctgat aatcagactg ggaccacggt cccactcgta tcgtcggtct gattattagt     8040
ctgggaccac ggtcccactc gtatcgtcgg tctgattatt agtctgggac cacggtccca     8100
ctcgtatcgt cggtctgata atcagactgg gaccacggtc ccactcgtat cgtcggtctg     8160
attattagtc tgggaccatg gtcccactcg tatcgtcggt ctgattatta gtctgggacc     8220
acggtcccac tcgtatcgtc ggtctgatta ttagtctgga accacggtcc cactcgtatc     8280
gtcggtctga ttattagtct gggaccacgg tcccactcgt atcgtcggtc tgattattag     8340
tctgggacca cgatcccact cgtgttgtcg gtctgattat cggtctggga ccacggtccc     8400
acttgtattg tcgatcagac tatcagcgtg agactacgat tccatcaatg cctgtcaagg     8460
gcaagtattg acatgtcgtc gtaacctgta gaacggagta acctcggtgt gcggttgtat     8520
gcctgctgtg gattgctgct gtgtcctgct tatccacaac attttgcgca cggttatgtg     8580
gacaaaatac ctggttaccc aggccgtgcc ggcacgttaa ccgggctgca tccgatgcaa     8640
gtgtgtcgct gtcgacgagc tcgcgagctc ggacatgagg ttgccccgta ttcagtgtcg     8700
ctgatttgta ttgtctgaag ttgttttttac gttaagttga tgcagatcaa ttaatacgat     8760
```

```
acctgcgtca taattgatta tttgacgtgg tttgatggcc tccacgcacg ttgtgatatg   8820
tagatgataa tcattatcac tttacgggtc ctttccggtg atccgacagg ttacggggcg   8880
gcgacctcgc gggttttcgc tatttatgaa aattttccgg tttaaggcgt ttccgttctt   8940
cttcgtcata acttaatgtt tttatttaaa ataccctctg aaaagaaagg aaacgacagg   9000
tgctgaaagc gagcttttg  gcctctgtcg tttcctttct ctgttttgt  ccgtggaatg   9060
aacaatggaa gtccgagctc atcgctaata acttcgtata gcatacatta tacgaagtta   9120
tattcgatgc ggccgcaagg ggttcgcgtc agcgggtgtt ggcgggtgtc ggggctggct   9180
taactatgcg gcatcagagc agattgtact gagagtgcac catatgcggt gtgaaatacc   9240
acacagatgc gtaaggagaa ataccgcat  caggcgccat tcgccattca gctgcgcaac   9300
tgttgggaag ggcgatcggt gcgggcctct tcgctattac gccagctggc gaaaggggga   9360
tgtgctgcaa ggcgattaag ttgggtaacg ccagggtttt cccagtcacg acgttgtaaa   9420
acgacggcca gtgaattgta atacgactca ctatagggcg aattcgagct cggtacccgg   9480
ggatcctcta gagtcgacct gcaggcatgc aagcttgagt attctatagt ctcacctaaa   9540
tagcttggcg taatcatggt catagctgtt tcctgtgtga aattgttatc cgctcacaat   9600
tccacacaac atacgagccg gaagcataaa gtgtaaagcc tggggtgcct aatgagtgag   9660
ctaactcaca ttaattgcgt tgcgctcact gcccgctttc cagtcgggaa acctgtcgtg   9720
ccagctgcat taatgaatcg gccaacgcga accccttgcg gccgcccggg ccgtcgacca   9780
attctcatgt ttgacagctt atcatcgaat ttctgccatt catccgctta ttatcactta   9840
ttcaggcgta gcaaccaggc gtttaagggc accataact  gccttaaaaa aattacgccc   9900
cgccctgcca ctcatcgcag tactgttgta attcattaag cattctgccg acatggaagc   9960
catcacaaac ggcatgatga acctgaatcg ccagcggcat cagcaccttg tcgccttgcg  10020
tataatattt gcccatggtg aaaacggggg cgaagaagtt gtccatattg gccacgttta  10080
aatcaaaact ggtgaaactc acccagggat tggctgagac gaaaaacata ttctcaataa  10140
acccttagg  gaaataggcc aggttttcac cgtaacacgc cacatcttgc gaatatatgt  10200
gtagaaactg ccggaaatcg tcgtggtatt cactccagag cgatgaaaac gtttcagttt  10260
gctcatggaa aacggtgtaa caagggtgaa cactatccca tatcaccagc tcaccgtctt  10320
tcattgccat acgaaattcc ggatgagcat tcatcaggcg ggcaagaatg tgaataaagg  10380
ccggataaaa cttgtgctta ttttttcttta cggtctttaa aaaggccgta atatccagct  10440
gaacggtctg gttataggta cattgagcaa ctgactgaaa tgcctcaaaa tgttctttac  10500
gatgccattg ggatatatca acggtggtat atccagtgat ttttttctcc attttagctt  10560
ccttagctcc tgaaaatctc gataactcaa aaaatacgcc cggtagtgat cttatttcat  10620
tatggtgaaa gttggaacct cttacgtgcc gatcaacgtc tcattttcgc caaaagttgg  10680
cccagggctt cccggtatca acagggacac caggatttat ttattctgcg aagtgatctt  10740
ccgtcacagg tatttattcg cgataagctc atggagcggc gtaaccgtcg cacaggaagg  10800
acagagaaag cgcggatctg ggaagtgacg gacagaacgg tcaggacctg gattggggag  10860
gcggttgccg ccgctgctgc tgacggtgtg acgttctctg ttccggtcac accacatacg  10920
ttccgccatt cctatgcgat gcacatgctg tatgccggta taccgctgaa agttctgcaa  10980
agcctgatgg gacataagtc catcagttca acggaagtct acacgaaggt ttttgcgctg  11040
gatgtggctg cccggcaccg ggtgcagttt gcgatgccgg agtctgatgc ggttgcgatg  11100
ctgaaacaat tatcctgaga ataaatgcct tggcctttat atggaaatgt ggaactgagt  11160
```

```
ggatatgctg tttttgtctg ttaaacagag aagctggctg ttatccactg agaagcgaac    11220
gaaacagtcg ggaaaatctc ccattatcgt agagatccgc attattaatc tcaggagcct    11280
gtgtagcgtt tataggaagt agtgttctgt catgatgcct gcaagcggta acgaaaacga    11340
tttgaatatg ccttcaggaa caatagaaat cttcgtgcgg tgttacgttg aagtggagcg    11400
gattatgtca gcaatggaca gaacaaccta atgaacacag aaccatgatg tggtctgtcc    11460
ttttacagcc agtagtgctc gccgcagtcg agcgacaggg cgaagcccac catgattacg    11520
ccaagctcga aattaaccct cactaaaggg aacaaaagct ggtacctaac aggattagtg    11580
caattcgagt tgaatcactg ggaaaaacat tgtcttcttt tttatattat catttgcatt    11640
agtgctgcag tcgtagatac ttgttggttg aaagacatca gctgggaggg actggactag    11700
cgtttggtaa ggagacatac ctgttaacgt tggttgcaaa attccatttc gcgatttatg    11760
ttatctgtaa atcctgattt gtctggaatt cttgatactt ccgttttttt agaggccaat    11820
gattagcatc ggcgattctc aaaatagcat tttcgacatg cggtgctgat ttcataaaca    11880
tagacaacgc ttttacatgt aaaagtaact tgcggacttg aacagtgct  ctgttttttgg   11940 tgtgaacgta actcagcaat atttctgtgc tagcaaggtt ttttatgatc gaccgaagat    12000
ctcaaaactc cgggtctttc aactgtctga ctagaccatg ttcgtaacgt cggacagcag    12060
ctttcgttgt actggtagaa tttctacgtg cgaagcacgt gtaggcaggt tgaacgacga    12120
tccctgccga tggatggatt ggcacgcggc ggaacgcttt cgtgatctac accacctgga    12180
tcttcacata tcttcgaaat cgaaaaatta accaagtcga cggtatcgat aatattctag    12240
ctgagggtac ccatggccaa gttgaccagt gccgttccgg tgctcaccgc gcgcgacgtc    12300 gccgagcgg  tcgagttctg gaccgaccgg ctcgggttct cccggacttc cgtgaggac     12360 gacttcgccg gtgtggtccg ggacgacgtg accctgttca tcagcgcggt ccaggaccag    12420
gtggtgccgg acaacaccct ggcctgggtg tgggtgcgcg gcctgacga  gctgtacgcc    12480 gagtggtcgg aggtcgtgtc cacgaacttc cgggacgcct ccgggccggc catgaccgag    12540
atcggcgagc agccgtgggg gcgggagttc gccctgcgcg accggccgg  caactgcgtg    12600 cacttcgtgg ccgaggagca ggactgaccg acgccgacca acaccgccgg tccgacgcgg    12660
cccgacgggt ccgaggcctc ggagatctgg gcccatgcgg ccgcaacaac tacctcgact    12720
ttggctggga cactttcagt gaggacaaga agcttcagaa gcgtgctatc gaactcaacc    12780
agggacgtgc ggcacaaatg ggcatccttg ctctcatggt gcacgaacag ttgggagtct    12840
ctatccttcc ttaaaatttt aattttcatt agttgcagtc actccgcttt ggtttcacag    12900
tcaggaataa cactagctcg tcttcacatc ttccgctgca taaccctgct tcggggtcat    12960
tatagcgatt ttttcggtat atccatcctt tttcgcacga tatacaggat tttgccaaag    13020
ggttcgcgta gactttcctt ggtgtatcca acggcgtcag ccgggcagga taggtgaagt    13080
aggcccaccc gcgagcgggt gttccttctt cactgtccct tattcgcacc tggcggtgct    13140
caacgggaat cctgctctgc gaggctggcc ggctaccgcc ggcgtaacag atgagggcaa    13200
gcggatggct gatgaaacca agccaaccag gaagggcagc ccacctatca aggtgtactg    13260
ccttccagac gaacgaagag cgattgagga aaaggcggcg gcggccggca tgagcctgtc    13320
ggcctacctg ctggccgtcg gccagggcta caaaatcacg ggcgtcgtgg actatgagca    13380
cgtccgcgag ctgcccgca  tcaatggcga cctgggccgc ctgggcggcc tgctgaaact    13440
ctggctcacc gacgacccgc gcacggcgcg gttcggtgat gccacgatcc tcgccctgct    13500
```

-continued

| | |
|---|---|
| ggcgaagatc gaagagaagc aggacgagct tggcaaggtc atgatgggcg tggtccgccc | 13560 |
| gagggcagag ccatgacttt tttcacgtaa cggatcgggg tgcgcgtgat tcggaagcac | 13620 |
| gttccatggc ctccatcaag aagaggcact tcgagctgta agtacatcac cgacgagcaa | 13680 |
| ggcaagacga tc | 13692 |

<210> SEQ ID NO 7
<211> LENGTH: 9500
<212> TYPE: DNA
<213> ORGANISM: Artificial Sequence
<220> FEATURE:
<223> OTHER INFORMATION: Unknown
<220> FEATURE:
<221> NAME/KEY: misc_feature
<223> OTHER INFORMATION: pCCBac1-LCyeast vector backbone

<400> SEQUENCE: 7

| | |
|---|---|
| ctggttgccc tcgccgctgg gctggcggcc gtctatggcc ctgcaaacgc gccagaaacg | 60 |
| ccgtcgaagc cgtgtgcgag acaccgcggc cggccgccgg cgttgtggat acctcgcgga | 120 |
| aaacttggcc ctcactgaca gatgaggggc ggacgttgac acttgagggg ccgactcacc | 180 |
| cggcgcggcg ttgacagatg aggggcaggc tcgatttcgg ccggcgacgt ggagctggcc | 240 |
| agcctcgcaa atcggcgaaa acgcctgatt ttacgcgagt ttcccacaga tgatgtggac | 300 |
| aagcctgggg ataagtgccc tgcggtattg acacttgagg ggcgcgacta ctgacagatg | 360 |
| aggggcgcga tccttgacac ttgaggggca gagtgctgac agatgagggg cgcacctatt | 420 |
| gacatttgag gggctgtcca caggcagaaa atccagcatt tgcaagggtt ccgcccgtt | 480 |
| tttcggccac cgctaacctg tcttttaacc tgcttttaaa ccaatattta taaaccttgt | 540 |
| ttttaaccag ggctgcgccc tgtgcgcgtg accgcgcacg ccgaaggggg gtgcccccc | 600 |
| ttctcgaacc ctcccggtcg agtgagcgag gaagcaccag ggaacagcac ttatatattc | 660 |
| tgcttacaca cgatgcctga aaaaacttcc cttggggtta tccacttatc cacgggggata | 720 |
| ttttttataat tatttttttt atagttttta gatcttcttt tttagagcgc cttgtaggcc | 780 |
| tttatccatg ctggttctag agaaggtgtt gtgacaaatt gcccttcag tgtgacaaat | 840 |
| caccctcaaa tgacagtcct gtctgtgaca aattgcccct taaccctgtga caaattgccc | 900 |
| tcagaagaag ctgttttttc acaaagttat ccctgcttat tgactctttt ttatttagtg | 960 |
| tgacaatcta aaaacttgtc acacttcaca tggatctgtc atggcggaaa cagcggttat | 1020 |
| caatcacaag aaacgtaaaa atagcccgcg aatcgtccag tcaaacgacc tcactgaggc | 1080 |
| ggcatatagt ctctcccggg atcaaaaacg tatgctgtat ctgttcgttg accagatcag | 1140 |
| aaaatctgat ggcaccctac aggaacatga cggtatctgc gagatccatg ttgctaaata | 1200 |
| tgctgaaata ttcggattga cctctgcgga agccagtaag gatatacggc aggcattgaa | 1260 |
| gagtttcgcg gggaaggaag tggttttta tcgccctgaa gaggatgccg gcgatgaaaa | 1320 |
| aggctatgaa tcttttcctt ggtttatcaa acgtgcgcac agtccatcca gagggcttta | 1380 |
| cagtgtacat atcaacccat atctcattcc cttctttatc gggttacaga accggtttac | 1440 |
| gcagtttcgg cttagtgaaa caaaagaaat caccaatccg tatgccatgc gtttatacga | 1500 |
| atccctgtgt cagtatcgta agccggatgg ctcaggcatc gtctctctga aaatcgactg | 1560 |
| gatcatagag cgttaccagc tgcctcaaag ttaccagcgt atgcctgact ccgccgccg | 1620 |
| cttcctgcag gtctgtgtta atgagatcaa cagcagaact ccaatgcgcc tctcatacat | 1680 |
| tgagaaaaag aaaggccgcc agacgactca tatcgtattt tccttccgcg atatcacttc | 1740 |

```
catgacgaca ggatagtctg agggttatct gtcacagatt tgagggtggt tcgtcacatt    1800
tgttctgacc tactgagggt aatttgtcac agttttgctg tttccttcag cctgcatgga    1860
ttttctcata cttttttgaac tgtaattttt aaggaagcca aatttgaggg cagtttgtca   1920
cagttgattt ccttctcttt cccttcgtca tgtgacctga tatcggggt tagttcgtca     1980
tcattgatga gggttgatta tcacagttta ttactctgaa ttggctatcc gcgtgtgtac    2040
ctctacctgg agttttccc acggtggata tttcttcttg cgctgagcgt aagagctatc     2100
tgacagaaca gttcttcttt gcttcctcgc cagttcgctc gctatgctcg gttacacggc    2160
tgcggcgagc atcacgtgct ataaaaataa ttataattta aatttttta taaaatata      2220
taaattaaaa atagaaagta aaaaagaaa ttaaagaaaa aatagttttt gttttccgaa      2280
gatgtaaaag actctagggg gatcgccaac aaatactacc ttttatcttg ctcttcctgc    2340
tctcaggtat taatgccgaa ttgtttcatc ttgtctgtgt agaagaccac acacgaaaat    2400
cctgtgattt tacattttac ttatcgttaa tcgaatgtat atctatttaa tctgcttttc    2460
ttgtctaata aatatatatg taaagtacgc ttttgttga aattttttaa acctttgttt     2520
atttttttt cttcattccg taactcttct accttcttta tttactttct aaaatccaaa     2580
tacaaaacat aaaaataaat aaacacagag taaattccca aattattcca tcattaaaag   2640
atacgaggcg cgtgtaagtt acaggcaagc gatcctagta cactctatat ttttttatgc    2700
ctcggtaatg atttcattt ttttttttcc acctagcgga tgactctttt tttttcttag    2760
cgattggcat tatcacataa tgaattatac attatataaa gtaatgtgat ttcttcgaag   2820
aatatactaa aaatgagca ggcaagataa acgaaggcaa agatgacaga gcagaaagcc    2880
ctagtaaagc gtattacaaa tgaaaccaag attcagattg cgatctcttt aaagggtggt   2940
cccctagcga tagagcactc gatcttccca gaaaaagagg cagaagcagt agcagaacag   3000
gccacacaat cgcaagtgat taacgtccac acaggtatag ggtttctgga ccatatgata   3060
catgctctgg ccaagcattc cggctggtcg ctaatcgttg agtgcattgg tgacttacac   3120
atagacgacc atcacaccac tgaagactgc gggattgctc tcggtcaagc ttttaaagag   3180
gccctactgg cgcgtggagt aaaaaggttt ggatcaggat ttgcgccttt ggatgaggca   3240
ctttccagag cggtggtaga tctttcgaac aggccgtacg cagttgtcga acttggtttg   3300
caaagggaga agtaggaga tctctcttgc gagatgatcc cgcattttct tgaaagcttt    3360
gcagaggcta gcagaattac cctccacgtt gattgtctgc gaggcaagaa tgatcatcac   3420
cgtagtgaga gtgcgttcaa ggctcttgcg gttgccataa gagaagccac ctcgcccaat   3480
ggtaccaacg atgttccctc caccaaaggt gttcttatgt agttttacac aggagtctgg   3540
acttgacgct agtgataata agtgactgag gtatgtgctc ttcttatctc cttttgtagt   3600
gttgctctta ttttaaacaa ctttgcggtt ttttgatgac tttgcgattt tgttgttgct   3660
ttgcagtaaa ttgcaagatt taataaaaaa acgcaaagca atgattaaag gatgttcaga   3720
atgaaactca tggaaacact taaccagtgc ataaacgctg gtcatgaaat gacgaaggct   3780
atcgccattg cacagtttaa tgatgacagc ccggaagcga ggaaaataac ccggcgctgg   3840
agaataggtg aagcagcgga tttagttggg gtttcttctc aggctatcag agatgccgag   3900
aaagcagggc gactaccgca cccggatatg gaaattcgag gacgggttga gcaacgtgtt   3960
ggttatacaa ttgaacaaat taatcatatg cgtgatgtgt ttggtacgcg attgcgacgt   4020
gctgaagacg tatttccacc ggtgatcggg gttgctgccc ataaaggtgg cgtttacaaa   4080
acctcagttt ctgttcatct tgctcaggat ctggctctga agggctacg tgttttgctc   4140
```

```
gtggaaggta acgaccccca gggaacagcc tcaatgtatc acggatgggt accagatctt   4200
catattcatg cagaagacac tctcctgcct ttctatcttg gggaaaagga cgatgtcact   4260
tatgcaataa agcccacttg ctggccgggg cttgacatta ttccttcctg tctggctctg   4320
caccgtattg aaactgagtt aatgggcaaa tttgatgaag gtaaactgcc caccgatcca   4380
cacctgatgc tccgactggc cattgaaact gttgctcatg actatgatgt catagttatt   4440
gacagcgcgc ctaacctggg tatcggcacg attaatgtcg tatgtgctgc tgatgtgctg   4500
attgttccca cgcctgctga gttgtttgac tacacctccg cactgcagtt tttcgatatg   4560
cttcgtgatc tgctcaagaa cgttgatctt aaagggttcg agcctgatgt acgtattttg   4620
cttaccaaat acagcaatag caatggctct cagtccccgt ggatggagga gcaaattcgg   4680
gatgcctggg gaagcatggt tctaaaaaat gttgtacgtg aaacggatga agttggtaaa   4740
ggtcagatcc ggatgagaac tgttttgaa caggccattg atcaacgctc ttcaactggt   4800
gcctggagaa atgctctttc tatttgggaa cctgtctgca tgaaattttt cgatcgtctg   4860
attaaaccac gctgggagat tagataatga agcgtgcgcc tgttattcca aaacatacgc   4920
tcaatactca accggttgaa gatacttcgt tatcgacacc agctgccccg atggtggatt   4980
cgttaattgc gcgcgtagga gtaatggctc gcggtaatgc cattactttg cctgtatgtg   5040
gtcgggatgt gaagtttact cttgaagtgc tccggggtga tagtgttgag aagacctctc   5100
gggtatggtc aggtaatgaa cgtgaccagg agctgcttac tgaggacgca ctggatgatc   5160
tcatcccttc ttttctactg actggtcaac agacaccggc gttcggtcga agagtatctg   5220
gtgtcataga aattgccgat gggagtcgcc gtcgtaaagc tgctgcactt accgaaagtg   5280
attatcgtgt tctggttggc gagctggatg atgagcagat ggctgcatta tccagattgg   5340
gtaacgatta tcgcccaaca agtgcttatg aacgtggtca gcgttatgca agccgattgc   5400
agaatgaatt tgctggaaat atttctgcgc tggctgatgc ggaaaatatt tcacgtaaga   5460
ttattacccg ctgtatcaac accgccaaat tgcctaaatc agttgttgct cttttttctc   5520
accccggtga actatctgcc cggtcaggtg atgcacttca aaaagccttt acagataaag   5580
aggaattact taagcagcag gcatctaacc ttcatgagca gaaaaaagct ggggtgatat   5640
ttgaagctga agaagttatc actcttttaa cttctgtgct taaaacgtca tctgcatcaa   5700
gaactagttt aagctcacga catcagtttg ctcctggagc gacagtattg tataagggcg   5760
ataaaatggt gcttaacctg gacaggtctc gtgttccaac tgagtgtata gagaaaattg   5820
aggccattct taaggaactt gaaaagccag caccctgatg cgaccacgtt ttagtctacg   5880
tttatctgtc tttacttaat gtcctttgtt acaggccaga aagcataact ggcctgaata   5940
ttctctctgg gcccactgtt ccacttgtat cgtcggtctg ataatcagac tgggaccacg   6000
gtcccactcg tatcgtcggt ctgattatta gtctgggacc acggtcccac tcgtatcgtc   6060
ggtctgatta ttagtctggg accacggtcc cactcgtatc gtcggtctga taatcagact   6120
gggaccacgg tcccactcgt atcgtcggtc tgattattag tctgggacca tggtcccact   6180
cgtatcgtcg gtctgattat tagtctggga ccacggtccc actcgtatcg tcggtctgat   6240
tattagtctg gaaccacggt cccactcgta tcgtcggtct gattattagt ctgggaccac   6300
ggtcccactc gtatcgtcgg tctgattatt agtctgggac cacgatccca ctcgtgttgt   6360
cggtctgatt atcggtctgg gaccacggtc ccacttgtat tgtcgatcag actatcagcg   6420
tgagactacg attccatcaa tgcctgtcaa gggcaagtat tgacatgtcg tcgtaacctg   6480
```

```
tagaacggag taacctcggt gtgcggttgt atgcctgctg tggattgctg ctgtgtcctg    6540
cttatccaca acattttgcg cacggttatg tggacaaaat acctggttac ccaggccgtg    6600
ccggcacgtt aaccgggctg catccgatgc aagtgtgtcg ctgtcgacga gctcgcgagc    6660
tcggacatga ggttgccccg tattcagtgt cgctgatttg tattgtctga agttgttttt    6720
acgttaagtt gatgcagatc aattaatacg atacctgcgt cataattgat tatttgacgt    6780
ggtttgatgg cctccacgca cgttgtgata tgtagatgat aatcattatc acttacggg    6840
tcctttccgg tgatccgaca ggttacgggg cggcgacctc gcgggttttc gctatttatg    6900
aaaattttcc ggtttaaggc gtttccgttc ttcttcgtca taacttaatg tttttattta    6960
aaataccctc tgaaaagaaa ggaaacgaca ggtgctgaaa gcgagctttt tggcctctgt    7020
cgtttccttt ctctgttttt gtccgtggaa tgaacaatgg aagtccgagc tcatcgctaa    7080
taacttcgta tagcatacat tatacgaagt tatattcgat gcggccgcaa ggggttcgcg    7140
tcagcgggtg ttggcgggtg tcggggctgg cttaactatg cggcatcaga gcagattgta    7200
ctgagagtgc accatatgcg gtgtgaaata ccacacagat gcgtaaggag aaaataccgc    7260
atcaggcgcc attcgccatt cagctgcgca actgttggga agggcgatcg gtgcgggcct    7320
cttcgctatt acgccagctg gcgaaagggg gatgtgctgc aaggcgatta agttgggtaa    7380
cgccagggtt ttcccagtca cgacgttgta aaacgacggc cagtgaattg taatacgact    7440
cactataggg cgaattcgag ctcggtaccc ggggatcctc tagagtcgac ctgcaggcat    7500
gcaagcttga gtattctata gtctcaccta aatagcttgg cgtaatcatg gtcatagctg    7560
tttcctgtgt gaaattgtta tccgctcaca attccacaca acatacgagc cggaagcata    7620
aagtgtaaag cctggggtgc ctaatgagtg agctaactca cattaattgc gttgcgctca    7680
ctgcccgctt tccagtcggg aaacctgtcg tgccagctgc attaatgaat cggccaacgc    7740
gaacccttg cggccgcccg ggccgtcgac caattctcat gtttgacagc ttatcatcga    7800
atttctgcca ttcatccgct tattatcact tattcaggcg tagcaaccag gcgtttaagg    7860
gcaccaataa ctgccttaaa aaattacgc cccgccctgc cactcatcgc agtactgttg    7920
taattcatta agcattctgc cgacatggaa gccatcacaa acggcatgat gaacctgaat    7980
cgccagcggc atcagcacct tgtcgccttg cgtataatat ttgcccatgg tgaaaacggg    8040
ggcgaagaag ttgtccatat tggccacgtt taaatcaaaa ctggtgaaac tcacccaggg    8100
attggctgag acgaaaaaca tattctcaat aaacccttta gggaaatagg ccaggttttc    8160
accgtaacac gccacatctt gcgaatatat gtgtagaaac tgccggaaat cgtcgtggta    8220
ttcactccag agcgatgaaa acgtttcagt ttgctcatgg aaaacggtgt aacaagggtg    8280
aacactatcc catatcacca gctcaccgtc tttcattgcc atacgaaatt ccggatgagc    8340
attcatcagg cgggcaagaa tgtgaataaa ggccggataa aacttgtgct tatttttctt    8400
tacggtcttt aaaaaggccg taatatccag ctgaacggtc tggttatagg tacattgagc    8460
aactgactga aatgcctcaa aatgttcttt acgatgccat tgggatatat caacggtggt    8520
atatccagtg atttttttct ccattttagc ttccttagct cctgaaaatc tcgataactc    8580
aaaaaatacg cccggtagtg atcttatttc attatggtga agttggaac ctcttacgtg    8640
ccgatcaacg tctcatttc gccaaaagtt ggcccaggc ttcccggtat caacagggac    8700
accaggattt atttattctg cgaagtgatc ttccgtcaca ggtatttatt cgcgataagc    8760
tcatggagcg cgtaaccgt cgcacaggaa ggacagagaa agcgcggatc tgggaagtga    8820
cggacagaac ggtcaggacc tggattgggg aggcggttgc cgccgctgct gctgacggtg    8880
```

| | |
|---|---|
| tgacgttctc tgttccggtc acaccacata cgttccgcca ttcctatgcg atgcacatgc | 8940 |
| tgtatgccgg tataccgctg aaagttctgc aaagcctgat gggacataag tccatcagtt | 9000 |
| caacggaagt ctacacgaag gttttttgcgc tggatgtggc tgcccggcac cgggtgcagt | 9060 |
| ttgcgatgcc ggagtctgat gcggttgcga tgctgaaaca attatcctga aataaatgc | 9120 |
| cttggccttt atatggaaat gtggaactga gtggatatgc tgttttttgtc tgttaaacag | 9180 |
| agaagctggc tgttatccac tgagaagcga acgaaacagt cgggaaaatc tcccattatc | 9240 |
| gtagagatcc gcattattaa tctcaggagc ctgtgtagcg tttataggaa gtagtgttct | 9300 |
| gtcatgatgc ctgcaagcgg taacgaaaac gatttgaata tgccttcagg aacaatagaa | 9360 |
| atcttcgtgc ggtgttacgt tgaagtggag cggattatgt cagcaatgga cagaacaacc | 9420 |
| taatgaacac agaaccatga tgtggtctgt cctttacag ccagtagtgc tcgccgcagt | 9480 |
| cgagcgacag ggcgaagccc | 9500 |

<210> SEQ ID NO 8
<211> LENGTH: 1418
<212> TYPE: DNA
<213> ORGANISM: Artificial Sequence
<220> FEATURE:
<223> OTHER INFORMATION: Unknown
<220> FEATURE:
<221> NAME/KEY: misc_feature
<223> OTHER INFORMATION: Shble cassette

<400> SEQUENCE: 8

| | |
|---|---|
| accatgatta cgccaagctc gaaattaacc ctcactaaag ggaacaaaag ctggtaccta | 60 |
| acaggattag tgcaattcga gttgaatcac tgggaaaaac attgtcttct tttttatatt | 120 |
| atcatttgca ttagtgctgc agtcgtagat acttgttggt tgaaagacat cagctgggag | 180 |
| ggactggact agcgtttggt aaggagacat acctgttaac gttggttgca aaattccatt | 240 |
| tcgcgattta tgttatctgt aaatcctgat ttgtctggaa ttcttgatac ttccgttttt | 300 |
| ttagaggcca atgattagca tcggcgattc tcaaaatagc attttcgaca tgcggtgctg | 360 |
| atttcataaa catagacaac gcttttacat gtaaaagtaa cttgcggact tggaacagtg | 420 |
| ctctgttttt ggtgtgaacg taactcagca atatttctgt gctagcaagg ttttttatga | 480 |
| tcgaccgaag atctcaaaac tccgggtctt tcaactgtct gactagacca tgttcgtaac | 540 |
| gtcggacagc agctttcgtt gtactggtag aatttctacg tgcgaagcac gtgtaggcag | 600 |
| gttgaacgac gatccctgcc gatggatgga ttggcacgcg gcggaacgct tcgtgatct | 660 |
| acaccacctg gatcttcaca tatcttcgaa atcgaaaaat taaccaagtc gacggtatcg | 720 |
| ataatattct agctgagggt acccatggcc aagttgacca gtgccgttcc ggtgctcacc | 780 |
| gcgcgcgacg tcgccggagc ggtcgagttc tggaccgacc ggctcgggtt ctcccgggac | 840 |
| ttcgtggagg acgacttcgc cggtgtggtc cgggacgacg tgaccctgtt catcagcgcg | 900 |
| gtccaggacc aggtggtgcc ggacaacacc ctggcctggg tgtgggtgcg cggcctggac | 960 |
| gagctgtacg ccgagtggtc ggaggtcgtg tccacgaact tccgggacgc ctccgggccg | 1020 |
| gccatgaccg agatcggcga gcagccgtgg gggcgggagt cgccctgcg cgacccggcc | 1080 |
| ggcaactgcg tgcacttcgt ggccgaggag caggactgac cgacgccgac caacaccgcc | 1140 |
| ggtccgacgc ggcccgacgg gtccgaggcc tcggagatct gggcccatgc ggccgcaaca | 1200 |
| actacctcga ctttggctgg gacactttca gtgaggacaa gaagcttcag aagcgtgcta | 1260 |
| tcgaactcaa ccaggacgt gcggcacaaa tgggcatcct tgctctcatg gtgcacgaac | 1320 |

```
agttgggagt ctctatcctt ccttaaaaat ttaattttca ttagttgcag tcactccgct    1380
ttggtttcac agtcaggaat aacactagct cgtcttca                            1418

<210> SEQ ID NO 9
<211> LENGTH: 647
<212> TYPE: DNA
<213> ORGANISM: Phaeodactylum tricornutum
<220> FEATURE:
<221> NAME/KEY: misc_feature
<223> OTHER INFORMATION: FcpF promoter

<400> SEQUENCE: 9
caggattagt gcaattcgag ttgaatcact gggaaaaaca ttgtcttctt ttttatatta      60
tcatttgcat tagtgctgca gtcgtagata cttgttggtt gaaagacatc agctgggagg     120
gactggacta gcgtttggta aggagacata cctgttaact tggttgcaa aattccattt      180 cgcgatttat gttatctgta aatcctgatt tgtctggaat tcttgatact tccgtttttt    240
tagaggccaa tgattagcat cggcgattct caaaatagca ttttcgacat gcggtgctga     300
tttcataaac atagacaacg cttttacatg taaaagtaac ttgcggactt ggaacagtgc     360 tctgttttg gtgtgaacgt aactcagcaa tatttctgtg ctagcaaggt tttttatgat     420
cgaccgaaga tctcaaaact ccgggtcttt caactgtctg actagaccat gttcgtaacg    480
tcggacagca gctttcgttg tactggtaga atttctacgt gcgaagcacg tgtaggcagg    540
ttgaacgacg atccctgccg atggatggat tggcacgcgg cggaacgctt tcgtgatcta    600
caccacctgg atcttcacat atcttcgaaa tcgaaaaatt aaccaag                  647

<210> SEQ ID NO 10
<211> LENGTH: 375
<212> TYPE: DNA
<213> ORGANISM: Streptoalloteichus hindustanus
<220> FEATURE:
<221> NAME/KEY: misc_feature
<223> OTHER INFORMATION: Ble gene

<400> SEQUENCE: 10
atggccaagt tgaccagtgc cgttccggtg ctcaccgcgc gcgacgtcgc cggagcggtc     60
gagttctgga ccgaccggct cgggttctcc cgggacttcg tggaggacga cttcgccggt    120
gtggtccggg acgacgtgac cctgttcatc agcgcggtcc aggaccaggt ggtgccggac    180
aacaccctgg cctgggtgtg ggtgcgcggc ctggacgagc tgtacgccga gtggtcggag    240
gtcgtgtcca cgaacttccg ggacgcctcc gggccggcca tgaccgagat cggcgagcag    300
ccgtgggggc gggagttcgc cctgcgcgac ccggccggca actgcgtgca cttcgtggcc    360
gaggagcagg actga                                                     375

<210> SEQ ID NO 11
<211> LENGTH: 195
<212> TYPE: DNA
<213> ORGANISM: Phaeodactylum tricornutum
<220> FEATURE:
<221> NAME/KEY: misc_feature
<223> OTHER INFORMATION: FcpA terminator

<400> SEQUENCE: 11
ccgcaacaac tacctcgact ttggctggga cactttcagt gaggacaaga agcttcagaa      60
gcgtgctatc gaactcaacc agggacgtgc ggcacaaatg ggcatccttg ctctcatggt    120
gcacgaacag ttgggagtct ctatccttcc ttaaaaattt aattttcatt agttgcagtc    180
```
actccgcttt ggttt                                                                195

<210> SEQ ID NO 12
<211> LENGTH: 766
<212> TYPE: DNA
<213> ORGANISM: Escherichia coli
<220> FEATURE:
<221> NAME/KEY: misc_feature
<223> OTHER INFORMATION: OriT

<400> SEQUENCE: 12
catcttccgc tgcataaccc tgcttcgggg tcattatagc gatttttcg gtatatccat      60 ccttttcgc acgatataca ggattttgcc aaagggttcg cgtagacttt ccttggtgta     120
tccaacggcg tcagccgggc aggataggtg aagtaggccc acccgcgagc gggtgttcct    180
tcttcactgt cccttattcg cacctggcgg tgctcaacgg gaatcctgct ctgcgaggct    240
ggccggctac cgccggcgta acagatgagg gcaagcggat ggctgatgaa accaagccaa    300
ccaggaaggg cagcccacct atcaaggtgt actgccttcc agacgaacga agagcgattg    360
aggaaaaggc ggcggcggcc ggcatgagcc tgtcggccta cctgctggcc gtcggccagg    420
gctacaaaat cacgggcgtc gtggactatg agcacgtccg cgagctggcc cgcatcaatg    480
gcgacctggg ccgcctgggc ggcctgctga actctggct caccgacgac ccgcgcacgg    540
cgcggttcgg tgatgccacg atcctcgccc tgctggcgaa gatcgaagag aagcaggacg    600
agcttggcaa ggtcatgatg ggcgtggtcc gcccgagggc agagccatga ctttttcac    660 gtaacggatc ggggtgcgcg tgattcggaa gcacgttcca tggcctccat caagaagagg    720
cacttcgagc tgtaagtaca tcaccgacga gcaaggcaag acgatc                   766

<210> SEQ ID NO 13
<211> LENGTH: 1996
<212> TYPE: DNA
<213> ORGANISM: Saccharomyces cerevisiae
<220> FEATURE:
<221> NAME/KEY: misc_feature
<223> OTHER INFORMATION: URA3

<400> SEQUENCE: 13
cgttgcaggc catgctgtcc aggcaggtag atgacgacca tcagggacag cttcaaggat      60
cgctcgcggc tcttaccagc ctaacttcga tcactggacc gctgatcgtc acggcgattt    120
atgccgcctc ggcgagcaca tggaacgggt tggcatggat tgtaggcgcc gccctatacc    180
ttgtctgcct ccccgcgttg cgtcgcggtg catggagccg gccaccttcg acctgaatgg    240
aagccggcgg cacctcgcta acggattcac cactccaaga attggagcca atcaattctt    300
gcggagaact gtgaatgcgc aaaccaaccc ttggcagaac atatccatcg cgtccgccat    360
ctccagcagc cgcacgcggc gcatcccccc ccccctttca attcaattca tcattttttt    420
tttattcttt tttttgattt cggtttcttt gaaatttttt tgattcggta atctccgaac    480
agaaggaaga acgaaggaag gagcacagac ttagattggt atatatacgc atatgtagtg    540
ttgaagaaac atgaaattgc ccagtattct taacccaact gcacagaaca aaaacctgca    600
ggaaacgaag ataaatcatg tcgaaagcta catataagga acgtgctgct actcatccta    660
gtcctgttgc tgccaagcta tttaatatca tgcacgaaaa gcaaacaaac ttgtgtgctt    720
cattggatgt tcgtaccacc aaggaattac tggagttagt tgaagcatta ggtcccaaaa    780
tttgtttact aaaaacacat gtggatatct tgactgattt ttccatggag ggcacagtta    840

```
agccgctaaa ggcattatcc gccaagtaca atttttact cttcgaagac agaaaatttg    900
ctgacattgg taatacagtc aaattgcagt actctgcggg tgtatacaga atagcagaat    960
gggcagacat tacgaatgca cacggtgtgg tgggcccagg tattgttagc ggttttgaagc   1020 aggcggcaga agaagtaaca aaggaaccta gaggcctttt gatgttagca gaattgtcat   1080
gcaagggctc cctatctact ggagaatata ctaagggtac tgttgacatt gcgaagagcg   1140
acaaagattt tgttatcggc tttattgctc aaagagacat gggtggaaga gatgaaggtt   1200
acgattggtt gattatgaca cccggtgtgg gtttagatga caagggagac gcattgggtc   1260
aacagtatag aaccgtggat gatgtggtct ctacaggatc tgacattatt attgttggaa   1320
gaggactatt tgcaaaggga agggatgcta aggtagaggg tgaacgttac agaaaagcag   1380
gctgggaagc atatttgaga agatgcggcc agcaaaacta aaaaactgta ttataagtaa   1440
atgcatgtat actaaactca caaattagag cttcaattta attatatcag ttattactcg   1500
ggcgtaatga ttttataat gacgaaaaaa aaaaaattgg aaagaaaagg ggggggggc    1560 agcgttgggt cctggccacg ggtgcgcatg atcgtgctcc tgtcgttgag gacccggcta   1620
ggctggcggg gttgccttac tggttagcag aatgaatcac cgatacgcga gcgaacgtga   1680
agcgactgct gctgcaaaac gtctgcgacc tgagcaacaa catgaatggt cttcggtttc   1740
cgtgtttcgt aaagtctgga aacgcggaag tcagcgccct gcaccattat gttccggatc   1800
tgcatcgcag gatgctgctg ctaccctgt ggaacaccta catctgtatt aacgaagcgc   1860
tggcattgac cctgagtgat ttttctctgg tcccgccgca tccataccgc cagttgttta   1920
ccctcacaac gttccagtaa ccgggcatgt tcatcatcag taacccgtat cgtgagcatc   1980
ctctctcgtt tcatcg                                                    1996

<210> SEQ ID NO 14
<211> LENGTH: 60
<212> TYPE: DNA
<213> ORGANISM: Artificial Sequence
<220> FEATURE:
<223> OTHER INFORMATION: Primer NewXFP1

<400> SEQUENCE: 14
gggttttccc agtcacgacg ttgtaaaacg acggccagtg agcgaacaga agacccaatc    60

<210> SEQ ID NO 15
<211> LENGTH: 60
<212> TYPE: DNA
<213> ORGANISM: Artificial Sequence
<220> FEATURE:
<223> OTHER INFORMATION: Primer NewXFP12

<400> SEQUENCE: 15
caccaccccg gtgaacagct cctcgccctt gctcaccatc gttcgcacaa gtggtgactt    60

<210> SEQ ID NO 16
<211> LENGTH: 60
<212> TYPE: DNA
<213> ORGANISM: Artificial Sequence
<220> FEATURE:
<223> OTHER INFORMATION: Primer NewXFP13

<400> SEQUENCE: 16
tccagcaacc attctcattc aaagtcacca cttgtgcgaa cgatggtgag caagggcgag    60

<210> SEQ ID NO 17
<211> LENGTH: 60
```

```
<212> TYPE: DNA
<213> ORGANISM: Artificial Sequence
<220> FEATURE:
<223> OTHER INFORMATION: Primer NewXFP14

<400> SEQUENCE: 17
aaagtgcaaa attgatatga caatcagtca agaactttta         60
cttgtacagc tcgtccatgc

<210> SEQ ID NO 18
<211> LENGTH: 60
<212> TYPE: DNA
<213> ORGANISM: Artificial Sequence
<220> FEATURE:
<223> OTHER INFORMATION: Primer NewXFP15

<400> SEQUENCE: 18
tcactctcgg catggacgag ctgtacaagt aaaagttctt         60
gactgattgt catatcaatt

<210> SEQ ID NO 19
<211> LENGTH: 60
<212> TYPE: DNA
<213> ORGANISM: Artificial Sequence
<220> FEATURE:
<223> OTHER INFORMATION: Primer NewXFP16

<400> SEQUENCE: 19
tttcacacag gaaacagcta tgaccatgat tacgccacag         60
actgctttag aggaagacgg

<210> SEQ ID NO 20
<211> LENGTH: 60
<212> TYPE: DNA
<213> ORGANISM: Artificial Sequence
<220> FEATURE:
<223> OTHER INFORMATION: Primer NewXFPF4

<400> SEQUENCE: 20
ataacactag ctcgtcttca cgtaactata acggtcctaa         60
agcgaacaga agacccaatc

<210> SEQ ID NO 21
<211> LENGTH: 60
<212> TYPE: DNA
<213> ORGANISM: Artificial Sequence
<220> FEATURE:
<223> OTHER INFORMATION: Primer NewXFPR2

<400> SEQUENCE: 21
agggttatgc agcggaagat ctatattacc ctgttatcag         60
actgctttag aggaagacgg

<210> SEQ ID NO 22
<211> LENGTH: 60
<212> TYPE: DNA
<213> ORGANISM: Artificial Sequence
<220> FEATURE:
<223> OTHER INFORMATION: Primer NewXFP11

<400> SEQUENCE: 22
tcacaagttt gtacaaaaaa gcaggctccg cggccgcccc         60
cttatgcgca gcctcgacgg

<210> SEQ ID NO 23
<211> LENGTH: 60
<212> TYPE: DNA
<213> ORGANISM: Artificial Sequence
<220> FEATURE:
<223> OTHER INFORMATION: Primer HA-MtUT-YFP-Term-4

<400> SEQUENCE: 23
```
gcaccacccc ggtgaacagc tcctcgccct tgctcaccat ctggttttgt tccggcgaat      60

<210> SEQ ID NO 24
<211> LENGTH: 60
<212> TYPE: DNA
<213> ORGANISM: Artificial Sequence
<220> FEATURE:
<223> OTHER INFORMATION: Primer HA-MtUT-YFP-Term-5

<400> SEQUENCE: 24
cttgaactag cgacgaatcc gcattcgccg gaacaaaacc agatggtgag caagggcgag      60

<210> SEQ ID NO 25
<211> LENGTH: 60
<212> TYPE: DNA
<213> ORGANISM: Artificial Sequence
<220> FEATURE:
<223> OTHER INFORMATION: Primer HA-MtUT-YFP-Term-6

<400> SEQUENCE: 25
gtcctcactg aaagtgtccc agccaaagtc gaggtagtta cttgtacagc tcgtccatgc      60

<210> SEQ ID NO 26
<211> LENGTH: 60
<212> TYPE: DNA
<213> ORGANISM: Artificial Sequence
<220> FEATURE:
<223> OTHER INFORMATION: Primer NewXFP9

<400> SEQUENCE: 26
ttcccagtca cgacgttgta aaacgacggc cagtgaatct cgcctattca tggtgtatac      60

<210> SEQ ID NO 27
<211> LENGTH: 60
<212> TYPE: DNA
<213> ORGANISM: Artificial Sequence
<220> FEATURE:
<223> OTHER INFORMATION: Primer NewXFP10

<400> SEQUENCE: 27
tcccaaagat acgtctaccg tagcgaccgt cgaggctgcg cataaggggg cggccgcgga      60

<210> SEQ ID NO 28
<211> LENGTH: 60
<212> TYPE: DNA
<213> ORGANISM: Artificial Sequence
<220> FEATURE:
<223> OTHER INFORMATION: Primer HA-MtUT-YFP-Term-7

<400> SEQUENCE: 28
cgccgggatc actctcggca tggacgagct gtacaagtaa ctacctcgac tttggctggg      60

<210> SEQ ID NO 29
<211> LENGTH: 60
<212> TYPE: DNA
<213> ORGANISM: Artificial Sequence
<220> FEATURE:
<223> OTHER INFORMATION: Primer HA-MtUT-YFP-Term-8

<400> SEQUENCE: 29
cacacaggaa acagctatga ccatgattac gccagttgaa gacgagctag tgttattcct      60

<210> SEQ ID NO 30
<211> LENGTH: 65
<212> TYPE: DNA
<213> ORGANISM: Artificial Sequence
<220> FEATURE:
<223> OTHER INFORMATION: Primer YeastXFPF5

<400> SEQUENCE: 30
ataacactag ctcgtcttca cgtaactata acggtcctaa aatctcgcct attcatggtg     60
tatac                                                                65

<210> SEQ ID NO 31
<211> LENGTH: 60
<212> TYPE: DNA
<213> ORGANISM: Artificial Sequence
<220> FEATURE:
<223> OTHER INFORMATION: Primer YeastXFPR1

<400> SEQUENCE: 31
gttatgcagc ggaagatcta tattaccctg ttatgttgaa gacgagctag tgttattcct     60

<210> SEQ ID NO 32
<211> LENGTH: 58
<212> TYPE: DNA
<213> ORGANISM: Artificial Sequence
<220> FEATURE:
<223> OTHER INFORMATION: Primer YeastXFPF2

<400> SEQUENCE: 32
ataacactag ctcgtcttca cgtaactata acggtcctaa agggcgaatt ggagctcc       58

<210> SEQ ID NO 33
<211> LENGTH: 60
<212> TYPE: DNA
<213> ORGANISM: Artificial Sequence
<220> FEATURE:
<223> OTHER INFORMATION: Primer YeastXFPR1

<400> SEQUENCE: 33
gttatgcagc ggaagatcta tattaccctg ttatgttgaa gacgagctag tgttattcct     60

<210> SEQ ID NO 34
<211> LENGTH: 2003
<212> TYPE: DNA
<213> ORGANISM: Artificial Sequence
<220> FEATURE:
<223> OTHER INFORMATION: Unknown
<220> FEATURE:
<221> NAME/KEY: misc_feature
<223> OTHER INFORMATION: Nourseothricin cassette

<400> SEQUENCE: 34
agcttgcgct tttccgaga actccccata agtcaacggc tccaatcaag aatgtatccg      60
acaacggcga gcatagcaac acgtccgtct tggagtaga atcatcatgt tgtggatgaa     120
tacacagatg aatgacatta aaagcatgaa catgttagag agtaggaggt agagattgat    180
atggtagcat tgcgatgttt gttttttggtc agcatatgat gagtggatac caatatgatg    240
aaagttgaat ctcgcgtttg agctcagcgg tacgttattg atcgaaagta gcctgatcaa    300
aatccttgga gagtacaaga ggatcaaaga atccagtggg ggcgataact ccaagctcgt    360
tctcaaagag gcaatggagg tagaaactca tcccagttga gaagaagtga aggcagtggc    420
ggtggcgaaa gcagaggcaa cgaggacaga cttcctgtgg gttgatgcaa cgaatatttc    480
cagaaggaga agtttagaga gttgaaactg taagttggat tgtgagaaga tcagaagttg    540
aacgaacaca tctttccgat cattcacctc cacactgcaa caacacgta cttcttccgc     600 ggcaggtctc tgtcgccatt ctcttgtcct gttgttggct gtgagacgag gaaagcaacg    660

```
acaagtttca caaaagggag ttcctttaac gagatatgtt ttttataaag agtcccaata    720
gaaagacaaa ttgattcctc cgtgcaaacg cgcaaataaa caccacgtcc attatatcca    780
tatctttcag agtatccaac aagtgttgaa ggacaggtag ttgaagtaac gtatcttccc    840
cctcgactgg atccatcaac aaggcgaaca atccattca acctctcata aattatctga     900
tttaccaaac cgataccaaa atgaccactc ttgacgacac ggcttaccgg taccgcacca    960
gtgtcccggg ggacgccgag gccatcgagg cactggatgg gtccttcacc accgacaccg   1020
tcttccgcgt caccgccacc ggggacggct tcaccctgcg ggaggtgccg gtggacccgc   1080
ccctgaccaa ggtgttcccc gacgacgaat cggacgacga atcggacgcc ggggaggacg   1140 gcgaccgga ctcccggacg ttcgtcgcgt acggggacga cggcgacctg cgggcttcg     1200 tggtcgtctc gtactccggc tggaaccgcc ggctgaccgt cgaggacatc gaggtcgccc   1260
cggagcaccg ggggcacggg gtcgggcgcg cgttgatggg gctcgcgacg gagttcgccc   1320
gcgagcgggg cgccgggcac ctctggctgg aggtcaccaa cgtcaacgca ccggcgatcc   1380
acgcgtaccg gcggatgggg ttcaccctct gcggcctgga caccgccctg tacgacggca   1440
ccgcctcgga cggcgagcag gcgctctaca tgagcatgcc ctgccctga gcgcggccgc    1500 atactggatt ggtgaatcaa tgagccgtag cacaatggtt acattcggct agctaagatc   1560
caatggcaag gaccaagtgc tggaacttgt tttgctttag cagatcttag cgtgagaggt   1620
atttgtcctc tgtcaggagt agatagtaga tgttctttt aaactaaaat gctaactgtt    1680
ccgaattcct catcgcagct aatccgtaca tcaaaagaca aaatgctagg tatgtgtact   1740
acatctcctg ttgctagata agacatatga taggaaacac accatcaata gtcattgtag   1800
ctttacttat actacgcatt tgcactttcc cctgagtggc agaggcgcat tgagaaaatc   1860
gatctcaaca tagtttatgt agcatcccct agatccatta ctttaagtct ccttcgtctt   1920
tggtgtaggc atgttggaca caacgaggta aaacacaaca caaacaatgt gtccagcaaa   1980
gtagtagctg ctccagttct ccc                                           2003
```

<210> SEQ ID NO 35
<211> LENGTH: 24
<212> TYPE: DNA
<213> ORGANISM: Artificial Sequence
<220> FEATURE:
<223> OTHER INFORMATION: Primer Tp-PEPCK-F

<400> SEQUENCE: 35
caccatgatt gccacgcaaa gccg                                            24

<210> SEQ ID NO 36
<211> LENGTH: 22
<212> TYPE: DNA
<213> ORGANISM: Artificial Sequence
<220> FEATURE:
<223> OTHER INFORMATION: Primer Tp-PEPCK-R

<400> SEQUENCE: 36
taagatcttt ggcccataga tt                                              22

<210> SEQ ID NO 37
<211> LENGTH: 70
<212> TYPE: DNA
<213> ORGANISM: Artificial Sequence
<220> FEATURE:
<223> OTHER INFORMATION: Primer Tpconj-F1

```
<400> SEQUENCE: 37
taacactagc tcgtcttcac gtaactataa cggtcctaat tgagctagtc agtcatcgcc      60
tagcttcgga                                                            70

<210> SEQ ID NO 38
<211> LENGTH: 71
<212> TYPE: DNA
<213> ORGANISM: Artificial Sequence
<220> FEATURE:
<223> OTHER INFORMATION: Primer Tpconj-R1

<400> SEQUENCE: 38
agcagggtta tgcagcggaa gatctatatt accctgttat tggcggccgg ccgctctaga      60
actagtggat c                                                          71
```